United States Patent
Gunderson et al.

(10) Patent No.: US 10,350,570 B2
(45) Date of Patent: Jul. 16, 2019

(54) COMPOSITIONS AND METHODS FOR SINGLE MOLECULAR PLACEMENT ON A SUBSTRATE

(71) Applicant: Illumina, Inc., San Diego, CA (US)

(72) Inventors: Kevin L. Gunderson, San Diego, CA (US); Jingwei Bai, San Diego, CA (US); Boyan Boyanov, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 13 days.

(21) Appl. No.: 15/535,695

(22) PCT Filed: Dec. 14, 2015

(86) PCT No.: PCT/US2015/065526
§ 371 (c)(1),
(2) Date: Jun. 13, 2017

(87) PCT Pub. No.: WO2016/100196
PCT Pub. Date: Jun. 23, 2016

(65) Prior Publication Data
US 2018/0141020 A1    May 24, 2018

Related U.S. Application Data

(60) Provisional application No. 62/092,171, filed on Dec. 15, 2014.

(51) Int. Cl.
*C12Q 1/68*     (2018.01)
*B01J 19/00*    (2006.01)
*C12Q 1/6837*   (2018.01)

(52) U.S. Cl.
CPC .......... *B01J 19/0046* (2013.01); *C12Q 1/68* (2013.01); *C12Q 1/6837* (2013.01); *B01J 2219/00274* (2013.01)

(58) Field of Classification Search
None
See application file for complete search history.

(56) References Cited

U.S. PATENT DOCUMENTS

| | | | |
|---|---|---|---|
| 5,223,414 A | 6/1993 | Zarling et al. | |
| 6,210,891 B1 | 4/2001 | Nyren et al. | |
| 6,258,568 B1 | 7/2001 | Nyren | |
| 6,266,459 B1 | 7/2001 | Walt et al. | |
| 6,274,320 B1 | 8/2001 | Rothberg et al. | |
| 6,355,431 B1 | 3/2002 | Chee et al. | |
| 6,737,236 B1 | 5/2004 | Pieken et al. | |
| 6,770,441 B2 | 8/2004 | Dickinson et al. | |
| 6,859,570 B2 | 2/2005 | Walt et al. | |
| 7,001,792 B2 | 2/2006 | Sauer et al. | |
| 7,057,026 B2 | 6/2006 | Barnes et al. | |
| 7,211,414 B2 | 5/2007 | Hardin et al. | |
| 7,259,258 B2 | 8/2007 | Kozlov et al. | |
| 7,315,019 B2 | 1/2008 | Turner et al. | |
| 7,329,492 B2 | 2/2008 | Hardin et al. | |
| 7,375,234 B2 | 5/2008 | Sharpless et al. | |
| 7,399,590 B2 | 7/2008 | Piepenburg et al. | |
| 7,405,281 B2 | 7/2008 | Xu et al. | |
| 7,427,678 B2 | 9/2008 | Pieken et al. | |
| 7,829,284 B2 | 11/2010 | Kong et al. | |
| 8,715,966 B2 | 5/2014 | Xiaohai et al. | |
| 2008/0108082 A1 | 5/2008 | Rank et al. | |
| 2008/0280773 A1 | 11/2008 | Fedurco et al. | |
| 2009/0026082 A1 | 1/2009 | Rothberg et al. | |
| 2009/0127589 A1 | 5/2009 | Rothberg et al. | |
| 2010/0111768 A1 | 5/2010 | Banerjee et al. | |
| 2010/0137143 A1 | 6/2010 | Rothberg et al. | |
| 2010/0282617 A1 | 11/2010 | Rothberg et al. | |
| 2011/0059865 A1 | 3/2011 | Smith et al. | |
| 2012/0270305 A1 | 10/2012 | Reed et al. | |
| 2012/0316086 A1 | 12/2012 | Lin et al. | |
| 2013/0116153 A1 | 5/2013 | Bowen et al. | |
| 2013/0210008 A1 | 8/2013 | Feitsma et al. | |
| 2013/0338042 A1 | 12/2013 | Shen et al. | |
| 2014/0079923 A1 | 3/2014 | George et al. | |
| 2014/0243224 A1 | 8/2014 | Barnard et al. | |

FOREIGN PATENT DOCUMENTS

| | | |
|---|---|---|
| WO | WO 91/06678 A1 | 5/1991 |
| WO | WO 00/63437 A2 | 10/2000 |
| WO | WO 02/074988 A2 | 9/2002 |
| WO | WO 2004/018497 A2 | 3/2004 |
| WO | WO 2005/065814 A1 | 7/2005 |
| WO | WO 2006/138257 A2 | 12/2006 |
| WO | WO 2007/123744 A2 | 11/2007 |
| WO | WO 2013-012440 A2 * | 1/2013 |
| WO | WO 2014/189768 A1 | 11/2014 |

OTHER PUBLICATIONS

Bentley et al. 2008. Accurate whole human genome sequencing using reversible terminator chemistry. *Nature*, 456:53-59.

Blicharz, et al. 2009. Fiber-optic microsphere based antibody array for the analysis of inflammatory cytokines in saliva. *Anal. Chem.*, 81(6):2106-2114.

Cockroft et al. 2008. A single-molecule nanopore device detects DNA polymerase activity with single-nucleotide resolution. *J. Am. Chem. Soc.*, 130(3):818-820.

Deamer et al. 2000. Nanopores and nucleic acids: prospects for ultrarapid sequencing. *Trends Biotechnol.*, 18:147-151.

Deamer et al. 2002. Characterization of nucleic acids by nanopore analysis. *Acc. Chem. Res.*, 35(10):817-825.

Deng et al. 2015. Bioanalytical applications of isothermal nucleic acid amplification techniques. *Analytica Chimica Acta*, 853:30-45.

Feeney, E. F., & Whitaker, J. R. 1982. Modification of Proteins: Food, Nutritional, and Pharmaceutical Aspects; Advances in Chemistry Series, vol. 198, American Chemical Society, Washington, D.C., Table of Contents, 5 pages.

Healy, K. 2007. Nanopore-based single-molecule DNA analysis. *Nanomedicine*, 2(4):459-481.

(Continued)

*Primary Examiner* — James Martinell
(74) *Attorney, Agent, or Firm* — Knobbe Martens Olson & Bear LLP

(57) ABSTRACT

Provided herein are methods and compositions for placing single target molecules on a patterned substrate.

25 Claims, 10 Drawing Sheets
Specification includes a Sequence Listing.

(56) References Cited

OTHER PUBLICATIONS

Hermanson, G. T. (2013). *Bioconjugate Techniques*, 3rd Ed. New York: Academic Press, Table of Contents, 4 pages.
Jung et al. 2007. Self-directed and self-oriented immobilization of antibody by protein G-DNA conjugate. *Analytical Chemistry*, 79(17):6534-6541.
Li et al. 2003. DNA molecules and configurations in a solid-state nanopore microscope. *Nat. Mater.*, 2:611-615.
March, J. 1985. *Advanced Organic Chemistry: Reactions, Mechanisms, and Structure*, 3rd Ed. New York: John Wiley & Sons, Table of Contents, 5 pages.
Soni et al. 2007. Progress toward ultrafast DNA sequencing using solid-state nanopores. *Clin. Chem.*, 53(11):1996-2001.
Thornton, J.A. 1977. High rate thick film growth. *Annual Review of Materials Science*, 7:239-260.
International Search Report dated Mar. 16, 2016 for International Application No. PCT/US2015/065526 filed Dec. 14, 2015.
Written Opinion of the International Searching Authority dated Mar. 16, 2016 for International Application No. PCT/US2015/065526 filed Dec. 14, 2015.

\* cited by examiner

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
aatgatacgg cgaccaccga                                            20

<210> SEQ ID NO 2
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 2
```
caagcagaag acggcatacg a                                              21

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
tcggtggtcg ccgtatcatt                                                20

<210> SEQ ID NO 4
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 4
tcgtatgccg tcttctgctt g                                              21

<210> SEQ ID NO 5
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 5
acactctttc cctacacgac gctcttccga tct                                 33

<210> SEQ ID NO 6
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 6
cggtctcggc attcctgctg aaccgctctt ccgatct                             37

<210> SEQ ID NO 7
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 7
agatcggaag agcgtcgtgt agggaaagag tgt                                 33

<210> SEQ ID NO 8
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 8
agatcggaag agcggttcag caggaatgcc gagaccg                             37

COMPOSITIONS AND METHODS FOR SINGLE MOLECULAR PLACEMENT ON A SUBSTRATE

This application is the U.S. National Phase of Application No. PCT/US2015/065526 entitled "COMPOSITIONS AND METHODS FOR SINGLE MOLECULAR PLACEMENT ON A SUBSTRATE" filed Dec. 14, 2015, which designated the United States, and which claims the benefit of U.S. Provisional Application No. 62/092,171, filed Dec. 15, 2014, which is hereby incorporated by reference in its entirety and for all purposes.

FIELD

The present disclosure relates to the field of molecular biology and more specifically to compositions and methods for placing single target molecules on a patterned substrate.

BACKGROUND

Single molecular placement has useful applications in fields such as biomolecular kinetic study, drug discovery and nucleic acid sequencing. For example, single molecule DNA sequencing has been achieved by placing a single polymerase into a wave guide having nanometer dimensions. Single molecule DNA sequencing also has been achieved using nanopore structures, which loads a single nanopore forming protein into a lipid bilayer.

Currently, single molecular placement is mostly achieved by molecular size exclusion effect through limiting the anchoring space to the level of the single molecule size. This approach requires utilization of high resolution lithography and results in a relatively low loading efficiency because of the small target area. Loading a single nanopore into a lipid bilayer is mostly accomplished by monitoring the ionic current change during the loading process, which lacks compatibility with large scale production.

Thus, there exists a need for an efficient method for the placement of a single molecule onto a target area. The present invention satisfies this need and provides related advantages as well.

SUMMARY

Provided herein, inter alia, are substrates and methods useful for placing a single molecule onto a target area. In a first aspect is a substrate that includes a plurality of first and second capture primers immobilized to a feature on the substrate. At least one target polynucleotide, one end attached to one of the capture primers and the other end linked to a target molecule, wherein the target polynucleotide includes a target region flanked by first and second capture primer binding regions complementary to the first and second capture primers, the second capture primer binding region includes a base pair mismatch to the second capture primer, and a plurality of clonal amplicons complementary to the target polynucleotide immobilized to the feature. In some embodiments, the base pair mismatch is a 1, 2, 3, 4, 5, 6, 7, 8, 9, or 10 base pair mismatch. In some embodiments, the base pair mismatch is a three base pair mismatch.

In some embodiments the substrate further includes a plurality of features. In some embodiments the feature includes a single target molecule. In some embodiments the feature is filled to capacity with the plurality of clonal amplicons. In some embodiments the plurality of features includes a single target molecule. In some embodiments two or more of the features include different single target molecules. In some embodiments the features are filled to capacity with the plurality of clonal amplicons.

In some embodiments the target polynucleotide includes one or more polynucleotides selected from the group consisting of RNA, DNA and PNA. In some embodiments the target polynucleotide includes double stranded DNA (dsDNA). In some embodiments the target polynucleotide includes less than 1,000 nucleotides. In some embodiments the target polynucleotide includes between 10 to 25, 26 to 50, 51 to 100, 101 to 200, 201 to 300, 301 to 400, 401 to 500, 501 to 600, 601 to 700, 701 to 800, 801 to 900, or 901 to 1000 nucleotides.

In some embodiments the target molecule includes a polypeptide, polynucleotide, carbohydrate, amino acid, nucleotide, monosaccharide, hapten, ligand, antigen, analyte, small molecule organic compound or inorganic compound. In some embodiments the target molecule includes a polypeptide. In some embodiments the polypeptide is selected from the group consisting of a nanopore, binding polypeptide and enzyme. In some embodiments the nanopore pore is selected from the group consisting of MspA, OmpF, OmpG, NalP, WZA, ClyA toxin, α-hemolysin, anthrax toxin, leukocidins, ion channels, protein nanopore, and DNA origami nanopore.

In some embodiments the binding polypeptide is selected from the group consisting of an antibody, a Fab, a Fab', a F(ab')$_2$, a scFV, a diabody, a triabody, a minibody and a single-domain antibody (sdAB), T cell receptor, microcins, Neuropeptides, G-protein coupled receptors, antibody, epidermal growth factor receptor and HER2. In some embodiments the enzyme is selected from the group consisting of a recombinase, polymerase, helicase, transpoase, ligase, deaminase, oxidase and kinase.

In some embodiments the substrate includes one or more materials selected from the group consisting of glass, silicon, plastic and biopolymer. In some embodiments the features are separated by interstitial regions that lack a target polynucleotide. In some embodiments the features include a bead, well, channel, ridge, projection or combination thereof. In some embodiments the well is a microwell or nanowell. In some embodiments the substrate further includes a hydrogel or covalently-linked gel.

Also provided herein are methods of placing a single target molecule on a feature of a substrate. In one aspect, the method is a method of placing a single target molecule on a feature of a substrate by hybridizing a plurality of first and second capture primers immobilized to a feature on a substrate with at least one target polynucleotide, where the target polynucleotide includes a target region flanked by first and second capture primer binding regions complementary to the first and second capture primers, and the second capture primer binding region includes a base pair mismatch to the second capture primer and being linked to a target molecule. The method further includes amplifying the at least one target polynucleotide at an average amplification rate that exceeds an average transport rate of a target polynucleotide to a feature to produce a plurality of clonal amplicons complementary to the target polynucleotide.

In some embodiments of the methods described herein the base pair mismatch is a 1, 2, 3, 4, 5, 6, 7, 8, 9, or 10 base pair mismatch. In some embodiments of the methods described herein the base pair mismatch is a three base pair mismatch. In some embodiments of the methods described herein the substrate comprises a plurality of features. In some embodiments of the methods described herein the feature includes a single target molecule. In some embodiments of the methods described herein the feature is filled to capacity with the plurality of clonal amplicons. In some embodiments of the methods described herein the plurality of features includes a single target molecule. In some embodiments of the methods described herein the two or more of the features include different single target molecules. In some embodiments of the methods described herein the features are filled to capacity with the plurality of clonal amplicons.

In some embodiments of the methods described herein the amplifying comprises an isothermal amplification. In some embodiments of the methods described herein the isothermal amplification further includes single stranded binding polypeptide. In some embodiments of the methods described herein the isothermal amplification includes kinetic exclusion amplification. In some embodiments of the methods described herein the isothermal amplification further includes kinetic exclusion amplification.

In some embodiments of the methods described herein the average amplification rate of subsequent amplicons produced at the feature exceeds the average amplification rate of a first amplicon. In some embodiments of the methods described herein the target polynucleotide includes one or more polynucleotides selected from the group consisting of RNA, DNA, and PNA. In some embodiments of the methods described herein the target polynucleotides include double stranded DNA (dsDNA). In some embodiments the target polynucleotide comprises less than 1,000 nucleotides. In some embodiments of the methods described herein the target polynucleotide comprises between 10 to 25, 26 to 50, 51 to 100, 101 to 200, 201 to 300, 301 to 400, 401 to 500, 501 to 600, 601 to 700, 701 to 800, 801 to 900, or 901 to 1000 base pairs in length.

In some embodiments of the methods described herein the target molecule includes a polypeptide, polynucleotide, carbohydrate, amino acid, nucleotide, monosaccharide, hapten, ligand, antigen, analyte, small molecule organic compound or inorganic compound. In some embodiments of the methods described herein the target molecule includes a polypeptide. In some embodiments of the methods described herein the polypeptide is selected from the group consisting of a nanopore, binding polypeptide and enzyme. In some embodiments of the methods described herein the nanopore is selected from the group consisting of MspA, OmpF, OmpG, NalP, WZA, ClyA toxin, α-hemolysin, anthrax toxin, leukocidins and DNA origami nanopore. In some embodiments of the methods described herein the binding polypeptide is selected from the group consisting of an antibody, a Fab, a Fab', a F(ab')$_2$, a scFV, a diabody, a triabody, a minibody and a single-domain antibody (sdAB), T cell receptor, microcins, Neuropeptides, G-protein coupled receptors, antibody, epidermal growth factor receptor and HER2.

In some embodiments of the methods described herein the enzyme is selected from the group consisting of a recombinase, polymerase, helicase, transpoase, ligase, deaminase, oxidase and kinase. In some embodiments of the methods described herein the substrate includes one or more materials selected from the group consisting of glass, silicon, plastic and biopolymer. In some embodiments of the methods described herein the features are separated by interstitial regions that lack a target polynucleotide. In some embodiments of the methods described herein the features include a bead, well, channel, ridge, projection or combination thereof. In some embodiments of the methods described herein the well is a microwell or nanowell. In some embodiments of the methods described herein the substrate further includes a hydrogel or covalently-linked gel.

DETAILED DESCRIPTION

This disclosure is directed to compositions and methods for placing a single molecule onto selected substrate area. The placement of a single molecule or single molecular placement can be useful in a variety of applications where it is desirable to determine a single molecular interaction as opposed to average measurements between populations. The placement of a single molecule also can be useful when it is desirable to use a single molecule to interrogate another molecular entity at the single molecular level.

Figure 1:
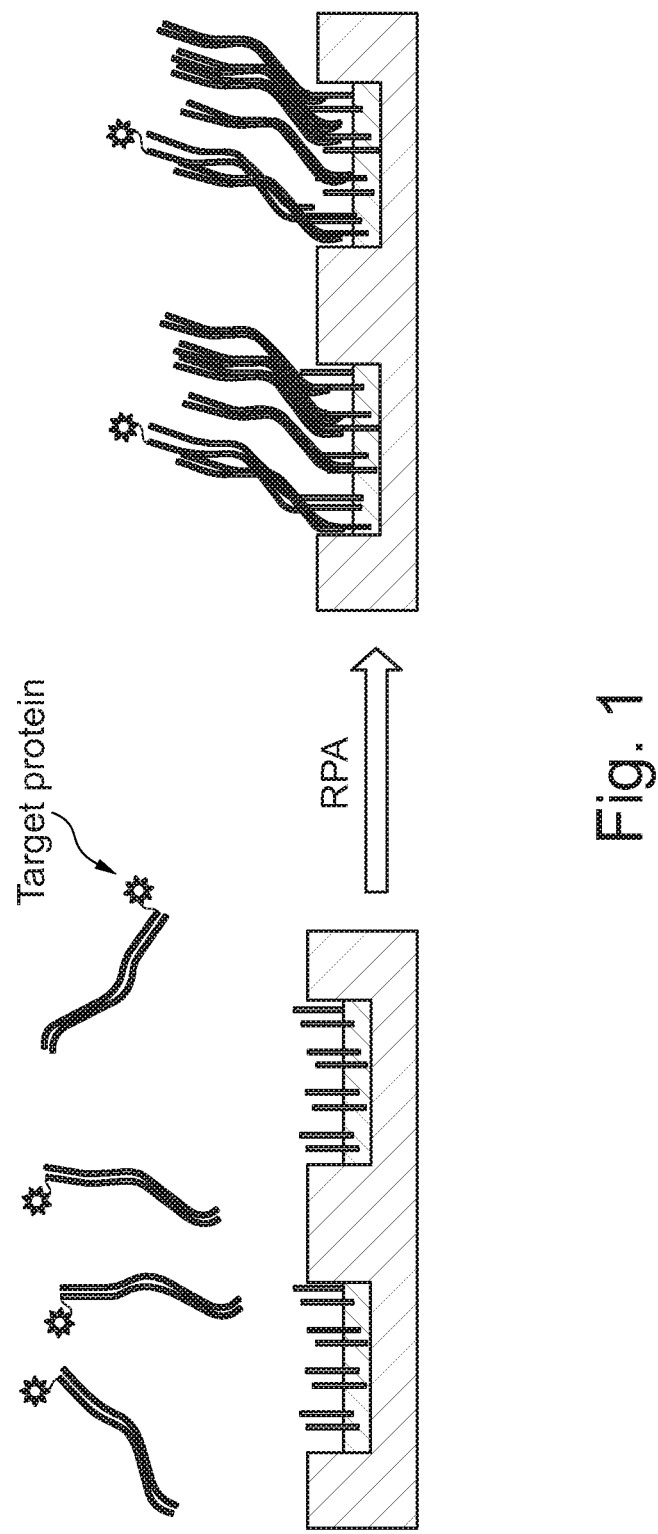
FIG. 1 illustrates the placement of a single target molecule in each of a plurality of features using kinetic exclusion amplification (KEA) of the target polynucleotide attached to the target molecule.

In one exemplary embodiment illustrated in FIG. 1, this disclosure is directed to placement of a single molecule onto a target area of a substrate using kinetic exclusion assay (KEA). In this embodiment, the target area of a substrate is first functionalized with a KEA primer, and the target molecule is linked to a double stranded nucleic acid which can be quickly amplified by KEA. When the target molecule lands on the substrate, the linked nucleic acid quickly amplifies to fill the entire pad and prevent further landing of a different molecule. This exemplary method is less restricted from the critical dimension (CD) of the target area, and the loading through-put will be higher than methods based on size exclusion effect. Moreover, KEA is a self-limiting process and therefore compatible with large scale production.

As used herein, the term "substrate" is intended to mean a solid support. The term includes any material that can serve as a solid or semi-solid foundation for creation of features such as wells for the deposition of biopolymers, including nucleic acids, polypeptide and/or other polymers. A substrate of the invention is modified, for example, or can be modified to accommodate attachment of biopolymers by a variety of methods well known to those skilled in the art. Exemplary types of substrate materials include glass, modified glass, functionalized glass, inorganic glasses, microspheres, including inert and/or magnetic particles, plastics, polysaccharides, nylon, nitrocellulose, ceramics, resins, silica, silica-based materials, carbon, metals, an optical fiber or optical fiber bundles, a variety of polymers other than those exemplified above and multiwell microtier plates. Specific types of exemplary plastics include acrylics, polystyrene, copolymers of styrene and other materials, polypropylene, polyethylene, polybutylene, polyurethanes and Teflon™ (e.g., polytetrafluoroethylene, perfluoroalkoxy, fluorinated ethylene propylene and derivatives thereof). Specific types of exemplary silica-based materials include silicon and various forms of modified silicon.

In the methods and compositions presented herein, polynucleotides can be immobilized to a substrate described herein. In some embodiments, the polynucleotides are covalently immobilized to the substrate. When referring to immobilization of molecules (e.g. nucleic acids) to a substrate, the terms "immobilized" and "attached" are used interchangeably herein and both terms are intended to encompass direct or indirect, covalent or non-covalent attachment, unless indicated otherwise, either explicitly or by context. In certain embodiments of the invention covalent attachment may be preferred, but generally all that is required is that the molecules (e.g. nucleic acids) remain immobilized or attached to the support under the conditions in which it is intended to use the substrate.

Certain embodiments of the invention may make use of substrates that include an inert substrate or matrix (e.g. glass slides, polymer beads etc.) which has been functionalized, for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass, particularly polyacrylamide hydrogels as described in WO 2005/065814 and US 2008/0280773, the contents of which are incorporated herein in their entirety by reference. In such embodiments, the biomolecules (e.g. polynucleotides) may be directly covalently attached to the intermediate material (e.g. the hydrogel) but the intermediate material may itself be non-covalently attached to the substrate or matrix (e.g. the glass substrate). The terms "covalent attachment to a solid support" and "covalent attachment to a substrate" are used interchangeably and are to be interpreted accordingly as encompassing this type of arrangement.

Exemplary covalent linkages include, for example, those that result from the use of click chemistry techniques. Exemplary non-covalent linkages include, but are not limited to, non-specific interactions (e.g. hydrogen bonding, ionic bonding, van der Waals interactions etc.) or specific interactions (e.g. affinity interactions, receptor-ligand interactions, antibody-epitope interactions, avidin-biotin interactions, streptavidin-biotin interactions, lectin-carbohydrate interactions, etc.). Exemplary linkages are set forth in U.S. Pat. Nos. 6,737,236; 7,259,258; 7,375,234 and 7,427,678; and US Pat. Pub. No. 2011/0059865 A1, each of which is incorporated herein by reference. Covalent linkages can include those formed using conjugation chemistry as described herein.

The terms "solid surface," "solid support" and other grammatical equivalents herein refer to any material that is appropriate for or can be modified to be appropriate for the attachment of the polynucleotides. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, ceramics, resins, silica or silica-based materials including silicon and modified silicon, carbon, metals, inorganic glasses, plastics, optical fiber bundles, and a variety of other polymers. Particularly useful solid supports and solid surfaces for some embodiments are located within a flow cell apparatus. Exemplary flow cells are set forth in further detail below.

Those skilled in the art will know or understand that the composition and geometry of a substrate of the invention can vary depending on the intended use and preferences of the user. Therefore, although planar substrates such as slides, chips or wafers are exemplified herein in reference to microarrays for illustration, given the teachings and guidance provided herein, those skilled in the art will understand that a wide variety of other substrates exemplified herein or well known in the art also can be used in the methods and/or compositions of the invention.

In some embodiments, the solid support comprises one or more surfaces of a flowcell. The term "flowcell" as used herein refers to a chamber comprising a solid surface across which one or more fluid reagents can be flowed. Examples of flowcells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

In some embodiments, the solid support or its surface is non-planar, such as the inner or outer surface of a tube or vessel. In some embodiments, the solid support comprises microspheres or beads. By "microspheres" or "beads" or "particles" or grammatical equivalents herein is meant small discrete particles. Suitable bead compositions include, but are not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon, as well as any other materials outlined herein for solid supports may all be used. "Microsphere Detection Guide" from Bangs Laboratories, Fishers Ind. is a helpful guide. In certain embodiments, the microspheres are magnetic microspheres or beads. The beads need not be spherical; irregular particles may be used. Alternatively or additionally, the beads may be porous. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller or larger beads may be used.

In some embodiments, the solid support includes a patterned surface. A "patterned surface" refers to an arrangement of different regions in or on an exposed layer of a solid support. For example, one or more of the regions can be a feature where one or more amplification primers are present. The features can be separated by interstitial regions where amplification primers are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. Exemplary patterned surfaces that can be used in the methods and compositions set forth herein are described in U.S. Ser. No.

13/661,524 or US Pat. App. Publ. No. 2012/0316086 A1, each of which is incorporated herein by reference.

In some embodiments, the solid support comprises an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The features in a patterned surface can be wells in an array of wells (e.g., microwells or nanowells) on glass, silicon, plastic or other suitable solid supports with patterned, covalently-linked gel such as poly(N-(5-azidoacetamidylpentyl) acrylamide-co-acrylamide) (PAZAM, see, for example, U.S. Prov. Pat. App. Ser. No. 61/753,833, which is incorporated herein by reference). The process creates gel pads used for sequencing that can be stable over sequencing runs with a large number of cycles. The covalent linking of the polymer to the wells is helpful for maintaining the gel in the structured features throughout the lifetime of the structured substrate during a variety of uses. However in many embodiments, the gel need not be covalently linked to the wells. For example, in some conditions silane free acrylamide (SFA, see, for example, U.S. Pat. App. Pub. No. 2011/0059865 A1, which is incorporated herein by reference) which is not covalently attached to any part of the structured substrate, can be used as the gel material.

In particular embodiments, a structured substrate can be made by patterning a solid support material with wells (e.g. microwells or nanowells), coating the patterned support with a gel material (e.g., PAZAM, SFA or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer nucleic acids can be attached to gel material. A solution of target polynucleotides (e.g., a fragmented human genome) can then be contacted with the polished substrate such that individual target polynucleotides will seed individual wells via interactions with primers attached to the gel material; however, the target polynucleotides will not occupy the interstitial regions due to absence or inactivity of the gel material. Amplification of the target polynucleotides will be confined to the wells since absence or inactivity of gel in the interstitial regions prevents outward migration of the growing nucleic acid colony. The process is conveniently manufacturable, being scalable and utilizing conventional micro- or nano-fabrication methods.

A patterned substrate can include, for example, wells etched into a slide or chip. The pattern of the etchings and geometry of the wells can take on a variety of different shapes and sizes so long as such features are physically or functionally separable from each other. Particularly useful substrates having such structural features are patterned substrates that can select the size of solid support particles such as microspheres. An exemplary patterned substrate having these characteristics is the etched substrate used in connection with BeadArray technology (Illumina, Inc., San Diego, Calif.). Further examples, are described in U.S. Pat. No. 6,770,441, which is incorporated herein by reference.

An array refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target polynucleotide molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "microspheres" or "beads" or "particles" or grammatical equivalents herein is meant small discrete particles. Suitable bead compositions include, but are not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and teflon, as well as any other materials outlined herein for solid supports can all be used. "Microsphere Detection Guide" from Bangs Laboratories, Fishers Ind. is a helpful guide. In certain embodiments, the microspheres are magnetic microspheres or beads.

As used herein, the term "plurality" is intended to mean a population of two or more different members. Pluralities can range in size from small, medium, large, to very large. The size of small plurality can range, for example, from a few members to tens of members. Medium sized pluralities can range, for example, from tens of members to about 100 members or hundreds of members. Large pluralities can range, for example, from about hundreds of members to about 1000 members, to thousands of members and up to tens of thousands of members. Very large pluralities can range, for example, from tens of thousands of members to about hundreds of thousands, a million, millions, tens of millions and up to or greater than hundreds of millions of members. Therefore, a plurality can range in size from two to well over one hundred million members as well as all sizes, as measured by the number of members, in between and greater than the above exemplary ranges. An exemplary number of features within a microarray include a plurality of about 500,000 or more discrete features within 1.28 cm$^2$. Exemplary nucleic acid pluralities include, for example, populations of about $1\times10^5$, $5\times10^5$ and $1\times10^6$ or more different nucleic acid species. Accordingly, the definition of the term is intended to include all integer values greater than two. An upper limit of a plurality of the invention can be set, for example, by the theoretical diversity of nucleotide sequences in a nucleic acid sample of the invention.

As used herein, the term "immobilized" when used in reference to a polynucleotide is intended to mean direct or indirect attachment to a solid support via covalent or non-covalent bond(s). In certain embodiments of the invention, covalent attachment can be used, but all that is required is that the polynucleotides remain stationary or attached to a support under conditions in which it is intended to use the support, for example, in applications requiring nucleic acid amplification and/or sequencing. Oligonucleotides to be used as capture primers or amplification primers can be immobilized such that a 3'-end is available for enzymatic extension and at least a portion of the sequence is capable of hybridizing to a complementary sequence. Immobilization can occur via hybridization to a surface attached oligonucleotide, in which case the immobilized oligonucleotide or polynucleotide can be in the 3'-5' orientation. Alternatively, immobilization can occur by means other than base-pairing hybridization, such as the covalent attachment set forth above.

As used herein, the term "polynucleotide" is intended to mean a ribonucleic or deoxyribonucleic acid or analog thereof, including a polynucleotide analyte presented in any context; for example, a probe, target or primer. Particular forms of polynucleotides of the invention include all types of nucleic acids found in an organism as well as synthetic nucleic acids such as polynucleotides produced by chemical synthesis. Particular examples of nucleic acids that are applicable for analysis through incorporation into microarrays produced by methods of the invention include genomic DNA (gDNA), DNA copied messenger RNA (cDNA), RNA copied messenger RNA (cRNA), mitochondrial DNA or genome, RNA, messenger RNA (mRNA) and/or other populations of RNA. Additional examples of polynucleotides include double stranded DNA (dsDNA), single stranded DNA (ssDNA), a gene or gene fragment (for example, a probe, primer, expressed sequence tag (EST) or serial analysis of gene expression (SAGE) tag), genomic DNA, exon, intron, transfer RNA (tRNA), ribosomal RNA (rRNA), ribozyme, recombinant polynucleotide, synthetic polynucleotide, branched polynucleotide, plasmid, vector, isolated DNA of any sequence, isolated RNA of any sequence or amplified copy of any of the foregoing. Fragments and/or portions of the above exemplary nucleic acids also are included within the meaning of the term as it is used herein.

The terms "nucleic acid," "polynucleotide" and "oligonucleotide" are used interchangeably herein. The different terms are not intended to denote any particular difference in size, sequence, or other property unless specifically indicated otherwise. For clarity of description the terms can be used to distinguish one species of nucleic acid from another when describing a particular method or composition that includes several nucleic acid species.

As used herein, the term "double-stranded," when used in reference to a polynucleotide, means that some or all of the nucleotides between complementary strands of a polynucleotide are hydrogen bonded together to form a partial or complete double helix. A partially double stranded polynucleotide can have at least 10%, 25%, 50%, 60%, 70%, 80%, 90% or 95% of its nucleotides hydrogen bonded to a complementary nucleotide.

A single-stranded polynucleotide refers to a polynucleotide that has few to none hydrogen bonds with another polynucleotide such that a double helix is not formed or is unstable under a given set of hybridization conditions.

As used herein, the term "target polynucleotide" is intended to mean a polynucleotide that is the object of an analysis, action, interrogation or use. The analysis, action or interrogation includes subjecting the target polynucleotide to, for example, copying, amplification, sequencing and/or other procedure for nucleic acid interrogation. The analysis or use also can include employing the target polynucleotide as a component in a system to analyze, perform an action or interrogate other molecular entities. The component can be structural or functional. A target polynucleotide can include nucleotide sequences additional to the target sequence to be analyzed or used. For example, a target polynucleotide can include one or more adapters, including an adapter that functions as a primer binding site, that flank(s) a target polynucleotide sequence that is to be analyzed or used in a system. A target polynucleotide hybridized to a capture oligonucleotide or capture primer can contain nucleotides that extend beyond the 5' or 3' end of the capture oligonucleotide in such a way that not all of the target polynucleotide is amenable to extension. In particular embodiments, as set forth in further detail below, a plurality of target polynucleotides includes different species that differ in their target polynucleotide sequences but have adapters that are the same for two or more of the different species. The two adapters that can flank a particular target polynucleotide sequence can have the same sequence or the two adapters can have different sequences. Accordingly, a plurality of different target polynucleotides can have the same adapter sequence or two different adapter sequences at each end of the target polynucleotide sequence. Thus, species in a plurality of target polynucleotides can include regions of known sequence that flank regions of unknown sequence that are to be evaluated by, for example, sequencing. Additionally, a plurality of target polynucleotides can be the same species or different species and can include regions of know sequence that flank regions of known sequence that are to be employed as a component in a system. In cases where the target polynucleotides carry an adapter at a single end, the adapter can be located at either the 3' end or the 5' end the target polynucleotide. Target polynucleotides can be used without any adapter, in which case a primer binding sequence can come directly from a sequence found in the target polynucleotide.

As used herein, the term "target molecule" is intended to mean any molecule that is the subject of an analysis, action, interrogation or use. The analysis, action or interrogation includes subjecting the molecule to, for example, sequencing, binding determinations, affinity measurements, catalytic measurements, substrate or product specificity and other molecular determinations. The analysis or use also can include employing the target molecule as a component in a system to analyze, perform an action or interrogate other molecular entities. The component can be structural or functional. For example, a target molecule can be a nanopore used in nanopore sequencing of nucleic acids. Other target molecules applicable in nanopore sequencing include, for example, helicases and polymerases. Other exemplary analyses or uses of a target molecule include, for example, molecular binding affinity screening, enzyme screening, compound screening and all other assays in which it is desirable to determine or measure a molecular interaction. Thus, a target molecule can be the subject of an analysis, action or interrogation or in can be used to analyze, perform an action or interrogate other molecules. Exemplary target molecules include, for example, a biopolymer including a polypeptide, polynucleotide or polysaccharide, amino acid, nucleotide, monosaccharide, disaccharide, other carbohydrate, receptor, hapten, ligand, antigen, analyte, small molecule organic compound or inorganic compound, vitamin, metabolite, antioxidant, immunosuppressant, anti-cancer drug, or any combination thereof.

Additionally, it should be appreciated that a target molecule can be attached to a polypeptide (target polypeptide) in any number of ways. For example, the target molecule can be attached using conjugation chemistry techniques known in the art and described herein. Favorable classes of conjugation chemistry include chemical reactions which proceed under relatively mild conditions. These include, but are not limited to, nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIO-CONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Exemplary reactive functional groups useful in conjugation chemistry techniques include carboxyl groups (e.g., N-hydroxysuccinimide esters, N-hydroxybenztriazole esters, acid halides, acyl imidazoles, thioesters, p-nitrophenyl esters, alkyl, alkenyl, alkynyl and aromatic esters); hydroxyl groups (i.e., converted to, for example, esters, ethers, or aldehydes); haloalkyls; dienophiles (e.g., Diels-Alder reactions); aldehyde groups; ketone groups; sulfonyl groups; amine groups; alkenes (i.e., cycloadditions and Michael additions); epoxides; phosphoramidite groups; phosphine groups; azide groups (i.e. for click-chemistry); and thiol groups. Such reactive groups can be functionalized on a target molecule or a polypeptide.

In one illustrative embodiment, the reduced thiol (—SH) group (i.e., a sulfhydryl group) of a cysteine residue can be reacted with a tether having a thiol-reactive group. Examples of such groups include maleimide and iodoacetamide. Primary thiol-reactive reagents, including iodoacetamides, maleimides, benzylic halides, and bromomethylketones can react by S-alkylation of thiols so as to generate stable thioether products; arylating reagents such as 7-nitrobenz-2,1,3-oxadiazole (NBD) halides can react with thiols or amines by a similar substitution of the aromatic halide by the nucleophile; and because the thiolate anion is a better nucleophile than the neutral thiol, cysteine is more reactive above its pKa. Additional sulfhydryl-reactive chemical groups include haloacetyls, maleimides, aziridines, acryloyls, arylating agents, vinylsulfones, pyridyl disulfides, TNB-thiols (2-nitro-5-thiobenzoic acid), and disulfide reducing agents. Such groups can conjugate to sulfhydryls via alkylation (e.g., via formation of a thioether bond) or disulfide exchange (e.g., formation of a disulfide bond). Sulfhydryl exchange reactions also suitably can be used.

Alternatively, amines (—NH$_2$) can be targeted. For example, the primary amine of the lysine residue and the polpypeptide N-terminus are relatively reactive. Amine residues can be targeted with N-hydroxysuccinimide esters (NHS esters), which can form a stable amide bond, or imidoester crosslinkers, which can react with primary amines to form amidine bonds. There are many other amine-reactive compounds. For example, synthetic chemical groups that can form chemical bonds with primary amines include isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters; such groups can conjugate to amines, for example, via acylation or alkylation.

In still other embodiments, a modified target molecule can be used to introduce a novel functionality like an azide or alkyne to be used with click chemistry. For example, thiol or amine reactivities such as described above can be used with linkers that permit the addition of azide or alkyne functionalities to further be used in a click chemistry reaction.

The ability to create an array of single molecules spaced out on a patterned surface includes a number of features and applications for chemical and biosensing. One feature of single molecule arrays includes optimization of packing density subject to the detection constraint. Detection can be performed using standard optical detection. For standard optical detection, the intermolecular spacing can be about 500 nm (e.g., the order of the wavelength of detection light). Detection can be performed using an electronic readout such as, for example, electronic readout on a CMOS chip.

The spacing of the single molecules for electronic readout (e.g., on a CMOS chip) can be such that a single molecule occupies between about 1 to about 15 um in size. The spacing of the single molecules for electronic readout (e.g., on a CMOS chip) can be such that a single molecule occupies between about 1 to about 12 um in size. The spacing of the single molecules for electronic readout (e.g., on a CMOS chip) can be such that a single molecule occupies between about 1 to about 10 um in size. The spacing of the single molecules for electronic readout (e.g., on a CMOS chip) can be such that a single molecule occupies between about 1 to about 9 um in size. The spacing of the single molecules for electronic readout (e.g., on a CMOS chip) can be such that a single molecule occupies between about 1 to about 8 um in size. The spacing of the single molecules for electronic readout (e.g., on a CMOS chip) can be such that a single molecule occupies between about 1 to about 7 um in size. The spacing of the single molecules for electronic readout (e.g., on a CMOS chip) can be such that a single molecule occupies between about 1 to about 6 um in size. The spacing of the single molecules for electronic readout (e.g., on a CMOS chip) can be such that a single molecule occupies between about 1 to about 5 um in size. The spacing of the single molecules for electronic readout (e.g., on a CMOS chip) can be such that a single molecule occupies between about 1 to about 4 um in size. The spacing of the single molecules for electronic readout (e.g., on a CMOS chip) can be such that a single molecule occupies between about 1 to about 3 um in size. The spacing of the single molecules for electronic readout (e.g., on a CMOS chip) can be such that a single molecule occupies between about 1 um in size. The spacing of the single molecules for electronic readout (e.g., on a CMOS chip) can be such that a single molecule occupies between about 2 um in size. The spacing of the single molecules for electronic readout (e.g., on a CMOS chip) can be such that a single molecule occupies between about 3 um in size. The spacing of the single molecules for electronic readout (e.g., on a CMOS chip) can be such that a single molecule occupies between about 4 um in size. The spacing of the single molecules for electronic readout (e.g., on a CMOS chip) can be such that a single molecule occupies between about 5 um in size. The spacing of the single molecules for electronic readout (e.g., on a CMOS chip) can be such that a single molecule occupies between about 6 um in size. The spacing of the single molecules for electronic readout (e.g., on a CMOS chip) can be such that a single molecule occupies between about 7 um in size. The spacing of the single molecules for electronic readout (e.g., on a CMOS chip) can be such that a single molecule occupies between about 8 um in size. The spacing of the single molecules for electronic readout (e.g., on a CMOS chip) can be such that a single molecule occupies between about 9 um in size. The spacing of the single molecules for electronic readout (e.g., on a CMOS chip) can be such that a single molecule occupies between about 10 um in size. The spacing of the single molecules for electronic readout (e.g., on a CMOS chip) can be such that a single molecule occupies between about 11 um in size. The spacing of the single molecules for electronic readout (e.g., on a CMOS chip) can be such that a single molecule occupies between about 12 um in size. The spacing of the single molecules for electronic readout (e.g., on a CMOS chip) can be such that a single molecule occupies between about 13 um in size. The spacing of the single molecules for electronic readout (e.g., on a CMOS chip) can be such that a single molecule occupies between about 14 um in size. The spacing of the single molecules for electronic readout (e.g., on a CMOS chip) can be such that a single molecule occupies between about 15 um in size. In embodiments, a single molecule occupies about a single pixel (e.g., 1-10 um in size).

Single molecule sensors can be used in a wide variety of applications including, but not limited to, DNA sequencing, chemical sensing, and protein/antigen assays using antibodies, etc. In embodiments, a single polymerase molecule can be used in DNA sequences to sequence DNA in real time. In other embodiments, nanopore-based DNA sequencing can be used where the placement of a single nanopore in the bilayer is useful to generate interpretable data.

As used herein, the term "amplicon," when used in reference to a nucleic acid, is intended to mean the product of copying the nucleic acid, wherein the product has a nucleotide sequence that is the same as or complementary to at least a portion of the nucleotide sequence of the copied nucleic acid. An amplicon can be produced by any of a variety of amplification methods that use the nucleic acid, or an amplicon thereof, as a template including, for example, recombinase polymerase amplification, kinetic exclusion amplification, polymerase extension, polymerase chain reaction (PCR), rolling circle amplification (RCA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid can be a complementary copy. Subsequent amplicons are copies that are created, after generation of the first amplicon, from the target polynucleotide or from the first amplicon. A subsequent amplicon can have a sequence that is substantially complementary to the target polynucleotide or substantially identical to the target polynucleotide.

The number of template copies or amplicons that can be produced can be modulated by appropriate modification of the amplification reaction including, for example, varying the number of amplification cycles run, using polymerases of varying processivity in the amplification reaction and/or varying the length of time that the amplification reaction is run, as well as modification of other conditions known in the art to influence amplification yield. The number of copies of a nucleic acid template can be at least 1, 10, 100, 200, 500, 1000, 2000, 3000, 4000, 5000, 6000, 7000, 8000, 9000 and 10,000 copies, and can be varied depending on the particular application.

The term "clonal" when used in reference to amplicons or a plurality of amplicons is intend to mean a population of nucleic acids that is homogeneous with respect to a particular nucleotide sequence. The homogenous sequence can be at least 10 nucleotides long, or longer, for example, at least 50, 100, 250, 500 or 1000 nucleotides long. A clonal population can be derived from a single target polynucleotide or template nucleic acid. Essentially all of the nucleic acids in a clonal population have the same nucleotide sequence. It will be understood that a small number of mutations (e.g. due to amplification artifacts) can occur in a clonal population without departing from clonality.

As used herein, the term "capture primer" is intended to mean an oligonucleotide having a nucleotide sequence that is capable of specifically annealing to a single stranded polynucleotide sequence to be analyzed or subjected to a nucleic acid interrogation under conditions encountered in a primer annealing step of, for example, an amplification or sequencing reaction. The term also is intended to mean an oligonucleotide having a nucleotide sequence that is capable of specifically annealing to a single stranded polynucleotide sequence that is used to analyze, interrogate or perform an action on another molecular entity.

As used herein, the term "target specific" when used in reference to a capture primer or other oligonucleotide is intended to mean a capture primer or other oligonucleotide that includes a nucleotide sequence specific to a target polynucleotide sequence, namely a sequence of nucleotides capable of selectively annealing to an identifying region of a target polynucleotide. Target specific capture primers can have a single species of oligonucleotide, or it can include two or more species with different sequences. Thus, the target specific capture primers can be two or more sequences, including 3, 4, 5, 6, 7, 8, 9 or 10 or more different sequences. The target specific capture oligonucleotides can include a target specific capture primer sequence and universal capture primer sequence. Other sequences such as sequencing primer sequences and the like also can be included in a target specific capture primer.

In comparison, the term "universal" when used in reference to a capture primer or other oligonucleotide sequence is intended to mean a capture primer or other oligonucleotide having a common nucleotide sequence among a plurality of capture primers. A common sequence can be, for example, a sequence complementary to the same adapter sequence. Universal capture primers are applicable for interrogating a plurality of different polynucleotides without necessarily distinguishing the different species whereas target specific capture primers are applicable for distinguishing the different species.

The disclosure provides a substrate including: (a) a plurality of first and second capture primers immobilized to a feature on a substrate; (b) at least one target polynucleotide, one end attached to one of the capture primers and the other end linked to a target molecule, wherein the target polynucleotide comprises a target region flanked by first and second capture primer binding regions complementary to the first and second capture primers, the second capture primer binding region including a base pair mismatch to the second capture primer, and (c) a plurality of clonal amplicons complementary to the target polynucleotide immobilized to the feature.

In one embodiment, a substrate of the disclosure can contain at least a single target molecule localized to a site on a substrate. Embodiments for use in single molecular analyses and/or interrogations, a substrate of the disclosure will have a single target molecule localized to a site on a substrate. Single target molecules can be localized to one or more sites on a substrate using, for example, the methods and molecular components described herein.

Substrates for localizing a single target molecule can include those materials and formats described previously as well as other materials and formats well known in the art. For example, in some embodiments, a substrate can be any insoluble solid support, semi-solid support or matrix to which a biomolecule can be attached including, for example, a polynucleotide. Exemplary solid supports include glass, modified glass, functionalized glass, inorganic glasses, microspheres (e.g. inert and/or magnetic particles), plastics, polysaccharides, nylon, nitrocellulose, ceramics, resins, silica, silica-based materials, carbon, metals, an optical fiber or optical fiber bundles, polymers and multiwell (e.g. microtiter) plates. Exemplary plastics include acrylics, polystyrene, copolymers of styrene and other materials, polypropylene, polyethylene, polybutylene, polyurethanes and Teflon™. Exemplary silica-based materials include silicon, including silicon wafers, and various forms of modified silicon. Other solid supports applicable for use as a substrate include, for example, latex beads, dextran beads, polyacrylamide gel, gold surfaces, silicon nitride surfaces, or metal oxide surfaces.

In some embodiments the surface can be any desirable shape including, for example, planar, spherical or porous material suitable for single molecular placement as described herein. For example, the solid support can be a planar glass surface.

In particular embodiments, a substrate can be within or part of a vessel such as a well, tube, channel, cuvette, Petri plate, bottle or the like to allow the interaction with solutions of various reagents. A particularly useful vessel is a flowcell, for example, as described in US 2010/01 11768 A1 or Bentley et al, Nature 456:53-59 (2008). Exemplary flowcells include those that are commercially available from Illumina, Inc. (San Diego, Calif.). Another particularly useful vessel is a well in a multiwell plate or microtiter plate.

In some embodiments, the site on a substrate for localization of at least one target molecule can be a feature. As described above and below, the features can be present in any of a variety of desired formats. For example, a feature can be a well, pit, channel, ridge, raised region, peg, post or the like. As exemplified previously, the feature can be a bead or can contain a bead.

In particular embodiments a feature need not contain a bead or particle. Exemplary features include wells that are present in substrates used, for example, in commercial sequencing platforms sold by 454 LifeSciences (a subsidiary of Roche, Basel Switzerland) or Ion Torrent (a subsidiary of Life Technologies, Carlsbad Calif.). Other substrates having wells include, for example, etched fiber optics and other substrates described in U.S. Pat. Nos. 6,266,459; 6,355,431; 6,770,441; 6,859,570; 6,210,891; 6,258,568; 6,274,320; US 2009/0026082 A1; US 2009/0127589 A1; US 2010/0137143 A1; US 2010/0282617 A1 or PCT Publication No. WO 00/63437. In several cases the substrates are exemplified in these references for applications that use a bead in the well. The well-containing substrates can be used with or without beads in the compositions of the present disclosure.

In some embodiments, wells of a substrate can include gel material as set forth in U.S. Prov. App. No. 61/769,289, which is incorporated herein by reference.

In one embodiment, a feature can be a metal feature on a non-metallic surface such as glass, plastic or other materials exemplified above. A metal layer can be deposited on a surface using methods known in the art such as wet plasma etching, dry plasma etching, atomic layer deposition, ion beam etching, chemical vapor deposition, vacuum sputtering or the like. Any of a variety of commercial instruments can be used as appropriate including, for example, the FlexAL®, OpAL®, Ionfab 300Plus®, or Optofab 3000® systems (Oxford Instruments, UK). A metal layer can also be deposited by e-beam evaporation or sputtering as set forth in Thornton, Ann. Rev. Mater. Sci. 7:239-60 (1977). Metal layer deposition techniques, such as those exemplified above, can be combined, for example, with photolithography techniques to create metal regions or patches on a surface. Exemplary methods for combining metal layer deposition techniques and photolithography techniques are described in U.S. Ser. No. 13/492,661.

A substrate of the disclosure can have first and second capture primers immobilized to a feature on the substrate. The first and second capture primers can be a plurality of first capture primers and a plurality of second capture primers. In some embodiments, the first and second capture primers can be directed to different sequences of a target polynucleotide and, therefore, exhibit specificity to different regions of the target polynucleotide. In other embodiments, the first and second capture primers can be directed to different target polynucleotides.

Figure 2:
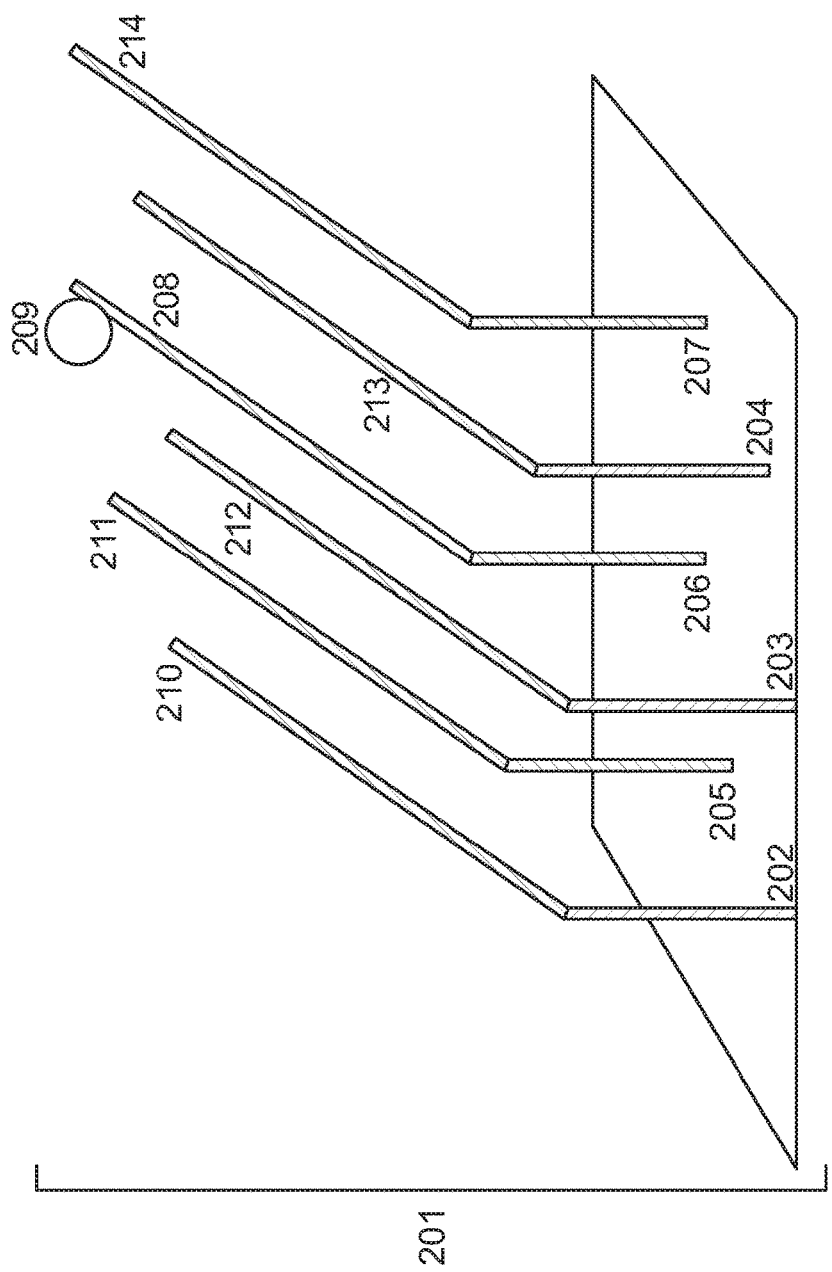
FIG. 2 shows an exemplary substrate.

An exemplary substrate is depicted in FIG. 2. As shown in FIG. 2, a substrate (201) can contain a plurality of first capture primers (202, 203, 204) and a plurality of second capture primers (205, 206, 207). The substrate (201) can further comprise a target polynucleotide (208) that is attached at one end to a capture primer (202). The substrate (201) can further comprise amplicons (210, 211, 212, 213, and 214) of the target polynucleotide (208). Additionally, the substrate (201) can comprise a target molecule (209) that is attached to the target polynucleotide (208).

In one embodiment, the disclosure provides a substrate comprising a first feature, wherein the first feature comprises (a) a plurality of first capture primers; (b) a plurality of second capture primers; and (c) a target polynucleotide, wherein: (i) the target polynucleotide is double stranded; (ii) the target polynucleotide comprises a second capture primer binding region; (iii) the second capture primer binding region comprises at least one nucleotide mismatch; and (iv) one strand of the second capture primer binding region is a reverse complement of the second capture primer and the other strand of the second capture primer binding region is less than 100% identical to the second capture primer. The second capture primer binding region can contain two or more nucleotide mismatches. The second capture primer binding region can contain three or more nucleotide mismatches. The second capture primer binding region can contain four or more nucleotide mismatches. The target polynucleotide can further comprise one or more additional capture primer binding regions. The target polynucleotide can further comprise a first capture primer binding region that can hybridize to the first capture primer. The first capture primer binding region can hybridize to the first capture primer with 100% complementarity. For example, the first capture primer binding region can contain a 100% nucleotide match to the first capture primer. The first feature can further comprise a plurality of amplicons. The plurality of amplicons can comprise amplicons of the target polynucleotide. The first feature can further comprise a target molecule. The target molecule can be attached to the target polynucleotide. The first feature can further comprise one or more additional target molecules. The one or more additional target molecules can be suspended to a capture primer, target polynucleotide, or amplicon within the feature. Alternatively, or additionally, the one or more additional target molecules are not attached or affixed to the feature. The one or more additional target molecules can be in solution within the feature. The substrate can further comprise one or more additional features. The one or more additional features can comprise a plurality of first capture primers, plurality of second capture primers, target polynucleotide, target molecule, plurality of amplicons, or a combination thereof.

Two or more capture primers can be present in a feature in any ratio. For example, a plurality of first capture primers and a plurality second capture primers can be present in about equal amounts or in any other ratio, e.g., molar ratio. A feature can have a greater than 1.1×, greater than 1.2×, greater than 1.3×, greater than 1.4×, greater than 1.5×, greater than 2.0×, greater than 2.5×, greater than 3.0×, greater than 5.0×, greater than 10×, greater than 15×, greater than 20×, greater than 20×, greater than 25×, greater than 30×, greater than 50×, greater than 100×, greater than 300×, greater than 500×, or greater than 1,000× excess of a first capture primer over a second capture primer. In embodiments using a plurality of features such as, for example, in a microarray the different features can have the same ratio of the two or more capture primers or a different ratio.

A capture primer can include one or more capture regions. A capture primer region can include, for example, a universal capture region, a sequencing primer binding site (SBS), a target-specific capture region, a predetermined cleavage site, such as a restriction site, and a linker region, for example, a linker region separating two or more regions of the capture primer. Some capture primers can include, for example, a universal capture region and a SBS. Other capture primers can include a universal capture region and a target-specific capture region. Still other capture primers can include, for example, a universal capture region, a SBS and a target-specific region. A capture primer can be blocked at the 3'-end (3'-blocked) or unblocked at the 3'-end (3'-unblocked). A primer with a blocked 3'-end can, for example, can be deblocked in an enzymatic or chemical reaction. A capture primer also can include a predetermined (non-random) cleavage site. Exemplary predetermined cleavage sites are described, for example, in U.S. Pat. No. 8,715,966 B2. Cleavage at predetermined sites can occur, for example, as enzymatic cleavage or non-enzymatic cleavage, such as chemical cleavage using methods well known to those skilled in the art. Given the teachings and guidance provided herein, those skilled in the art will understand that a capture primer can contain any number of different regions that are useful in one or more applications.

A universal capture region can be any known or predetermined nucleotide sequence that is included as a common sequence among a plurality of capture primers. Generally, a universal capture region will be sufficiently long to have unique nucleotide sequence among a population of diverse sequences, such as the number of different nucleotide sequences contained in a genome. Those skilled in the art will understand what length of a universal capture region is sufficient to be unique given the sequence diversity of a target population.

A universal capture region can be designed de novo or can be obtained from sources well known in the art. For example, universal capture primers or regions specifically hybridizing with such universal capture primers are available from commercial sources. Two exemplary universal capture primers include, for example, the nucleotide sequences 5'-AATGATACGGCGACCACCGA-3' SEQ ID NO: 1) and 5'-CAAGCAGAAGACGGCATACGA-3' (SEQ ID NO: 2) (P5 and P7 respectively; Illumina, San Diego, Calif.). A region specifically hybridizing with the above capture primers can include, for example, the reverse complement sequence corresponding to 5'-TCGGTG-GTCGCCGTATCATT-3' (SEQ ID NO: 3) or 5'-TCGTAT-GCCGTCTTCTGCTTG-3' (SEQ ID NO: 4) (P5' and P7', respectively, Illumina, San Diego, Calif.).

As with a universal capture region, a SBS can be any known or designed sequence of sufficient length to specifically anneal with a complementary sequencing primer. Exemplary SBSs include, for example, the nucleotide sequences 5'-ACACTCTTTCCCTACACGACGCTCTTC-CGATCT-3' (SEQ ID NO: 5) and 5'-CGGTCTCGGCAT-TCCTGCTGAACCGCTCTTCCGATCT-3' (SEQ ID NO: 6) (SBS3 and SBS8, respectively; Illumina, San Diego, Calif.). A region specifically hybridizing with the above SBSs can include, for example, the reverse complement sequence corresponding to 5'-AGATCG-GAAGAGCGTCGTGTAGGGAAAGAGTGT-3' (SEQ ID NO: 7) and 5'-AGATCGGAAGAGCGGTTCAGCAG-GAATGCCGAGACCG-3' (SEQ ID NO: 8) ("SBS3"'and "SBS8', respectively; Illumina, San Diego, Calif.).

As described previously, a capture primer can have any combination of regions, for example, any combination of the above exemplified P5, P7, SBS3, or SBS8 primer regions or complementary sequences thereto (e.g., P5', P7' SBS3' or SBS8'). Exemplary combinations of the above specific sequences include, for example, combinations such as P5-SBS3, P5-SBS8, P7-SBS8 and P7-SBS3, complementary sequences thereto or combinations thereof.

The first and second capture primers immobilized to a feature can include any capture region or any combination of capture regions. For example, the first capture primer can include a first universal capture region and the second capture primer can include the same universal capture region or a second universal capture region. The first and second capture primers can further include the same or different SBSs. For example, the first capture primer can include a first universal capture primer region and a first SBS and the second capture primer can include a second universal capture region and a second SBS.

For example, in some embodiments, the first capture primer includes a P5 primer nucleotide sequence and the second capture primer includes a P7 primer nucleotide sequence.

In other embodiments, the first capture primer includes a P5 primer nucleotide sequence and a SBS3 primer nucleotide sequence, and the second capture primer includes a P7 primer nucleotide sequence and a SBS8 primer nucleotide sequence. In yet other embodiments, the first capture primer includes a P5 primer nucleotide sequence and a SBS8 primer nucleotide, and the second capture primer includes a P7 primer nucleotide sequence and a SBS3 primer nucleotide sequence.

A capture primer immobilized to a feature on a substrate can be a plurality of capture primers. In some embodiments, a feature can have a single plurality of capture primers such as when a primer extension reaction is desired or when amplification of a target polynucleotide uses the same capture primer binding region at both ends. In other embodiments, a feature can have a plurality of first capture primers and a plurality of second capture primers. Additionally, a feature on a substrate also can have a plurality of capture primers in addition to a plurality of first and second capture primers. For example, in certain embodiments, a feature on a substrate can include a plurality of third, fourth, fifth and/or sixth or more capture primers. The number of pluralities of capture primers to include will depend on the application. For example, in certain embodiments it can be desirable to perform a first bridge amplification using a plurality of first and second capture primers and then perform a second bridge amplification using a plurality of third and fourth capture primers. In such embodiments, the target polynucleotide will have capture primer binding regions for each of the first, second, third and fourth capture primers. Given the teachings and guidance provided herein, those skilled in the art will understand number of pluralities of capture primers and corresponding capture primer binding regions to use given a particular application or desired configuration.

A plurality can be a population of two or more members. In some embodiments, plurality is a population of two or more different polynucleotides or other referenced molecules such as capture primers or target molecules. In other embodiments, a plurality is a population of two or more identical members (e.g., polynucleotides or other referenced molecules such as capture primers, target polynucleotides or target molecules). Alternatively, or additionally, a plurality can be a population of two or more similar members (e.g., polynucleotides or other referenced molecules such as capture primers, target polynucleotides or target molecules). Accordingly, unless expressly stated otherwise, the term "plurality" is used synonymously with population.

In some embodiments, a plurality is 2, 3, 4, 5, 6, 7, 8, 9, 10, 20, 30, 40, 50, 60, 70, 80, 90 or 100 or more different members of the population. In other embodiments, a plurality is 200, 300, 400, 500, 1000, 5000, 10000, 50000, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$ or $1\times10^7$, or more different members.

In some embodiments, a plurality is 2, 3, 4, 5, 6, 7, 8, 9, 10, 20, 30, 40, 50, 60, 70, 80, 90 or 100 or more similar members of the population. In other embodiments, a plurality is 200, 300, 400, 500, 1000, 5000, 10000, 50000, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$ or $1\times10^7$, or more similar members.

In some embodiments, a plurality is 2, 3, 4, 5, 6, 7, 8, 9, 10, 20, 30, 40, 50, 60, 70, 80, 90 or 100 or more identical members of the population. In other embodiments, a plurality is 200, 300, 400, 500, 1000, 5000, 10000, 50000, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$ or $1\times10^7$, or more identical members.

In some embodiments, a plurality is a mixture of different and similar members of the population. In other embodiments, a plurality is a mixture of different and identical members of the population. In some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% or 95% or more of the members of the population in a plurality are identical. In some embodiments, at least 10% of the members of the population in a plurality are identical. In some embodiments, at least 20% of the members of the population in a plurality are identical. In some embodiments, at least 30% of the members of the population in a plurality are identical.

In some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% or 95% or more of the members of the population in a plurality are different. In some embodiments, at least 10% of the members of the population in a plurality are different. In some embodiments, at least 20% of the members of the population in a plurality are different. In some embodiments, at least 30% of the members of the population in a plurality are different.

In some embodiments, at least 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, or 100 or more members of the population in a plurality are at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% or 95% or more homologous. In some embodiments, at least two or more members of the population in a plurality are at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% or 95% or more homologous. In some embodiments, at least three or more members of the population in a plurality are at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% or 95% or more homologous. some embodiments, at least four or more members of the population in a plurality are at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% or 95% or more homologous. In some embodiments, at least five or more members of the population in a plurality are at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% or 95% or more homologous. In some embodiments, at least ten or more members of the population in a plurality are at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% or 95% or more homologous.

In some embodiments, at least 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, or 100 or more members of the population in a plurality are identical. In some embodiments, at least 2 members of the population in a plurality are identical. In some embodiments, at least 3 members of the population in a plurality are identical. In some embodiments, at least 5 members of the population in a plurality are identical. In some embodiments, at least 10 members of the population in a plurality are identical. In some embodiments, at least 20 members of the population in a plurality are identical.

In some embodiments, at least 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, or 100 or more members of the population in a plurality are similar. In some embodiments, at least 2 members of the population in a plurality are similar. In some embodiments, at least 3 members of the population in a plurality are similar. In some embodiments, at least 5 members of the population in a plurality are similar. In some embodiments, at least 10 members of the population in a plurality are similar. In some embodiments, at least 20 members of the population in a plurality are similar.

In some embodiments, at least 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, or 100 or more members of the population in a plurality are different. In some embodiments, at least 2 members of the population in a plurality are different. In some embodiments, at least 3 members of the population in a plurality are different. In some embodiments, at least 5 members of the population in a plurality are different. In some embodiments, at least 10 members of the population in a plurality are different. In some embodiments, at least 20 members of the population in a plurality are different.

A substrate of the disclosure can contain at least one target polynucleotide attached at one end to a capture primer immobilized to a feature. In some embodiments, a substrate of the disclosure will contain one target polynucleotide attached at one end to a capture primer immobilized to a feature. Although described herein with reference to attachment of at least one target polynucleotide or with reference to one target polynucleotide attached at one end to a capture primer immobilized to a feature, it is understood that in other embodiments, a substrate can contain two or more target polynucleotides attached at one end to capture primers immobilized to a feature. In these other embodiments, the number of target polynucleotides can be, for example, 2, 3, 4, 5, 6, 7, 8, 9, 10, 15, 20, 25, 30, 35, 40, 45, 50, 55, 60, 65, 70, 75, 80, 85, 90, 95 or 100 or more different target polynucleotides. Alternatively, the number of target polynucleotides can be, for example, 2, 3, 4, 5, 6, 7, 8, 9, 10, 15, 20, 25, 30, 35, 40, 45, 50, 55, 60, 65, 70, 75, 80, 85, 90, 95 or 100 or more identical target polynucleotides. In other embodiments, the number of target polynucleotides is, for example, 2, 3, 4, 5, 6, 7, 8, 9, 10, 15, 20, 25, 30, 35, 40, 45, 50, 55, 60, 65, 70, 75, 80, 85, 90, 95 or 100 or more similar target polynucleotides.

With reference to at least one target polynucleotide attached at one end to a capture primer immobilized to a feature, the target polynucleotide can be any polynucleotide capable of being amplified in copy number including, for example, DNA, RNA or protein-nucleic acid (PNA). A target polynucleotide can comprise two or more nucleotides. The two or more nucleotides can comprise ribonucleotides, deoxyribonucleotides, locked nucleic acids (LNAs), peptide nucleic acids (PNAs), or any combination thereof. A target polynucleotide can comprise a purine base, pyrimidine base, or both. A target polynucleotide can comprise natural, chemically-modified, biochemically-modified, non-natural, or derivatized nucleotide bases. A target polynucleotide can comprise one or more paired nucleotide bases. A target polynucleotide can be double stranded nucleic acid. In some embodiments, the target polynucleotide can be a double stranded nucleic acid such as double stranded DNA (dsDNA). A target polynucleotide can be a double stranded RNA (dsRNA). A target polynucleotide can be a double stranded DNA/RNA hybrid. A target polynucleotide can comprise one or more unpaired nucleotide bases. A target polynucleotide can be single-stranded. In other embodiments the target polynucleotide can be a single stranded nucleic acid such as single stranded DNA (ssDNA). A target polynucleotide can be a single stranded RNA. A target polynucleotide can comprise a mixture of paired and unpaired nucleotide bases.

For placement of a single molecule on a feature a target polynucleotide acts as a tether or anchor for the target molecule to the feature. Accordingly, the target polynucleotide can be any sequence of a desired length. In some embodiments where a plurality of target molecules are each anchored to a plurality of different features the plurality of target polynucleotides can have the same sequence or different sequences. In other embodiments, some or all of the plurality of target polynucleotides each anchoring a plurality of target molecules to different features can have different sequences. Thus, a target polynucleotide can be any desired sequence or mixture of sequences. Given the teachings and guidance provided herein those skilled in the art will understand whether to use the same target polynucleotide sequence or different target polynucleotide sequences with immobilizing a plurality of target molecules to a plurality of different features.

A target polynucleotide can comprise one or more target polynucleotide regions. A target polynucleotide region can comprise a capture primer binding region, target region, primer binding region, barcode region, linker region, or adapter region. For example, a target polynucleotide can comprise a target polynucleotide region comprising a capture primer binding region. A target polynucleotide can comprise a target polynucleotide region comprising a first capture primer binding region. A target polynucleotide can comprise a target polynucleotide region comprising a second capture primer binding region. Alternatively, or additionally a target polynucleotide can comprise a target polynucleotide region comprising a target region. A target polynucleotide can comprise a target polynucleotide region comprising a primer binding region. A target polynucleotide can comprise a target polynucleotide region comprising a barcode region. A target polynucleotide can comprise a target polynucleotide region comprising a linker region. Alternatively, or additionally, a target polynucleotide can comprise a target polynucleotide region comprising an adapter region.

A target polynucleotide can comprise a plurality of target polynucleotide regions. A target polynucleotide can comprise 1, 2, 3, 4, 5, 6, 7, 8, 9, or 10 or more target polynucleotide regions. A target polynucleotide can comprise two or more target polynucleotide regions. A target polynucleotide can comprise three or more target polynucleotide regions. A target polynucleotide can comprise four or more target polynucleotide regions. A target polynucleotide can comprise five or more target polynucleotide regions. A target polynucleotide can comprise six or more target polynucleotide regions. A target polynucleotide can comprise a plurality of target polynucleotide regions comprising one or more first capture primer binding regions, second capture primer binding regions, target regions, primer binding regions, barcode regions, linker regions, adapter regions, or any combination thereof. A target polynucleotide can comprise a plurality of target polynucleotide regions comprising two or more first capture primer binding regions, second capture primer binding regions, target regions, primer binding regions, barcode regions, linker regions, adapter regions, or any combination thereof. A target polynucleotide can comprise a plurality of target polynucleotide regions comprising three or more first capture primer binding regions, second capture primer binding regions, target regions, primer binding regions, barcode regions, linker regions, adapter regions, or any combination thereof.

Figure 3:
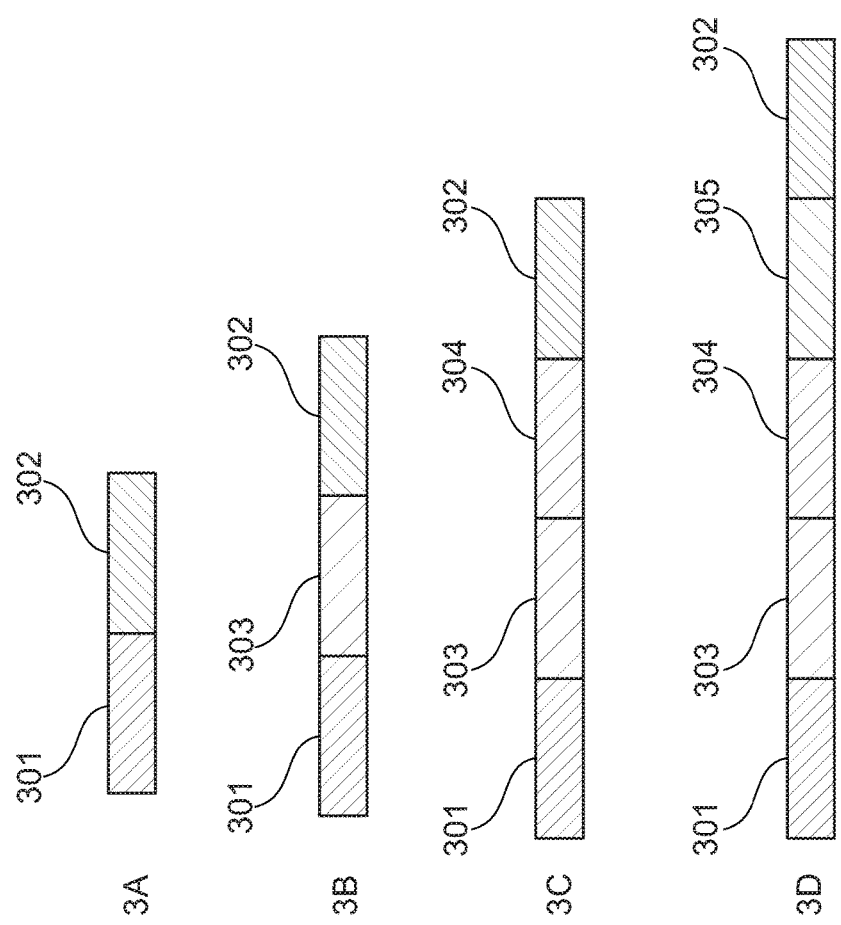
FIG. 3A-D show exemplary target polynucleotides.

Exemplary target polynucleotides comprising two or more target polynucleotide regions are depicted in FIG. 3A-D. As shown in FIG. 3A, a target polynucleotide can comprise two or more target polynucleotide regions (301, 302). A first target polynucleotide region (301) can be a first capture primer binding region. A second target polynucleotide region (302) can be a second capture primer binding region. As shown in FIG. 3B, a target polynucleotide can comprise three or more target polynucleotide regions (301, 302, 303). A first target polynucleotide region (301) can be a first capture primer binding region. A second target polynucleotide region (302) can be a second capture primer binding region. A third target polynucleotide region (303) can be a target region. As shown in FIG. 3C, a target polynucleotide can comprise four or more target polynucleotide regions (301, 302, 303, 304). A first target polynucleotide region (301) can be a first capture primer binding region. A second target polynucleotide region (302) can be a second capture primer binding region. A third target polynucleotide region (303) can be a target region. A fourth target polynucleotide region (304) can be a primer binding region. As shown in FIG. 3D, a target polynucleotide can comprise five or more target polynucleotide regions (301, 302, 303, 304, 305). A first target polynucleotide region (301) can be a first capture primer binding region. A second target polynucleotide region (302) can be a second capture primer binding region. A third target polynucleotide region (303) can be a target region. A fourth target polynucleotide region (304) can be a primer binding region. A fifth target polynucleotide region (305) can be a barcode region. Alternatively, or additionally, a target polynucleotide region can be a linker region. Alternatively, or additionally, a target polynucleotide region can be an adapter region.

A target polynucleotide or a target polynucleotide region (target polynucleotide or region thereof) including, for example, a target region, a capture primer binding region and/or other region described herein or well known to those skilled in the art can comprise two or more nucleotides. A target polynucleotide or region thereof can comprise 2, 3, 4, 5, 6, 7, 8, 9, 10, 11, 12, 13, 14, 15, 16, 17, 18, 19, or 20 or more nucleotides. A target polynucleotide can comprise 25, 30, 35, 40, 45, 50, 55, 70, 65, 70, 75, 80, 85, 90, 95, 100 or more nucleotides. A target polynucleotide or region thereof can comprise 150, 200, 250, 300, 350, 400, 450, 500, 550, 700, 650, 700, 750, 800, 850, 900, 950, 1000 or more nucleotides. A target polynucleotide or region thereof can comprise 1100, 1200, 1300, 1400, 1500, 2000, 2500, 3000, 3500, 4000, 4500, 5000, 5500, 7000, 6500, 7000, 7500, 8000, 8500, 9000, 9500, 10000 or more nucleotides. A target polynucleotide or region thereof can comprise 100 or more nucleotides. A target polynucleotide or region thereof can comprise 300 or more nucleotides. A target polynucleotide or region thereof can comprise 400 or more nucleotides. A target polynucleotide or region thereof can comprise 500 or more nucleotides. A target polynucleotide or region thereof can comprise 600 or more nucleotides.

A target polynucleotide or region thereof can comprise between 10 to 25, 26 to 50, 51 to 100, 101 to 200, 201 to 300, 301 to 400, 401 to 500, 501 to 600, 601 to 700, 701 to 800, 801 to 900, or 901 to 1000 nucleotides. A target polynucleotide or region thereof can comprise between about 5 to 2000, 5 to 1500, 5 to 1000, 5 to 800, 5 to 600, 5 to 400, 5 to 200, 5 to 100, or 5 to 50 nucleotides. A target polynucleotide or region thereof can comprise between about 10 to 2000, 10 to 1500, 10 to 1000, 10 to 800, 10 to 600, 10 to 400, 10 to 200, 10 to 100, or 10 to 50 nucleotides. A target polynucleotide or region thereof can comprise between about 20 to 2000, 20 to 1500, 20 to 1000, 20 to 800, 20 to 600, 20 to 400, 20 to 200, 20 to 100, or 20 to 50 nucleotides.

A target polynucleotide or region thereof can comprise less than about 5000, 4500, 4000, 3500, 3000, 2500, 2000, 1500, or 1000 or fewer nucleotides. A target polynucleotide or region thereof can comprise less than about 950, 900, 850, 800, 750, 700, 650, 600, 550, 500, 450, 400, 350, 300, 250, 200, 150, or 100 or fewer nucleotides. A target polynucleotide or region thereof can comprise less than about 95, 90, 85, 80, 75, 70, 65, 60, 55, 50, 45, 40, 35, 30, 25, 20, 15, or 10 or fewer nucleotides.

A target polynucleotide or region thereof can comprise a double-stranded polynucleotide. A target polynucleotide or region thereof can comprise one or more base pairs. A target polynucleotide can comprise 2, 3, 4, 5, 6, 7, 8, 9, 10, 11, 12, 13, 14, 15, 16, 17, 18, 19, or 20 or more base pairs. A target polynucleotide or region thereof can comprise 25, 30, 35, 40, 45, 50, 55, 70, 65, 70, 75, 80, 85, 90, 95, 100 or more base pairs. A target polynucleotide or region thereof can comprise 150, 200, 250, 300, 350, 400, 450, 500, 550, 700, 650, 700, 750, 800, 850, 900, 950, 1000 or more base pairs. A target polynucleotide or region thereof can comprise 1100, 1200, 1300, 1400, 1500, 2000, 2500, 3000, 3500, 4000, 4500, 5000, 5500, 7000, 6500, 7000, 7500, 8000, 8500, 9000, 9500, 10000 or more base pairs. A target polynucleotide or region thereof can comprise 100 or more base pairs. A target polynucleotide or region thereof can comprise 300 or more base pairs. A target polynucleotide or region thereof can comprise 400 or more base pairs. A target polynucleotide or region thereof can comprise 500 or more base pairs. A target polynucleotide can comprise 600 or more base pairs.

A target polynucleotide or region thereof can comprise between 10 to 25, 26 to 50, 51 to 100, 101 to 200, 201 to 300, 301 to 400, 401 to 500, 501 to 600, 601 to 700, 701 to 800, 801 to 900, or 901 to 1000 base pairs. A target polynucleotide or region thereof can comprise between about 5 to 2000, 5 to 1500, 5 to 1000, 5 to 800, 5 to 600, 5 to 400, 5 to 200, 5 to 100, or 5 to 50 base pairs. A target polynucleotide or region thereof can comprise between about 10 to 2000, 10 to 1500, 10 to 1000, 10 to 800, 10 to 600, 10 to 400, 10 to 200, 10 to 100, or 10 to 50 base pairs. A target polynucleotide or region thereof can comprise between about 20 to 2000, 20 to 1500, 20 to 1000, 20 to 800, 20 to 600, 20 to 400, 20 to 200, 20 to 100, or 20 to 50 base pairs.

A target polynucleotide or region thereof can comprise less than about 5000, 4500, 4000, 3500, 3000, 2500, 2000, 1500, or 1000 or fewer base pairs. A target polynucleotide or region thereof can comprise less than about 950, 900, 850, 800, 750, 700, 650, 600, 550, 500, 450, 400, 350, 300, 250, 200, 150, or 100 or fewer base pairs. A target polynucleotide or region thereof can comprise less than about 95, 90, 85, 80, 75, 70, 65, 60, 55, 50, 45, 40, 35, 30, 25, 20, 15, or 10 or fewer base pairs.

A double-stranded target polynucleotide or region thereof can comprise 1, 2, 3, 4, 5, 6, 7, 8, 9, 10, 11, 12, 13, 14, 15, 16, 17, 18, 19, or 20 or more mismatches. A target polynucleotide or region thereof that is double-stranded can comprise one or more mismatches. A double-stranded target polynucleotide or region thereof can comprise two or more mismatches. A double-stranded target polynucleotide or region thereof can comprise three or more mismatches. A double-stranded target polynucleotide or region thereof can comprise four or more mismatches. A double-stranded target polynucleotide or region thereof can comprise five or more mismatches.

A double-stranded target polynucleotide or region thereof can comprise less than 10, 9, 8, 7, 6, 5, 4, 3, 2, or 1 mismatches. A double-stranded target polynucleotide or region thereof can comprise five or fewer mismatches. A double-stranded target polynucleotide or region thereof can comprise four or fewer mismatches. A double-stranded target polynucleotide or region thereof can comprise three or fewer mismatches. A double-stranded target polynucleotide or region thereof can comprise two or fewer mismatches. A double-stranded target polynucleotide or region thereof can comprise one or fewer mismatches.

As exemplified previously, a target polynucleotide can comprise one or more regions comprising one or more capture primer binding regions. Generally, a capture primer binding region is complementary to a capture primer. A target polynucleotide region can comprise a capture primer binding region on a 5' end. A target polynucleotide region can comprise a capture primer binding region on a 3' end. A target polynucleotide region can comprise a first capture primer binding region on a 5' end of the target region and a second capture primer binding region on a 3' end of the target region. Alternatively, or additionally, a target polynucleotide region comprising a capture primer binding region can be located at an internal region of the target polynucleotide.

A target polynucleotide can comprise two or more capture primer binding regions. A target polynucleotide can comprise three or more capture primer binding regions. A target polynucleotide can comprise four or more capture primer binding regions. The two or more capture primer binding regions can be the same. Alternatively, or additionally, the two or more capture primer binding regions can be different. The two or more capture primer binding regions can be adjacent to each other on the target polynucleotide. Alternatively, or additionally, the two or more capture primer binding regions may be nonadjacent to each other on the polynucleotide.

As with the corresponding capture primers, a capture primer binding region can include one or more capture primer binding regions. A capture primer binding region can include, for example, a universal capture primer binding region, a sequencing primer binding site (SBS), a target-specific capture primer binding region, a predetermined cleavage site, such as a restriction site, and a linker region, for example, a linker region separating two or more regions of the capture primer binding region. Some capture primer binding regions can include, for example, a universal capture primer binding region and a SBS. Other capture primer binding regions can include a universal capture primer binding region and a target-specific capture primer binding region. Still other capture primer binding regions can include, for example, a universal capture primer binding region, a SBS and a target-specific capture primer binding region. A capture primer binding region can be blocked or unblocked at either the 3' or 5' end. Given the teachings and guidance provided herein, those skilled in the art will understand that a capture primer binding region can contain any number of different regions that are useful in one or more applications.

For example, the universal capture primers exemplified previously also can be used as universal capture primer binding regions as can other capture primer regions exemplified herein or well known in the art. In reference to the previously described universal capture primers, the exemplified P5, P7 P5' and/or P7' sequences can be used as universal capture primer binding regions to anneal to complementary capture primers (e.g., P5', P7', P5 and/or P7, respectively). Similarly, the SBS sequences exemplified previously or other sequences designed or known in the art can be included as a region in a capture primer region. In one embodiment, the exemplary SBS sequences SBS3, SBS8, SBS3' and/or SBS8' can be included, for example.

For example, a plurality of target polynucleotide binding regions can have any combination of capture primer binding regions, for example, any combination of the above exemplified P5, P7, SBS3, or SBS8 primer regions or complementary sequences thereto (e.g., P5', P7' SBS3' or SBS8'). Exemplary combinations of the above specific sequences include, for example, combinations such as P5-SBS3, P5-SBS8, P7-SBS8 and P7-SBS3, complementary sequences thereto or combinations thereof.

Figure 4:
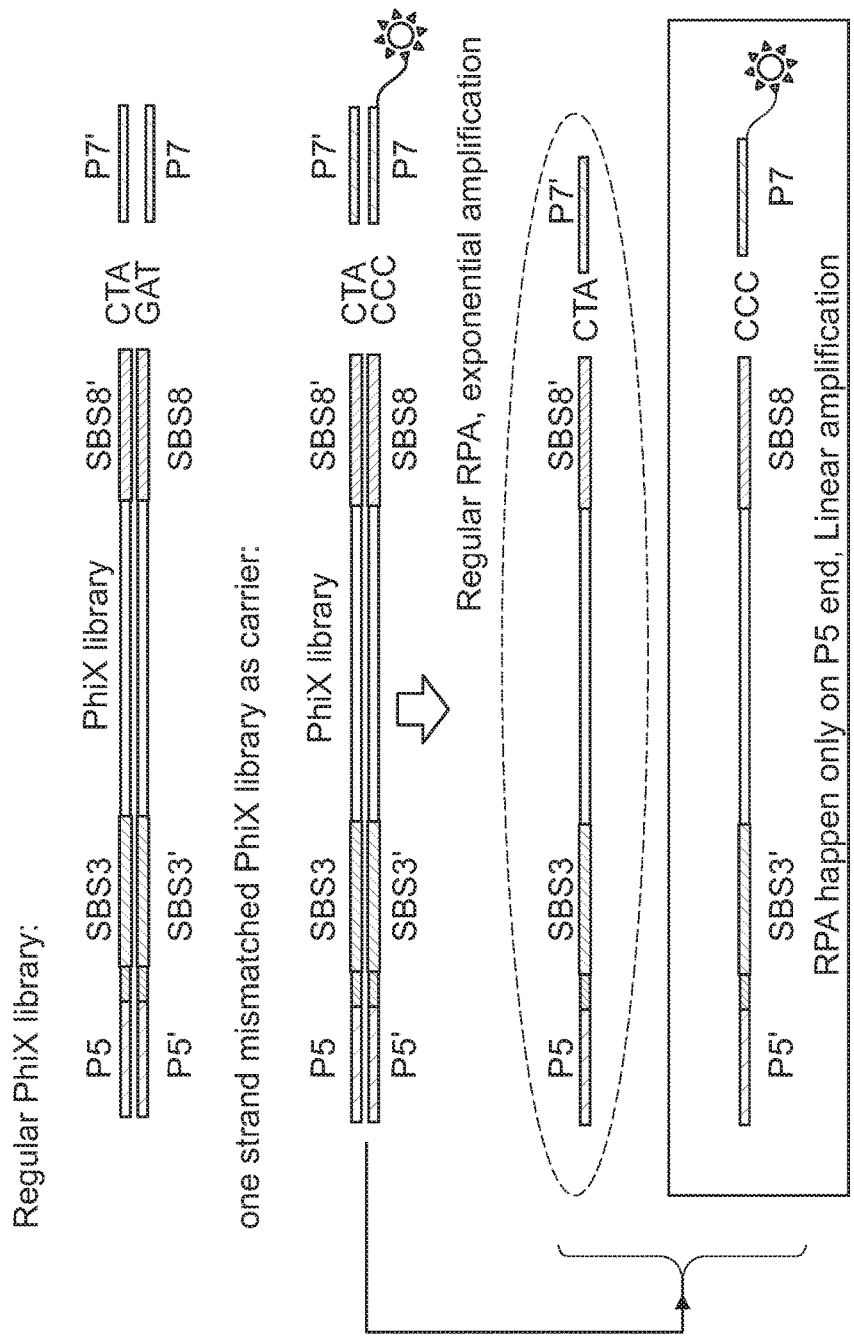
FIG. 4 illustrates a design of a capture primer binding region on a target polynucleotide that can be employed to amplify the strand attached to a target molecule from a capture primer binding region at the distal end while exponentially amplifying the amplicons produced therefrom.

As shown in FIG. 4, one exemplary combination for a target region flanked by capture primer binding regions is a P5-SBS3 capture primer binding region on a first end of the target polynucleotide and P7'-SBS8' capture primer binding region on a second end. The corresponding complementary strand includes a P5'-SBS3' capture primer binding region on the first end and a P7-SBS8 capture primer binding region on the second end.

A capture primer binding region can comprise 5, 6, 7, 8, 9, 10, 11, 12, 13, 14, 15, 16, 17, 18, 19, 20, 21, 22, 23, 24, 25, 26, 27, 28, 29, or 30 or more nucleotides. A capture primer binding region can comprise 35, 40, 45, 50, 55, 60, 65, 70, 75, 80, 85, 90, 95, or 100 or more nucleotides. A capture primer binding region can comprise 5 or more nucleotides. A capture primer binding region can comprise 10 or more nucleotides. A capture primer binding region can comprise 15 or more nucleotides. A capture primer binding region can comprise 20 or more nucleotides. A capture primer binding region can comprise 25 or more nucleotides.

A capture primer binding region can comprise 400, 375, 350, 325, 300, 275, 250, 225, 200, 190, 180, 170, 160, 150, 140, 130, 120, 110, 100 or few nucleotides. A capture primer binding region can comprise 300 or fewer nucleotides. A capture primer binding region can comprise 200 or fewer nucleotides. A capture primer binding region can comprise 100 or fewer nucleotides. A capture primer binding region can comprise 50 or fewer nucleotides. A capture primer binding region can comprise 40 or fewer nucleotides. A capture primer binding region can comprise 30 or fewer nucleotides.

A capture primer binding region of the target polynucleotide can be 100% complementary to a capture primer. A capture primer binding region of the target polynucleotide can be at least 60%, 65%, 70%, 75%, 77%, 80%, 82%, 85%, 87%, 90%, 92%, 95%, or 97% or more complementary to a capture primer. A capture primer binding region of the target polynucleotide can be 80% complementary to a capture primer. A capture primer binding region of the target polynucleotide can be 85% complementary to a capture primer. A capture primer binding region of the target polynucleotide can be at least 90% complementary to a capture primer. A capture primer binding region of the target polynucleotide can be at least 95% complementary to a capture primer.

A capture primer binding region of the target polynucleotide can comprise 1, 2, 3, 4, 5, 6, 7, 8, 9, or 10 or more nucleotide mismatches to a capture primer. A capture primer binding region of the target polynucleotide can comprise one or more nucleotide mismatches to a capture primer. A capture primer binding region of the target polynucleotide can comprise two or more nucleotide mismatches to a capture primer. A capture primer binding region of the target polynucleotide can comprise three or more nucleotide mismatches to a capture primer. A capture primer binding region of the target polynucleotide can comprise four or more nucleotide mismatches to a capture primer.

A target polynucleotide can comprise one or more target regions. A target polynucleotide can have a target region located at an internal region of the target polynucleotide. For example, the target region can be flanked at its 5' and 3' ends by a capture primer binding region or other region. Alternatively, or additionally, a target region can be located, for example, on a 5' end of the target polynucleotide. A target polynucleotide can include a capture primer binding region on a 3' end, a 5' end or both, as exemplified above, of the target polynucleotide. A target polynucleotide can comprise a first target region on a 5' end of the target polynucleotide and a second target region on a 3' end of the target polynucleotide. A target region can be flanked by one or more capture primer binding regions on either or both ends.

A target polynucleotide can comprise two or more target regions. A target polynucleotide can comprise three or more target regions. A target polynucleotide can comprise four or more target regions. The two or more target regions can be the same. Alternatively, or additionally, the two or more target regions can be different. The two or more target regions can be adjacent to each other on the target polynucleotide. Alternatively, or additionally, the two or more target regions can be nonadjacent to each other on the target polynucleotide.

The size or length of the target region can be any of the lengths exemplified above with respect to a target polynucleotide or a target polynucleotide region. Exemplary lengths include 5, 6, 7, 8, 9, 10, 11, 12, 13, 14, 15, 16, 17, 18, 19, 20, 21, 22, 23, 24, 25, 26, 27, 28, 29, or 30 or more nucleotides. A target region can comprise 35, 40, 45, 50, 55, 60, 65, 70, 75, 80, 85, 90, 95, or 100 or more nucleotides. A target region can comprise 150, 200, 250, 300, 350, 400, 450, 500, 550, 600, 650, 700, 750, 800, 850, 900, 950, or 100 or more nucleotides. A target region can comprise 5 or more nucleotides. A target region can comprise 10 or more, 20 or more, 50 or more, 100 or more, 200 or more or 400 or more nucleotides Other exemplary lengths include, for example, 1000, 950, 900, 850, 800, 750, 700, 650, 600, 550, 500, 450, 400, 375, 350, 325, 300, 275, 250, 225, 200, 190, 180, 170, 160, 150, 140, 130, 120, 110, 100 or few nucleotides. Still other exemplary lengths include, for example, 700 or fewer, 500 or fewer, 300 or fewer, 200 or fewer, 100 or fewer or 50 or fewer nucleotides.

A substrate of the disclosure can contain at least one target molecule. The at least one target molecule can be attached to a target polynucleotide. The at least one target molecule can be attached to a target polynucleotide that is attached to a capture primer. The at least one target molecule can be attached to a target polynucleotide that is attached to a capture primer immobilized to a feature. Although described herein with reference to at least one target molecule, with reference to at least one target molecule attached to a target polynucleotide, with reference to at least one target molecule attached to a target polynucleotide attached to a capture primer, or with reference to at least one target molecule attached to a target polynucleotide attached to a capture primer immobilized to a feature, it is understood that in other embodiments, a substrate can contain a plurality of two or more target molecules in each of the referenced situations. As exemplified further below, the plurality of target molecules can be immobilized individually to different features on a substrate. Alternatively, a plurality of target molecules can be immobilized to the same feature on a substrate. In the embodiments where a plurality of target molecules are individually immobilized to different features the plurality of target molecules can be the same target molecule or different types or species of target molecules as exemplified above and below. In these embodiments, the number of target molecules within a plurality can be, for example, 2, 3, 4, 5, 6, 7, 8, 9, 10, 15, 20, 25, 30, 35, 40, 45, 50, 55, 60, 65, 70, 75, 80, 85, 90, 95, 100, 250, 500, 1,000, 5,000, 10,000 or more different, identical and/or similar target molecules.

For example, a plurality of target molecules can comprise two or more identical target molecules. In this embodiment, both the first and second or more target molecules can be, for example, a specific polypeptide such as an MspA nanopore. Alternatively, or additionally, a plurality of target molecules can comprise two or more different target molecules. For example, a first target molecule of the plurality of target molecules can be an enzyme and a second target molecule of the plurality of target molecules can be a polynucleotide. The plurality of target molecules can comprise three or more different target molecules. For example, a first target molecule of the plurality of target molecules can be an enzyme, a second target molecule of the plurality of target molecules can be a polynucleotide, and a third target molecule of the plurality of target molecules can be a small organic compound. Alternatively, or additionally, the plurality of target molecules can comprise two or more similar target molecules. The two or more similar target molecules can be of the same type of molecule. For example, a first target molecule can be an MspA nanopore and a second target molecule can be a NaIP nanopore. In this instance, the first and second target molecules are of the same type of molecules (e.g., nanopores). The two or more similar target molecules can be homologues or variants. For example, a first target molecule can be a human version of a polypeptide and a second target molecule can be a mouse version of a polypeptide. Variants can include polypeptides encoded by different alleles or obtained by site-specific mutagenesis, directed evolution or the like. The two or more similar target molecules can be alternative splice variants of the same protein. For example, a first target molecule can be a full length version of a polypeptide and a second target molecule can be a truncated version of the polypeptide. The two or more similar target molecules can be chemical analogs or derivatives. For example, a first target molecule can be a compound X and the second target molecule can be a derivative of compound X. In one exemplary embodiment, the plurality of similar target molecules can be a library of enzyme variants. Exemplary target molecules are described further below.

In some embodiments, at least one target molecule or a plurality of target molecules can be attached to the substrate and/or attached to a feature on the substrate. At least one target molecule or a plurality of target molecules can be attached to a capture primer or a plurality of capture primers, respectively, immobilized to a feature on the substrate. At least one target molecule or a plurality of target molecules can be attached to a target polynucleotide that is attached to a capture primer or plurality thereof, respectively, immobilized to a feature on the substrate. The attachment can be covalent or noncovalent attachment of the target molecule to any of the regions or components described above. With reference to at least one target molecule, for example, at least one target molecule can be covalently attached to the substrate and/or a feature on the substrate. At least one target molecule can be covalently attached to a capture primer immobilized to a feature on the substrate. At least one target molecule can be covalently attached to a target polynucleotide that is covalently attached to a capture primer immobilized to a feature on the substrate. An exemplary embodiment for covalent attachment of a target polynucleotide to a capture primer through a covalent phosphodiester bond is described further below in reference to methods of placing at least one target molecule on a feature of a substrate. Additionally, for example, at least one target molecule can be noncovalently attached to the substrate and/or to a feature on the substrate. At least one target molecule can be noncovalently attached to a capture primer immobilized to a feature on the substrate. At least one target molecule can be noncovalently attached to a target polynucleotide that is noncovalently attached to a capture primer immobilized to a feature on the substrate. Methods for covalent and noncovalent attachment of the polynucleotides and target molecules to substrates and to each other are well known in the art.

In addition to at least one target molecule immobilized through a configuration described above, a feature or a plurality of features on a substrate also can include a plurality of amplicons of the target polynucleotide. The amplicons can be complementary to the target polynucleotide. In embodiments where a target polynucleotide or a target polynucleotide region contains one or more nucleotide mismatches, the amplicons can be complementary to the target polynucleotide except for the one or more nucleotide mismatches. Similarly, in this embodiment, a double stranded amplicon of the target polynucleotide can have one strand complementary to the target polynucleotide except for the one or more nucleotide mismatches and the other strand identical in sequence to the target polynucleotide except for the one or more nucleotide mismatches. In other embodiments the amplicons can be a plurality of the different amplicon species exemplified above. The plurality of amplicons can minimally fill a feature, partially fill a feature or fill to capacity a feature on a substrate. Accordingly, the amplicon density can be low, medium or high. Target polynucleotide design, methods to generate such amplicons and methods to control density are described further below with reference to methods of placing at least one target molecule on a feature of a substrate. The density of amplicons can be about 10 to 100 in a feature with a size of about 100 nm), or about 100 to 10000 in feature with size of about 100 nm to 1 um The density of amplicons can be about 10 to 100, in a feature with a size less than about 100 nm. The density of amplicons can be about 10 to 95, in a feature with a size less than about 100 nm. The density of amplicons can be about 10 to 90, in a feature with a size less than about 100 nm. The density of amplicons can be about 10 to 85, in a feature with a size less than about 100 nm. The density of amplicons can be about 10 to 80, in a feature with a size less than about 100 nm. The density of amplicons can be about 10 to 75, in a feature with a size less than about 100 nm. The density of amplicons can be about 10 to 70, in a feature with a size less than about 100 nm. The density of amplicons can be about 10 to 65, in a feature with a size less than about 100 nm. The density of amplicons can be about 10 to 60, in a feature with a size less than about 100 nm. The density of amplicons can be about 10 to 55, in a feature with a size less than about 100 nm. The density of amplicons can be about 10 to 50, in a feature with a size less than about 100 nm. The density of amplicons can be about 10 to 45, in a feature with a size less than about 100 nm. The density of amplicons can be about 10 to 40, in a feature with a size less than about 100 nm. The density of amplicons can be about 10 to 35, in a feature with a size less than about 100 nm. The density of amplicons can be about 10 to 30, in a feature with a size less than about 100 nm. The density of amplicons can be about 10 to 25, in a feature with a size less than about 100 nm. The density of amplicons can be about 10 to 20 in a feature with a size less than about 100 nm. The density of amplicons can be about 10 to 15, in a feature with a size less than about 100 nm.

The density of amplicons can be greater than about 10, 20, 30, 40, 50, 60, 70, 80, 90, or 100 in a feature with a size less than about 100 nm.

The density of amplicons can be about 100 to 10000, in a feature with a size of about 100 nm to 1 μm. The density of amplicons can be about 100 to 9000, in a feature with a size about 100 nm to 1 μm. The density of amplicons can be about 100 to 8000, in a feature with a size about 100 nm to 1 μm. The density of amplicons can be about 100 to 7000, in a feature with a size of about 100 nm to 1 μm. The density of amplicons can be about 100 to 6000, in a feature with a size of about 100 nm to 1 μm. The density of amplicons can be about 100 to 5000, in a feature with a size of about 100 nm to 1 μm. The density of amplicons can be about 100 to 4000, in a feature with a size of about 100 nm to 1 μm. The density of amplicons can be about 100 to 3000, in a feature with a size of about 100 nm to 1 μm. The density of amplicons can be about 100 to 2000, in a feature with a size of about 100 nm to 1 μm. The density of amplicons can be about 100 to 1000, in a feature with a size of about 100 nm to 1 μm. The density of amplicons can be about 100 to 900, in a feature with a size of about 100 nm to 1 μm. The density of amplicons can be about 100 to 800, in a feature with a size of about 100 nm to 1 μm. The density of amplicons can be about 100 to 700, in a feature with a size of about 100 nm to 1 μm. The density of amplicons can be about 100 to 600, in a feature with a size of about 100 nm to 1 μm. The density of amplicons can be about 100 to 500, in a feature with a size of about 100 nm to 1 μm. The density of amplicons can be about 100 to 400, in a feature with a size of about 100 nm to 1 μm. The density of amplicons can be about 100 to 300, in a feature with a size of about 100 nm to 1 μm. The density of amplicons can be about 100 to 200, in a feature with a size of about 100 nm to 1 μm.

A target molecule applicable for single molecular placement on a substrate of the disclosure and for use in a method of the disclosure can be any desired molecule. Exemplary categories of target molecules include, for example, a polypeptide, polynucleotide, carbohydrate, amino acid, nucleotide, monosaccharide, hapten, ligand, antigen, analyte, ion channel, small molecule organic compound or inorganic compound. Exemplary species for each of the above categories are described further below.

A target molecule of the disclosure can comprise a polypeptide. A polypeptide can comprise one or more amino acids. A polypeptide can comprise 2, 3, 4, 5, 6, 7, 8, 9, 10, 11, 12, 13, 14, 15, 16, 17, 18, 19, or 20 or more amino acids. A polypeptide can comprise 20, 30, 40, 50, 60, 70, 80, 90, 100, 110, 120, 130, 140, 150, 160, 170, 180, 190, or 200 or more amino acids. A polypeptide can comprise 200, 300, 400, 500, 600, 700, 800, 900, 1000, 1100, 1200, 1300, 1400, 1500, 1600, 1700, 1800, 1900, or 2000 or more amino acids. The amino acid can be a natural amino acid. The amino acid can be an unnatural amino acid. The amino acid can be a D-amino acid. The amino acid can be an L-amino acid. The one or more amino acids can comprise one or more natural amino acids, unnatural amino acids, D-amino acids, L-amino acids, or a combination thereof. Examples of amino acids include, but are not limited to, p-acetylphenalalanine, m-acetylphenalalanine, alanine, β-alanine, γ-aminoburyic acid (GABA), aminoisobutyric acid, δ-aminolevulinic acid, 4-aminobenzoic acid (PABA), arginine, asparagine, aspartic acid, p-benxoyl-1-phenylalanine, citrulline, cystathionine, cysteine, cystine, diaminopimelic acid, Djenkolic acid, glutamic acid, glutamine, glycine, histidine, isoleucine, lanthionine, leucine, lysine, methionine, ornithine, phenylalanine, phenyl selenidylalanine, proline, selenocysteine, serine, threonine, tryptophan, tyrosine, and valine. Examples of polypeptides include, but are not limited to, ribosomal peptide, nonribosomal peptide, peptone, peptide fragment, or any combination thereof. Polypeptides of the disclosure can be recombinant, synthetic or naturally occurring.

A target molecule of the disclosure can comprise a ribosomal polypeptide. Generally, a ribosomal peptide can be a peptide that is synthesized by translation of mRNA. The ribosomal protein can undergo one or more posttranslational modifications. Examples of posttranslational modifications include, but are not limited to, phosphorylation, hydroxylation, sulfonation, palmitoylatation, glycosylation, ubiquitination, sumoylation, and disulfide formation. Examples of ribosomal peptides include, but are not limited to, enzymes, receptors, antibodies, transcription factors, hormones, ligands, antigens, and haptens.

A target molecule of the disclosure can comprise a non-ribosomal peptide. Generally, a nonribosomal peptide can be a peptide that is assembled by enzymes that are specific to each peptide rather than by the ribosome. The nonribosomal peptide can have a cyclic and/or branched structure. The nonribosomal peptide can contain one or more non-proteinogenic amino acids such as D-amino acids. The nonribosomal polypeptide can comprise modifications such as N-methyl and N-formyl groups. The nonribosomal polypeptide can be glycosylated, acylated, halogenated, or hydroxylated. The nonribosomal polypeptide can undergo dehydration of one or more serines, resulting in dehydroalanine. The nonribosomal peptide can be a multimer. The nonribosomal peptide can be a dimer or trimer. Examples of nonribosomal peptides include, but are not limited to, toxins, siderophores, pigments, antibiotics, antibiotic precursors, cytostatics, and immunosuppressants.

A target molecule of the disclosure can comprise one or more polypeptides that assemble into a nanopore. A nanopore can be selected from the group consisting of *Mycobacterium smegmatis* porin A (MspA), outer membrane phospholipase A (OmpA), OmpC, OmpF, OmpG, *Neisseria* autotransporter lipoprotein (NaIP), WZA, ClyA toxin, α-hemolysin, anthrax toxin, gramicidin A, maltoporin, PhoE, Tsx, F-pilus, SP1, mitochondrial porin (VDAC), Tom40, leukocidins and DNA origami nanopore.

A target molecule of the disclosure can comprise an antibiotic. An antibiotic can be a penicillin, cephalosporin, polymyxin, rifamycin, lipiarmycin, quinolone, sulfonamide, macrolide, aminoglycoside, cyclic lipopeptide, glycylcycline, oxazolidinone or a microcin. Examples of antibiotics include, but are not limited to, actinomycin, bacitracin, calcium dependent antibiotic, daptomycin, gramicidin, tyrocidine, vancomycin, zwittermicin A, plazomicin, eravacycline, brilacidin, avibactam, azithromycin, clarithromycin, erythromycin, carbomycin, josamycin, kitasamycin, midecamycin, oleandomycin, solithromycin, spiramycin, troleandomycin, tylosin, roxithromycin, cethromycin, ansamycin, carbomycin, tylosin, and telithromycin.

A target molecule of the disclosure can comprise a toxin. A toxin can be a hemotoxin. A hemotoxin can cause destruction of red blood cells. The toxin can be a phototoxin. A phototoxin can cause photosensitivity. The toxin can be an exotoxin. An exotoxin can be excreted by an organism or cell. The toxin can be an endotoxin. An endotoxin can be a toxin that is released when a cell or organism is lysed. The toxin can be a biotoxin. A biotoxin can be a toxin that has a biological origin. For example, a toxin that is produced from a fungus can be referred to as a biotoxin. The toxin can be a necrotoxin. A necrotoxin can cause necrosis. The toxin can be a neurotoxin. A neurotoxin can affect the nervous system of animals. The toxin can be a cytotoxin. A cytotoxin can be toxic at the level of individual cells. The toxin can be a mycotoxin. Examples of mycotoxins include aflatoxins, ochratoxins, citrinin, ergot alkaloids, patulin, and *fusarium*. Examples of toxins include, but are not limited to, microcystins, nodularins, anatoxin-a, anatoxin-a(S), cylindrospermopsins, lyngbyatoxin-a, saxitoxin, aplysiatoxin, cyanotoxins, HC-toxin, AM-toxin, victorin, ricin, apitoxin, fumonisins, trichothecenes, zearalenone, beauvercin, enniatins, butenolide, equisetin, tetanus toxin, botulinum toxin, tetrodotoxin, and fusarins.

A target molecule of the disclosure can comprise a hormone. A hormone can be an amine hormone, peptide hormone, protein hormone, steroid hormone, or a combination thereof. An amine hormone can comprise one or more amino acids with one or more modified groups. For example, a carboxyl of an amino acid can be replaced with a chemical group such as a benzene ring. A peptide hormone can comprise a short chain of linked amino acids. A protein hormone can comprise a long chain of linked amino acids. A steroid hormone can be derived from a lipid cholesterol. Examples of hormones include, but are not limited to, melatonin, triiodothyronine, thyroxine, prostaglandin, leukotriene, prostacyclin, thrombaxane, amylin, anti-Mullerian hormone, adinopectin, adrenocorticotropic hormone, corticotrophin, angiotensinogen, angiotensin, antidiuretic hormone, vasopressin, atrial-natriuretic peptide, atriopeptin, brain natriuretic peptide, calcitonin, cholecystokinin, corticotropin-releasing hormone, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, hepcidin, human chorionic gonadotropin, human placental lactogen, growth hormone, inhibin, insulin, insulin-like growth factor, somatomedin, leptin, lipotropin, luteinizing hormone, melanocyte stimulating hormone, motilin, orexin, oxytocin, pancreatic polypeptide, parathyroid hormone, pituitary adenylate cyclase-activating peptide, prolactin, prolactin releasing hormone, relaxin, renin, secretin, somatostatin, thrombopoietin, thyroid-stimulating hormone, thyrotropin, vasoactive intestinal peptide, androgen, mineralocorticoid, estrogen, glucocorticoid, progestogen, and secosteroid.

A target molecule of the disclosure can comprise a hapten. Generally, a hapten can be a small molecule that can elicit an immune response when attached to a large carrier such as a protein. Examples of haptens include, but are not limited to, aniline, o-aminobenzoic acid, m-aminobenzoic acid, p-aminobenzoic acid, uroshiol, quinine, hydralazine, fluorescein, biotin, digoxigenin, and dinitrophenol.

A target molecule of the disclosure can comprise an ion channel (i.e. porin) or a receptor. A receptor can be from an immune cell. The immune cell can be a T cell, B cell, NK cell, or phagocyte. The phagocyte can be a monocyte, eosinophil, macrophage, neutrophil, mast cell or basophil. The receptor can be from a non-immune cell. For example, the non-immune cell can be an organ or tissue. The non-immune cell can be a skin cell, lung cell, heart cell, breast cell, muscle cell, kidney cell, glioma, and ovarian cell. The receptor can be a cell-surface receptor. The receptor can be an internal receptor. The receptor can be an ion-channel receptor, G-protein receptor, or enzyme-linked protein receptor. The receptor can be a transmembrane receptor. The receptor can comprise an external ligand binding domain (e.g., extracellular domain), hydrophobic membrane-spanning domain, intracellular domain, or any combination thereof. Examples of receptors include, but are not limited to, nicotinic acetylcholine receptor, glycine receptor, GABA receptor, glutamate receptor, 5-HT3 receptor, P2X receptor, cyclic nucleotide-gated ion channel, IP3 receptor, intracellular ATP receptor, ryanodine receptor, T cell receptor (TCR), B cell receptor (BCR), pattern recognition receptor (PRR), toll-like receptor (TLR), killer activated receptor (KAR), killer inhibitor receptor (KIR), complement receptor, Fc receptor, chemokine receptor, interferon receptor, growth factor receptor, including for example, epidermal growth factor receptor (EGFR) and human epidermal growth factor receptor 2 (HER2). The receptor can be a cytokine receptor, serine/threonine kinase receptor, tyrosine kinase receptor, IFN-α/β receptor (IFNAR), IFNGR, IL10R2, IFNLR1, or tumor necrosis factor receptor (TNF-R).

A target molecule of the disclosure can comprise a cytokine. Cytokines include, but are not limited to, chemokines, interferons, interleukins, lymphokines, and tumour necrosis factor (TNF). The chemokine can be from the CXC, CC, CX3C, or XC subfamily. The chemokine can be CCL2, CCL3, CCL5, CCL7, CCL8, CCL13, CCL17 and CCL22. The chemokine can be CCR1, CCR2, CCR3, CCR4, CCR5, CXCR2, and CXCR4. The chemokine can be CCL11, CCL24, CCL26, CCL5, CCL7, CCL13, and CCL3. The chemokine can be CCL2, CCL1, CCL22 and CCL17. The chemokine can be CXC chemokine. The chemokine can be CXC8. The interferon can be a type I interferon, type II interferon, or type III interferon. The interferon can be IFN-α, IFN-β, IFN-ε, IFN-κ, IFN-ω, IFN-γ. The interleukin (IL) can be IL-1, IL-2, IL-3, IL-4, IL-5, IL-6, IL-7, IL-8, IL-9, IL-10, IL-11, IL-12, IL-13, IL-15, or IL-17. The lymphokine can be granulocyte-macrophage colony-stimulating factor or interferon-gamma. The tumor necrosis factor can be TNF, lymphotixin-alpha, CD40L, CD27L, CD30L, FASL, 4-1BBL, OX40L, and TNF-related apoptosis inducing ligand (TRAIL). A target molecule of the disclosure also can be a neuropeptide.

A target molecule of the disclosure can comprise an enzyme. Enzymes can be classified as oxidoreductases, transferases, hydrolases, lyases, isomerases, and ligases. An oxidoreductase can catalyze oxidation/reduction reactions. A transferase can transfer a functional group (e.g. a methyl or phosphate group). A hydrolase can catalyze the hydrolysis of various bonds. Lyases can cleave various bonds by means other than hydrolysis and oxidation. An isomerase can catalyze isomerization changes within a single molecule. A ligase can join two molecules with covalent bonds. The enzyme can be lactase, reductase, dehydrogenase, and polymerase. The enzyme can be an alcohol dehydrogenase, alcohol dehydrogenase, homoserine dehydrogenase, aminopropanol oxidoreductase, diacetyl reductase, glycerol dehydrogenase, propanediol-phosphate dehydrogenase, glycerol-3-phosphate dehydrogenase, D-xylulose reductase, L-xylulose reductase, lactate dehydrogenase, malate dehydrogenase, isocitrate dehydrogenase, HMG-CoA reductase, decarboxylase, dehydratase, aldehyde lyases, oxo acid lyase, carbon-carbon lyase, carbon-nitrogen lyase, carbon-sulfur lyase, carbon-halide lyase, phosphorous-oxygen lyase, ferrochelatase, adenylate cyclase, deaminase, oxidase, kinase or an enzyme for bacterial autoinducer.

A target molecule of the disclosure can comprise a polymerase. The polymerase can be a DNA polymerase, RNA polymerase, or DNA/RNA polymerase. The polymerase can be a eukaryotic polymerase. The polymerase can be a prokaryotic polymerase. The DNA polymerase can be Pol I, Pol II, Pol III, Pol IV, or Pol V. The DNA polymerase can be polymerase beta, polymerase lambda, polymerase sigma, polymerase mu, polymerase alpha, polymerase delta, polymerase epsilon, polymerase eta, polymerase iota, polymerase kappa, polymerase Rev1, polymerase zeta, telomerase, polymerase gamma and polymerase theta. The RNA polymerase can be RNA polymerase I, RNA polymerase II, RNA polymerase III, RNA polymerase IV, or RNA polymerase V. The RNA polymerase can be RNAP. The RNA polymerase can comprise a subunit of RNAP. The subunit of RNAP can be β', β, α', α", and ω. The polymerase can be a RNA-dependent DNA polymerase (RdDp). The RdDp can be a reverse transcriptase. The polymerase can be VentR® DNA Polymerase, VentR™ (exo-) DNA Polymerase, OneTaq® DNA Polymerase, LongAmp® Taq DNA Polymerase, T4 DNA Polymerase, Phusion® High-Fidelity DNA Polymerase, Taq DNA Polymerase, OneTaq® Hot Start DNA Polymerase, DNA Polymerase I, Large (Klenow) Fragment, Q5® High-Fidelity DNA Polymerase, SP6 RNA Polymerase, T7 RNA Polymerase, E. coli RNA Polymerase, Holoenzyme, E. coli RNA Polymerase, Core Enzyme, Poly (U) Polymerase, and E. coli Poly(A) Polymerase.

A target molecule of the disclosure can comprise a ligase. A ligase can be a eukaryotic ligase. The ligase can be a prokaryotic ligase. The ligase can be a single-stranded ligase. The ligase can be a double-stranded ligase. The ligase can be a DNA ligase. The DNA ligase can be T4 DNA ligase, Taq DNA ligase, T7 DNA ligase, T3 DNA ligase, 9° N™ DNA Ligase, and E. coli DNA ligase. The ligase can be a RNA ligase. The RNA ligase can be T4 RNA ligase 1, T4 RNA ligase 2, T4 RNA ligase truncated, T4 RNA ligase 2 truncated K227Q, T4 RNA ligase 2 truncated KQ, and thermostable 5' AppDNA/RNA ligase. The ligase can be a thermostable ligase. The ligase can be a DNA/RNA ligase. The ligase can be a SplintR® ligase, blunt/TA ligase, and sticky-end ligase. The ligase can be CircLigase™, CircLigase™ II.

A target molecule of the disclosure can comprise a reverse transcriptase. A reverse transcriptase can be a viral reverse transcripase. The viral reverse transcriptase can be a retroviral reverse transcriptase. The reverse transcriptase can be a eukaryotic reverse transcriptase. The reverse transcriptase can be AMV Reverse Transcriptase, ProtoScript® II Reverse Transcriptase, M-MuLV Reverse Transcriptase, SuperScript® Reverse Transcriptase, Superscript® II Reverse Transcriptase, Superscript® III Reverse Transcriptase, HIV-1 reverse transcriptase, or telomerase reverse transcriptase.

A target molecule of the disclosure can comprise a nuclease. A nuclease can be a DNase. The nuclease maybe an RNase. The nuclease can be an exonuclease. The exonuclease can be Lambda Exonuclease, Exonuclease VII, T5 Exonuclease, T7 Exonuclease, Exonuclease T, Exonuclease I (E. coli), Exonuclease V (RecBCD), or Exonuclease III (E. coli). The nuclease can be an endonuclease. The endonuclease can be Endonuclease IV, T7 Endonuclease I, Endonuclease V, Endonuclease VIII, Tma Endonuclease III, Endonuclease III (Nth), T4 PDG (T4 Endonuclease V), or Tth Endonuclease IV. The RNase can be RNase H, RNase HII, RNase If, ShortCut® RNase III, XRN-1. Examples of nucleases include, but are not limited to, Afu Uracil-DNA Glycosylase (UDG), Tma Endonuclease III, Tth Endonuclease IV, Antarctic Thermolabile UDG, APE 1, Cas9 Nuclease, S. pyogenes, DNase I, Endonuclease III (Nth), Endonuclease IV, Endonuclease V, Endonuclease VIII, Exonuclease I (E. coli), Exonuclease III (E. coli), Exonuclease T, Exonuclease V (RecBCD), Exonuclease VII, Fpg, hAAG, hOGG1, hSMUG1, Lambda Exonuclease, Lambda Exonuclease Reaction Buffer, Micrococcal Nuclease, Mung Bean Nuclease, Nuclease BAL-31, RecAf, RecJf, T4 PDG (T4 Endonuclease V), T5 Exonuclease, T7 Endonuclease I, T7 Exonuclease, Uracil Glycosylase Inhibitor (UGI), and Uracil-DNA Glycosylase (UDG).

A target molecule of the disclosure can comprise a helicase. A helicase can be a eukaryotic helicase. The helicase can be a prokaryotic helicase. The helicase can be a DNA helicase. The helicase can be a RNA helicase. The helicase can be a DNA/RNA helicase. The helicase can be an ATP-dependent helicase. The helicase can be a single stranded helicase. The helicase can be a double-stranded helicase. The helicase can be a chromodomain helicase DNA binding protein. The helicase may be a DEAD box/DEAD/DEAH box helicase. Examples of helicases include, but are not limited to, ATXR, XPD, RecQ, ASCC3, BLM, BRIP1, DNA2, FBXO18, FBXO30, HELB, HELLS, HELQ, HELZ, HFM1, HLTF, IFIH1, NAV2, PIF1, RECQL, RTEL1, SHPRH, SMARCA4, SMARCAL1, WRN, WRNIP1, DDX3X, DDX5, DDX6, DDX10, DDX11, DDX12, DDX58, DHX8, DHX9, DHX37, DHX40, DHX58, CHD1, CHD1L, CHD2, CHD3, CHD4, CHD5, CHD6, CHD7, CHD8, and CHD9.

A target molecule of the disclosure can comprise a transposase. A transposase can be a DNA transposase. The transposase can be a Tn5 transposase or Mos1 DNA transposase. The transposase can be an integrase. The integrase can be a viral integrase. The transposase can be HIV-1 IN, ASV IN and MuA transposase.

A target molecule of the disclosure can comprise an antibody or antibody fragment. An antibody can comprise an immunoglobulin (Ig). The immunoglobulin can be IgG, IgM, IgA, IgD, IgE. The antibody can comprise an antibody light chain. The antibody light chain can be a kappa or lambda light chain. The antibody can comprise an antibody heavy chain. The antibody heavy chain can comprise an alpha, gamma, delta, epsilon, or mu heavy chain. The antibody can comprise an antibody fragment. The antibody can comprise a fragment antigen-binding (Fab), Fab2, fragment crystallizable (Fc), variable fragment (Fv), single chain fragment variable (scFv), dimeric single chain variable fragment (di-scFv), single domain antibody (sdAb), scFv-Fc, minibody, diabody, variable domain of a heavy chain (VH domain), variable domain of a light chain (VL domain), constant domain of a heavy chain (CH domain), constant domain of a light chain (CL domain), complementarity determining region (CDR). The antibody can be a monomer. The antibody can be a dimer. The dimer can be a homodimer. The dimer can be a heterodimer. The antibody can be a multimer. The antibody can be a pentamer. The antibody can be a bispefic antibody. The antibody can be a camelid. The antibody can be a trifunctional antibody. The antibody can be a bi-specific T-cell engager (BiTE). The antibody can be a monoclonal antibody. The antibody can be a polyclonal antibody. The antibody can be a chimeric antibody. A chimeric antibody can refer to an antibody comprising regions derived from two or more sources. The two or more sources can be from different species. Alternatively, the two or more sources can be from different cells. The cells can be of the same cell type. Alternatively, the cells can be of different cell types. The antibody can be a human antibody. The antibody can be a humanized antibody. The antibody can be from a mammal, reptile, bird, and fish. The mammal can be a human, non-human primate, dog, cat, cow, sheep, rabbit, goat, rat mouse, bear, horse, camel, and pig. Examples of antibodies include, but are not limited to, abagovomab, abciximab, actoxumab, adalimumab, adecatumumab, aducanumab, afelimomab, afutuzumab, alacizumab pegol, ald518, alemtuzumab, alirocumab, altumomab pentetate, amatuximab, anatumomab mafenatox, anifrolumab, anrukinzumab, apolizumab, arcitumomab, aselizumab, atinumab, atorolimumab, bapineuzumab, basiliximab, bavituximab, bectumomab, belimumab, benralizumab, bertilimumab, besilesomab, bevacizumab, bezlotoxumab, biciromab, bimagrumab, bivatuzumab mertansine, blinatumomabblosozumab, brentuximab vedotin, briakinumab, brodalumab, canakinumab, cantuzumab mertansine, cantuzumab ravtansine, caplacizumab, capromab pendetide, carlumab, catumaxomab, cc49, cbr96-doxorubicin immunoconjugate, cedelizumab, certolizumab pegol, cetuximab, citatuzumab bogatox, cixutumumab, clazakizumab, clenoliximab, clivatuzumab tetraxetan, conatumumab, concizumab, crenezumab, cr6261, dacetuzumab, daclizumab, dalotuzumab, daratumumab, demcizumab, denosumab, detumomab, dorlimomab aritox, drozitumab, duligotumab, dupilumab, dusigitumab, ecromeximab, eculizumab, edobacomab, edrecolomab, efalizumab, efungumab, eldelumab, elotuzumab, elsilimomab, enavatuzumab, enlimomab pegol, enokizumab, enoticumab, ensituximab, epitumomab cituxetan, epratuzumab, erlizumab, ertumaxomab, etaracizumab, etrolizumab, evolocumab, exbivirumab, fanolesomab, faralimomab, farletuzumab, fasinumab, fbta05, felvizumab, fezakinumab, ficlatuzumab, figitumumab, flanvotumab, fontolizumab, foralumab, foravirumab, fresolimumab, fulranumab, futuximab, galiximab, ganitumab, gantenerumab, gavilimomab, gemtuzumab ozogamicin, gevokizumab, girentuximab, glembatumumab vedotin, golimumab, gomiliximab, guselkumab, ibalizumab, ibritumomab tiuxetan, icrucumab, igovomab, imab362, imciromab, imgatuzumab, inclacumab, indatuximab ravtansine, infliximab, intetumumab, inolimomab, inotuzumab ozogamicin, ipilimumab, iratumumab, itolizumab, ixekizumab, keliximab, labetuzumab, lambrolizumab, lampalizumab, lebrikizumab, lemalesomab, lerdelimumab, lexatumumab, libivirumab, ligelizumab, lintuzumab, lirilumab, lodelcizumab, lorvotuzumab mertansine, lucatumumab, lumiliximab, mapatumumab, margetuximab, maslimomab, mavrilimumab, matuzumab, mepolizumab, metelimumab, milatuzumab, minretumomab, mitumomab, mogamulizumab, morolimumab, motavizumab, moxetumomab pasudotox, muromonab-cd3, nacolomab tafenatox, namilumab, naptumomab estafenatox, narnatumab, natalizumab, nebacumab, necitumumab, nerelimomab, nesvacumab, nimotuzumab, nivolumab, nofetumomab merpentan, ocaratuzumab, ocrelizumab, odulimomab, ofatumumab, olaratumab, olokizumab, omalizumab, onartuzumab, ontuxizumab, oportuzumab monatox, oregovomab, orticumab, otelixizumab, otlertuzumab, oxelumab, ozanezumab, ozoralizumab, pagibaximab, palivizumab, panitumumab, pankomab, panobacumab, parsatuzumab, pascolizumab, pateclizumab, patritumab, pemtumomab, perakizumab, pertuzumabpexelizumab, pidilizumab, pinatuzumab vedotin, pintumomab, placulumab, polatuzumab vedotin, ponezumab, priliximab, pritoxaximab, pritumumab, pro 140, quilizumab, racotumomab, radretumab, rafivirumab, ramucirumab, ranibizumab, raxibacumab, regavirumab, reslizumab, rilotumumab, rituximab, robatumumab, roledumab, romosozumab, rontalizumab, roveliztumabrupluzimab, samalizumab, sarilumab, satumomab pendetide, secukinumab, seribantumab, setoxaximab, sevirumab, sibrotuzumab, sgn-cd19a, sgn-cd33a, sifalimumab, siltuximab, simtuzumab, siplizumab, sirukumab, solanezumab, solitomab, sonepcizumab, sontuzumab, stamulumab, sulesomab, suvizumab, tabalumab, tacatuzumab tetraxetan, tadocizumab, talizumab, tanezumab, taplitumomab paptox, tefibazumab, telimomab aritox, tenatumomab, teneliximab, teplizumab, teprotumumab, tgn1412, ticilimumab, tremelimumab, tildrakizumab, tigatuzumab, tnx-650, tocilizumab, atlizumab, toralizumab, tositumomab, tovetumab, tralokinumab, trastuzumab, trbs07, tregalizumab, tremelimumab, tucotuzumab celmoleukin, tuvirumab, ublituximab, urelumab, urtoxazumab, ustekinumab, vantictumab, vapaliximab, vatelizumab, vedolizumab, veltuzumab, vepalimomab, vesencumab, visilizumab, volociximab, vorsetuzumab mafodotin, votumumab, zalutumumab, zanolimumab, zatuximab, ziralimumab, and zolimomab aritox.

A target molecule of the disclosure can comprise a polynucleotide. The polynucleotide can comprise one or more nucleotides. A polynucleotide can comprise 2, 3, 4, 5, 6, 7, 8, 9, 10, 11, 12, 13, 14, 15, 16, 17, 18, 19, or 20 or more nucleic acids. A polynucleotide can comprise 20, 30, 40, 50, 60, 70, 80, 90, 100, 110, 120, 130, 140, 150, 160, 170, 180, 190, or 200 or more nucleic acids. A polynucleotide can comprise 200, 300, 400, 500, 600, 700, 800, 900, 1000, 1100, 1200, 1300, 1400, 1500, 1600, 1700, 1800, 1900, or 2000 or more nucleic acids. The one or more nucleotides can comprise ribonucleotides, deoxyribonucleotides, locked nucleic acids (LNAs), peptide nucleic acids (PNAs), or any combination thereof. The polynucleotide can comprise a purine base, pyrimidine base, or both. The polynucleotide can comprise or natural, chemically-modified, biochemically-modified, non-natural, or derivatized nucleotide bases. The polynucleotide can comprise one or more unpaired nucleotide bases. The polynucleotide can be single-stranded. The polynucleotide can comprise one or more paired nucleotide bases. The polynucleotide can be double-stranded. The polynucleotide can comprise a double-stranded DNA, double-stranded RNA, or a double-stranded DNA/RNA hybrid. The polynucleotide can be a synthetic polynucleotide. In some instances, the sequence of the polynucleotide is known. For example, the polynucleotide can comprise a polyadenylated sequence. In some instances, the sequence of the polynucleotide is unknown. For example, the polynucleotide of the random sequence can comprise a degenerate sequence. In some instances, only a portion of the sequence of the polynucleotide is known. For example, the polynucleotide can comprise a polyadenylated sequence but the remainder of the sequence is unknown.

A target molecule of the disclosure can comprise an oligonucleotide primer. An oligonucleotide primer can be an amplification or sequencing primer. An amplification or sequencing primer can be used in the amplification or sequencing of another polynucleotide. For example, an amplification or sequencing primer can comprise a sequence that is partially complementary to a gene. The amplification or sequencing primer can hybridize to the gene and enable amplification or sequencing of the gene. An amplification or sequencing primer can be a specific primer. Generally, a specific primer is complementary to a sequence of a polynucleotide (e.g., a gene, exon region, etc.). The sequence of the polynucleotide can be unique to the polynucleotide. For example, a specific primer can hybridize to at least a portion of an antibody gene. An amplification or sequencing primer can be an universal primer. Generally, a universal primer is complementary to a sequence that is common to two or more types of polynucleotides. For example, a universal primer can comprise an oligodT sequence that can hybridize to a polyadenylated sequence of two or more polynucleotides (e.g., mRNA). The amplification or sequencing primer can hybridize to a sequence that is natural to the polynucleotide (e.g., a polyA sequence of mRNA, a restriction site, an exon region). The amplification or sequencing primer can hybridize to a sequence that is unnatural to the polynucleotide (e.g., an adapter sequence or a barcode sequence). The amplification or sequencing primer can comprise a random or degenerate sequence. For example, the amplification or sequencing primer can comprise a random hexamer sequence. Examples of amplification or sequencing primers include, but are not limited to, oligodT, random primer, gene-specific primer, and promoter primers. The oligodT primer can be an oligo(dT)20, oligo(dT)18 or oligo(dT)12-18 primer. The random primer can be a random 9-mer primer or random 6-mer primer. The random primer can comprise oligodeoxyribonucleotides. Alternatively, the random primer includes oligodeoxynucleotides. Examples of gene-specific primers include, but are not limited to, cytokine gene primers and housekeeping gene primers. A promoter primer can be, for example, a SP6 primer, T7 promoter primer, Runx2 promoter primer, GAPDH promoter primer, U6 promoter primer, T3 promoter primer, and CaMV 35S promoter primer. A target molecule can comprise an oligonucleotide primer selected from the group consisting of 3'AOX1 (for sequences with AOX1 terminator, reverse primer), 5'AOX1 (for sequences with AOX1 promoter, forward primer), 35S promoter (CaMV 35S promoter, forward primer), AC5 (*drosophila* Actin 5C promoter, forward primer), Alpha-factor (alpha factor signal sequence, forward primer), Amp-R (5' end of ampicillin resistance gene, reverse primer), AUG1 Forward (for sequences with AUG1 promoter, forward primer), AUG1 Reverse (for sequences with AUG1 promoter, reverse primer), BGH Reverse (bovine growth hormone terminator, reverse primer), Bglob-intron-F (rabbit beta-globin intron, forward primer), Bglob-intron-R (rabbit beta-globin intron, reverse primer), Bglob-pA-R (rabbit beta-globin polyA region, reverse primer), CAT-R (5' end of chloramphenicol resistance gene, reverse primer), CMV Forward (human CMV immediate early promoter, forward primer), CRE-R (5' end of Cre recombinase, reverse primer), CYC1 (CYC1 transcription termination signal, reverse primer), DsRed1-C(3' end of DsRed1, forward primer), DsRed1-N(5' end of DsRed1, reverse primer), EBV Reverse (SV40 polyA terminator, reverse primer), Ecdysone forward (*drosophila* heat shock promoter, forward primer), EF-1a forward (human elongation factor-1a promoter, forward primer), EGFP-C(3' end of EGFP, forward primer), EGFP-N(5' end of EGFP, reverse primer), EXFP-R (for distinguishing EGFP vs ECFP vs EYFP, reverse primer), Flori-F (F1 origin, forward primer), GAL1 (*S. cerevisiae* GAL1 promoter, forward primer), Gal10pro-F (*S. cerevisiae* GAL10 promoter, forward primer), Gal4 N-term (3' end of Gal4 DNA binding domain, forward primer), Gal4-AD (3' end of Gal4 activation domain, forward primer), GFP-F (3' end of GFP, forward primer), GFP-R (5' end of GFP, reverse primer), GPDpro-F (*S. cerevisiae* GPD promoter, forward primer), GW-3' (3' end of Gateway cassette, forward primer), GW-5' (5' end of Gateway cassette, reverse primer), H1 (human H1 promoter, forward primer), HA-F (HA tag, forward primer), HA-R (HA tag, reverse primer), HAT (histidine affinity tag, forward primer), hGH-PA-R (human growth hormone terminator, reverse primer), hrGFP-R (hrGFP (humanized *Renilla* GFP), forward primer), hUBCpro-F (human Ubiquitin C (UbC) promoter, forward primer), IRES-F (3' end of IRES, forward primer), IRES-R (5' end of IRES, reverse primer), L4440 (5' of MCS in L4440 vector, forward primer), LacI-R (5' end of LacI, reverse primer), LacZ-R (5' end of LacZ, reverse primer), LexA (3' end of LexA DNA binding domain, forward primer), LKO.1 5' (human U6 promoter, forward primer), LNCX (human CMV promoter, forward primer), Luc-F (3' end of luciferase, forward primer), Luc-Nrev (5' end of luciferase, reverse primer), M13 (−21) forward (in lacZ gene), M13 (−40) (in lacZ gene), M13 Reverse (in lacZ gene), M13/pUC forward (in lacZ gene), M13/pUC Reverse (in lacZ gene), MBP-F (3' end of maltose binding protein, forward primer), mCherry-F (3' end of mCherry, forward primer), mCherry-R (5' end of mCherry, reverse primer), MT forward (*drosophila* metallothionein promoter, forward primer), MMLV-F (Moloney murine leukemia virus LTR (MoMuLV), forward primer), mPGK-F (mouse PGK promoter, forward primer), MSCV (murine stem cell virus, forward primer), MSCV-rev (murine stem cell virus, reverse primer), MT1-F (mouse metallothionein 1 promoter, forward primer), mU6-F (mouse U6 promoter, forward primer), Myc (Myc tag, forward primer), Neo-F (3' end of neomycin resistance gene, forward primer), Neo-R (5' end of neomycin resistance gene, reverse primer), NOS-F (Nopaline synthase promoter, forward primer), Nmt1-F (*S. pombe* nmt1 promoter, forward primer), OpIE2 forward (OpIE2 promoter, forward primer), pACYC-F (p15A origin, forward primer), pAd-CMV (for cloning sites after SalI in pAd-CMV vector), pBABE 3' (SV40 enhancer, 3' of MCS in pBABE vectors, reverse primer), pBABE 5' (Psi packaging signal, 5' of MCS in pBABE vectors, forward primer), pBAD forward (for sequences with *E. coli* araBAD promoter, forward primer), pBAD reverse (for sequences with *E. coli* araBAD promoter, reverse primer), pBluescriptKS (for pBluescript vector sequences), pBluescriptSK (for pBluescript vector sequence), pBMN 5' (MMLV sequence, for inserts in pBMN retroviral vector), pBR322ori-F (pBRS322 origin, forward primer), pBRforBam (in pBR322 tet region, upstream of BamHI, forward primer), pBRforEco (in pBR322, upsteam of EcoRI site, forward primer), pBR-revBam (in pBR322 tet region, downstream of BamHI, reverse primer), pCAG-F (rabbit beta-globin intron, for pCAG plasmids, forward primer), pCasper-F (5' end of drosophila mini-white gene, reverse primer), pCasper-hs (drosophila Hsp70 promoter, forward primer), pcDL-F (5' of EcoRI site in pcDL vector, forward primer), pENTR-F (5' of attL1 in pENTR vector, forward primer), pENTR-R (3' of attL2 in pENTR vector, reverse primer), pGEX 3' (3' of MCS in pGEX vectors, reverse primer), pGEX 5' (3' end of glutathione-S-transferase, forward primer), pGP704-R (R6K gamma origin, 3' of MCS in pGP704 vector, reverse primer), pHybLex Reverse (ADH terminator, reverse primer), pLTet-F (lambda phage early leftward (pL) promoter, forward primer), pLXSN 5' (murine stem cell virus, same as MSCV, forward primer), pMRB101-F (HCMV major immediate-early protein (IE), forward primer), pMT2-F (3' end of synthetic intron, forward primer), pMX-S1811 (MMLV sequence, 5' of MCS in pMXs vector, forward primer), Polyhedrin forward (Polyhedrin promoter, forward primer), Polyhedrin reverse (for baculovirus vector with polyhedrin promoter, reverse primer), pQE promoter (5' of MCS in pQE vectors, forward primer), pREP Forward (Rous sarcoma virus (RSV) promoter, forward primer), pRS-marker (to sequence yeast selectable marker in pRS vectors), Pry1 (PZ P-element, reverse primer), pTrcHis Forward (5' of MCS in pTrcHis vector, forward primer), pTrcHis Reverse (3' of MCS in pTrcHis vector, same as pBAD-R, reverse primer), Puro-F (3' end of puromycin resistance gene, forward primer), pZIP (Murine leukemia virus (MuLV), reverse primer), RCAS-F (3' of Rous sarcoma virus (RSV) env gene, forward primer), Rluc-F (3' end of Renilla luciferase, forward primer), RVprimer3 (5' of MCS in pGL3 vector, forward primer), SFFV-F (Spleen focus forming virus 5' LTR, forward primer), SP6 (SP6 promoter, forward primer), SV40 pA-R (SV40 polyA, reverse primer), SV40pro-F (SV40 promoter/origin, forward primer), SV40-spliceR (SV40 splice sequence, reverse primer), T3 (T3 promoter, forward primer), T7 (T7 promoter, forward primer), T7 Terminal (T7 terminator, reverse primer), Tac promoter (Tac promoter, forward primer), tdTomato-Fwd (3' end of tdTomato, forward primer), tdTomato-Rev (5' end of tdTomato, reverse primer), Tet-R (5' end of tetracycline resistance gene, reverse primer), TK-pA-R (Thymidine kinase polyA, reverse primer), Tn7-end (Bacterial transposon Tn7), TRC-F (Human U6 promoter, forward primer), Ubx-F (Drosophila Ultrabithorax gene, forward primer), V5 Reverse (V5 epitope, reverse primer), WPRE-R (5' end of WPRE, reverse primer), XBG-R (Xenopus beta-globin 3'UTR, reverse primer), XEF1a (Xenopus EF1 alpha enhancer/promoter, forward primer), and Xpress Forward (Xpress epitope, forward primer).

A target molecule of the disclosure can comprise a RNA molecule. The RNA can be a protein-coding RNA. The protein-coding RNA can be an mRNA. The RNA can be a noncoding RNA (ncRNA). The ncRNA can be a ribosomal RNA (rRNA), transfer RNA (tRNA), small interfering RNA (siRNA), microRNA (miRNA), small nuclear RNA (snRNA), small nucleolar RNA (snoRNA), long noncoding RNA (lncRNA), and Piwi interacting RNA (piRNA). The RNA can be a synthetic RNA. Examples of synthetic RNA include, but are not limited to, an antisense RNA, short hairpin RNA (shRNA), complementary RNA (cRNA). The RNA can be derived from an exon. The RNA can be derived from an intron. The RNA can be derived on an untranslated region (UTR). The RNA can be polyadenylated. In some instances, RNA is not poyladenylated.

A target molecule of the disclosure can comprise a DNA molecule. The DNA can be genomic DNA (gDNA) or complementary DNA (cDNA). The DNA can be B-DNA. The DNA can be A-DNA. The DNA can be Z-DNA. The DNA can comprise at least a portion of a protein-coding region. The DNA can comprise at least a portion of a gene. The DNA can comprise an exon. The DNA can comprise an intron. The DNA can comprise an untranslated region (UTR). The DNA can comprise at least a portion of a noncoding DNA. The noncoding DNA can comprise a sequence that is transcribed into a noncoding RNA. The noncoding DNA can comprise a regulatory element. The regulatory element can be a cis-regulatory element. The regulatory element can be a trans-regulatory element. The regulatory element can be a promoter. The promoter can facilitate the transcription of a gene. The promoter can be located upstream of a coding region. The regulatory element can be an enhancer. The enhancer can exert distant effects on the transcription level of genes. The noncoding DNA can comprise a pseudogene. The noncoding DNA can comprise transposons or retrotransposons. The noncoding DNA can comprise repeated sequences such as long interspersed nuclear elements (LINES) and short interspersed nuclear elements (SINES). The SINE can comprise an Alu sequence. The noncoding DNA can comprise viral elements. The noncoding DNA can comprise telomeres.

A target molecule of the disclosure can comprise a carbohydrate. A carbohydrate can be a monosaccharide, disaccharide, oligosaccharide, or polysaccharide. Examples of monosaccharides include, but are not limited to, glyceraldehydes, galactosamine, glucosamine, sialic acid, N-acetylglucosamine, sulfoquinovose, pyranose, glucopyranose, furanose, glucose, fructose, and galactose. The disaccharide can be sucrose, lactose, trehalose, cellobiose or maltose. The oligosaccharide can be fructo-oligosaccharides, galactooligosaccharides, and mannan oligosaccharides. The polysaccharide can be a storage polysaccharide. The polysaccharide can be a structural polysaccharide. Examples of polysaccharides include, but are not limited to, starch, glycogen, chitin, amylase, branched amylopectin, callose or laminarin, chrysolaminarin, xylan, arabinoxylan, mannan, fucoidan galactomannan and cellulose.

A target molecule of the disclosure can comprise an organic compound. Generally, an organic compound is a compound whose molecules contain carbon. The organic compound can be a natural compound. Generally, natural organic compounds refer to those that are produced by plants or animals. Examples of natural organic compounds include most sugars, some alkaloids and terpenoids, certain nutrients such as vitamin B12. The organic compound can be a synthetic compound. Generally, a synthetic organic compound can be prepared by reaction of other compounds are referred to as "synthetic." Polymers, including plastics and rubbers, can be organic synthetic or semi-synthetic compounds. Some organic compounds can be manufactured using the biochemistry of organisms such as bacteria and yeast. The organic compound can be a small molecule, alcohol, fatty acid, polyketide, hormone, or carbohydrate.

A target molecule of the disclosure can comprise an inorganic compound. Generally, a compound that is not referred to as an organic compound is an inorganic compound. Examples of carbon-containing inorganic compounds include, but are not limited to, carbides, carbonates, simple oxides of carbon (such as CO and CO2), and cyanides. Inorganic compounds can include quantum dots, metal nanoparticles, metal oxide nanoparticles and the like. Inorganic compounds also can include minerals, sulfides, organometallic compounds, and bioinorganic compounds. The mineral can be talc, gypsum, calcite, fluorite, apatite, orthoclase, quartz, topaz, corundum, or diamond.

A target molecule of the disclosure can comprise a small molecule. A small molecule can comprise a peptide. The peptide comprise one or more amino acids. The amino acid can be a natural amino acid. The amino acid can be an unnatural amino acid. The amino acid can be a D-amino acid. The amino acid can be an L-amino acid. Examples of amino acids include, but are not limited to, p-acetylphenalalanine, m-acetylphenalalanine, alanine, β-alanine, γ-aminoburyic acid (GABA), aminoisobutyric acid, δ-aminolevulinic acid, 4-aminobenzoic acid (PABA), arginine, asparagine, aspartic acid, p-benxoyl-1-phenylalanine, citrulline, cystathionine, cysteine, cystine, diaminopimelic acid, Djenkolic acid, glutamic acid, glutamine, glycine, histidine, isoleucine, lanthionine, leucine, lysine, methionine, ornithine, phenylalanine, phenylselenidylalanine, proline, selenocysteine, serine, threonine, tryptophan, tyrosine, and valine. The small molecule can comprise a therapeutic agent.

A target molecule of the disclosure can comprise a metabolite. Examples of metabolites include, but are not limited to, alkaloids, glycosides, lipids, nonribosomal peptides, such as actinomycin-d, phenazines, natural phenols (including flavonoids), polyketide, terpenes, including steroids, and tetrapyrroles.

A target molecule of the disclosure can comprise a therapeutic agent. A therapeutic agent can comprise an organic compound, inorganic compound, peptide, hormone, small molecule, antibody, antigen, hapten, or any combination thereof. The therapeutic agent can be an antipyretic, analgesic, antimalarial drug, antibiotic, antiseptic, mood stabilizer, hormone replacement, oral contraceptive, stimulant, tranquilizer, antiviral drug, anti-cancer drug, immunosuppressant, and statin. The tranquilizer can be meprobamate, chlorpromazine, reserpine, chlordiazepoxide, diazepam, and alprazolam. The statin can be lovastatin, pravastatin, or simvastatin.

In some embodiments a substrate provided herein contains a plurality of features. A plurality of features on a substrate is also referred to herein as an array or an array of features.

Figure 5:
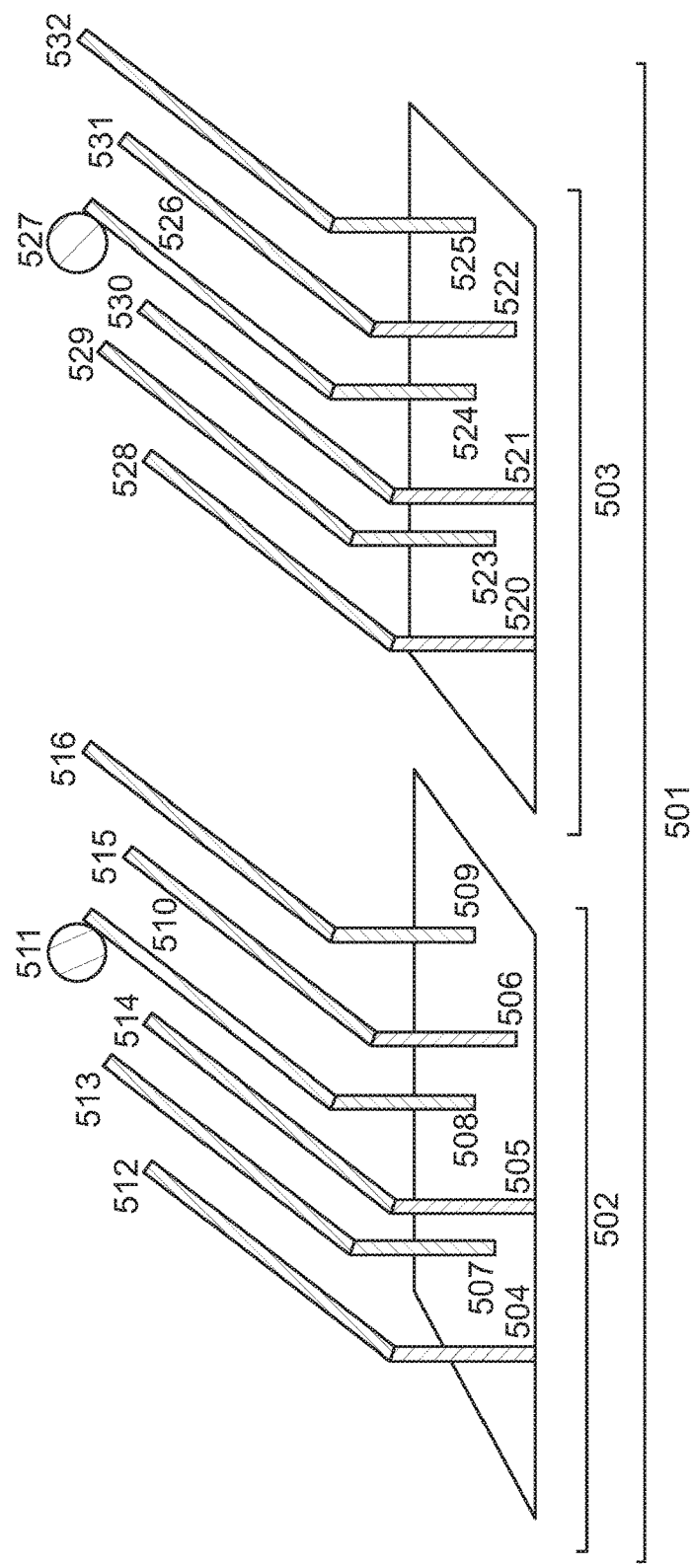
FIG. 5 shows an exemplary substrate comprising at least two features.

An exemplary substrate comprising two or more features is depicted in FIG. 5. As shown in FIG. 5, a substrate (501) can comprise two or more features (502, 503). A first feature (502) can comprise a plurality of first capture primers (504, 505, 506) and a plurality of second capture primers (507, 508, 509). The first feature (502) can further comprise a first target polynucleotide (510). The first target polynucleotide (510) can be affixed to the first feature (502) by attachment of the first target polynucleotide (510) to a first capture primer (504). The first feature (502) can further comprise a plurality of amplicons (512, 513, 514, 515, 516). The plurality of amplicons (512, 513, 514, 515, 516) can comprise amplicons of the first target polynucleotide (510). The first feature (502) can further comprise a first target molecule (511). The first target molecule (511) can be attached to the first target polynucleotide (510). A second feature (503) can comprise a plurality of first capture primers (520, 521, 522) and a plurality of second capture primers (523, 524, 525). The second feature (503) can further comprise a second target polynucleotide (526). The second target polynucleotide (526) can be affixed to the second feature (503) by attachment of the second target polynucleotide (526) to a second capture primer (520). The second feature (503) can further comprise a plurality of amplicons (528, 529, 530, 531, 532). The plurality of amplicons (528, 529, 530, 531, 532) can comprise amplicons of the second target polynucleotide (526). The second feature (503) can further comprise a second target molecule (527). The second target molecule (527) can be attached to the second target polynucleotide (526). The substrate can comprise two or more identical features. For example, the first feature (502) and the second feature (503) can be identical. The substrate can comprise two or more different features. For example, the first feature (502) and the second feature (503) can be different. The first feature (502) and the second feature (503) can differ by the first capture primers associated with each feature. For example, the plurality of first capture primers (504, 505, 506) of the first feature (502) can be different from the plurality of first capture primers (520, 521, 522) of the second feature (503). The first feature (502) and the second feature (503) can differ by the second capture primers associated with each feature. For example, the plurality of second capture primers (507, 508, 509) of the first feature (502) can be different from the plurality of second capture primers (523, 524, 525) of the second feature (503). The first feature (502) and the second feature (503) can differ by the target polynucleotide associated with each feature. For example, the first target polynucleotide (510) of the first feature (502) can be different from the second target polynucleotide (526) of the second feature (503). Subsequently, the plurality of amplicons (512, 513, 514, 515, 516) of the first feature (502) can be different from the plurality of amplicons (528, 529, 530, 531, 532) of the second feature (503). The first feature (502) and the second feature (503) can differ by the target molecule associated with each feature. For example, the first target molecule (511) of the first feature (502) can be different from the second target molecule (527) of the second feature (503). The first feature can further comprise one or more additional target molecules. The second feature can further comprise one or more additional target molecules. The one or more additional target molecules from the first feature can be the same as the one or more additional target molecules from the second feature. Alternatively, or additionally, the one or more additional target molecules from the first feature can be different from the one or more additional target molecules from the second feature.

A substrate having a plurality of features can appear as a grid of spots or patches. The features can be located in a repeating pattern. Alternatively, or additionally, the features can be located in an irregular non-repeating pattern. In some embodiments, the patterns are hexagonal patterns, rectilinear patterns, grid patterns, patterns having reflective symmetry, patterns having rotational symmetry, or the like. Asymmetric patterns can also be useful. The pitch can be the same between different pairs of nearest neighbor features or the pitch can vary between different pairs of nearest neighbor features.

A substrate having a plurality of features and the methods set forth herein using such arrays can have features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

In particular embodiments, features of an array can each have an area that is larger than about 100 nm$^2$, 250 nm$^2$, 500 nm$^2$, 1 μm$^2$, 2.5 μm$^2$, 5 μm$^2$, 10 μm$^2$, 100 μm$^2$, or 500 μm$^2$. Alternatively or additionally, features of an array can each have an area that is smaller than about 1 mm$^2$, 500 μm$^2$, 100

$\mu m^2$, 25 $\mu m^2$, 10 $\mu m^2$, 5 $\mu m^2$, 1 $\mu m^2$, 500 $nm^2$, or 100 $nm^2$. Indeed, a region can have a size that is in a range between an upper and lower limit selected, for example, from those exemplified above.

In some embodiments, the features on the surface of an array substrate are non-contiguous, being separated by interstitial regions of the surface. Interstitial regions that have a substantially lower quantity or concentration of capture primers or other capture agents, compared to the features of the array, can be useful. Interstitial regions that lack capture primers or other capture agents are particularly useful. For example, a relatively small amount or absence of capture agents at the interstitial regions favors localization of at least one target polynucleotide, and subsequently generated amplicon clusters, to desired features.

In particular embodiments, the features are concave features in a surface (e.g. wells) and the features can contain a gel material. The gel-containing features are separated from each other by interstitial regions on the surface where the gel is substantially absent or, if present the gel is substantially incapable of supporting localization of polynucleotides including, for example, capture primers.

In some embodiments, the wells are microwells or nanowells. Methods and compositions for making and using substrates having gel containing features, such as wells, are set forth in, for example, US 2014/0243224, which is incorporated herein by reference.

In some embodiments the feature size (e.g., area, diameter and the like) on an array are selected in a range favoring kinetic exclusion amplification (KEA) and the formation of single molecular placement in the feature. By exemplification in reference to embodiments employing wells as features, the well size (e.g., diameter) can be varied between about 30 nm and about 1 $\mu m$, between about 50 nm and about 800 nm, between about 70 nm and about 600 nm, or between 100 nm and about 400 nm. In some embodiments, the well has a diameter of about 400 nm. In some embodiments, the well has a diameter of less than about 1 $\mu m$. Exemplary microarrays include the microarrays on Illumina® HiSeq-X10 patterned flow cells.

In some embodiments that include an array of features on a surface, the features can be discrete, being separated by interstitial regions. The size of the features and/or spacing between the regions can vary such that arrays can be high density, medium density or lower density.

In some embodiments, the arrays are high density, medium density or low density arrays. High density arrays are characterized as having regions separated by less than about 15 $\mu m$. Medium density arrays have regions separated by about 15 to 30 $\mu m$, while low density arrays have regions separated by greater than 30 $\mu m$. An array useful in the invention can have regions that are separated by less than 100 $\mu m$, 50 $\mu m$, 10 $\mu m$, 5 $\mu m$, 1 $\mu m$ or 0.5 $\mu m$.

In some embodiments, arrays contain beads. In some embodiments, the beads are located on a surface including those wherein the beads are located in wells such as a BeadChip array (Illumina Inc., San Diego Calif.) or substrates used in sequencing platforms from 454 LifeSciences (a subsidiary of Roche, Basel Switzerland) or Ion Torrent (a subsidiary of Life Technologies, Carlsbad Calif.). Other arrays having beads located on a surface are described in U.S. Pat. Nos. 6,266,459; 6,355,431; 6,770,441; 6,859,570; 6,210,891; 6,258,568; 6,274,320; US 2009/0026082 A1; US 2009/0127589 A1; US 2010/0137143 A1; US 2010/0282617 A1 or PCT Publication No. WO 00/63437, each of which is incorporated herein by reference. Several of the above references describe methods for attaching target polynucleotides (or capture primers) to beads prior to loading the beads in or on an array substrate. It will however, be understood that the beads can be made to include capture primers and the beads can then be used to load an array, thereby forming amplification sites for use in a method set forth herein. As set forth previously herein, the substrates can be used without beads.

In some embodiments, exemplary bead compositions include, but are not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and teflon, as well as any other materials outlined herein for solid supports can all be used. "Microsphere Detection Guide" from Bangs Laboratories, Fishers Ind. is a helpful guide. In certain embodiments, the microspheres are magnetic microspheres or beads.

Accordingly, the disclosure provides a substrate having (a) a plurality of first and second capture primers immobilized to a feature; (b) at least one target polynucleotide, one end attached to one of said capture primers and the other end linked to a target molecule, wherein said target polynucleotide comprises a target region flanked by first and second capture primer binding regions complementary to said first and second capture primers, said second capture primer binding region comprising a base pair mismatch to said second capture primer, and (c) a plurality of clonal amplicons complementary to said target polynucleotide immobilized to said feature. The substrate can have one feature or a plurality of features. The feature or features can be a bead, well, including a microwell or nanowell, channel, ridge, projection or combination thereof. The feature or features include a single target molecule. The feature or features can be filled to capacity with a plurality of clonal amplicons of a target polynucleotide. Interstitial regions between a plurality of features can lack a target polynucleotide. The substrate having a plurality of features, including two or more features, can have different single target molecules in each of the different features within the plurality. The target polynucleotide on a feature include one or more polynucleotides selected from RNA, DNA, PNA or double stranded DNA (dsDNA). The length of the target polynucleotide on a feature can be less than 1,000 nucleotides. The length of the target polynucleotide on a feature can be between 10 to 25, 26 to 50, 51 to 100, 101 to 200, 201 to 300, 301 to 400, 401 to 500, 501 to 600, 601 to 700, 701 to 800, 801 to 900, or 901 to 1000 nucleotides. The target molecule can be a polypeptide, polynucleotide, carbohydrate, amino acid, nucleotide, monosaccharide, hapten, ligand, antigen, analyte, small molecule organic compound or inorganic compound. Polypeptide target molecules can be a nanopore, binding polypeptide or enzyme. A nanopore can be MspA, OmpF, OmpG, NalP, WZA, ClyA toxin, α-hemolysin, anthrax toxin, leukocidins or a DNA origami nanopore. A binding polypeptide can be an antibody, a Fab, a Fab', a F(ab')2, a scFV, a diabody, a triabody, a minibody and a single-domain antibody (sdAB) or T cell receptor. An enzyme can be a polymerase, helicase, recombinase, transpoase or ligase. The substrate can be one or more materials selected from glass, silicon, plastic or biopolymer. The substrate can further include a hydrogel or covalently-linked gel.

The disclosure further provides a method of placing a single target molecule on a feature of a substrate. The method includes (a) hybridizing a plurality of first and second capture primers immobilized to a feature on a substrate with (b) at least one target polynucleotide, said target polynucleotide a comprising a target region flanked by first and second capture primer binding regions complementary to said first and second capture primers, wherein said second capture primer binding region comprises a base pair mismatch to said second capture primer and being linked to a target molecule, and (c) amplifying said at least one target polynucleotide at an average amplification rate that exceeds an average transport rate of a target polynucleotide to a feature to produce a plurality of clonal amplicons complementary to said target polynucleotide.

A kinetic exclusion amplification (KEA) allows for the amplification of a single target polynucleotide per feature on a substrate including, for example, a patterned flow cell having wells, and the production of a monoclonal target polynucleotide population in one or more of the wells. Methods for performing KEA are well known in the art and are described in, for example, US 2013/0338042 A1. In a KEA the rate of amplification of the first captured target polynucleotide within a feature is much more rapid relative to much slower rates of target polynucleotide transport and capture. The first target polynucleotide captured in a feature can be amplified rapidly and fill the entire feature, preventing the capture of additional target polynucleotides in the same feature.

The present disclosure is based, in part, on the realization that the effectiveness of a KEA regarding the production of monoclonal target polynucleotide populations in features such as nanowells of patterned flow cells decreases as the size of the features or nanowells increases. Amplification of a first captured target polynucleotide and filling of a feature with a monoclonal population of target polynucleotides is slower in larger features than in smaller features, whereas the capture of a second target polynucleotide is faster in larger features than in smaller features. Thus, the likelihood that more than one target polynucleotide is captured and amplified within a feature increases with the size of the feature. The data quality of a molecular interrogation from a feature is optimal for monoclonal populations of target polynucleotides. The data quality from the feature decreases as the share of target polynucleotides other than the first immobilized target polynucleotide increases.

A specific example of the use of KEA for the placement of a single target molecule in each of a plurality of features is illustrated in FIG. 1. Briefly, the features of a substrate are patterned with immobilized capture primers, for example PAZAM inside nanowells grafted with a P5 and P7 capture primer pair. The target molecule such as polymerase or a nanopore polypeptide (shown as a star in FIG. 1) is linked to the end of a double stranded target polynucleotide by chemical conjugation. The target polynucleotide is able to be amplified using KEA (also known as recombinase polymerase amplifications (RPA)) with, for example, a commercialized TwistDX kit. RPA is one type of amplification methods mostly used in free solution. But KEA is one type of localized RPA reaction where the amplification can be taken in half-closed space such as solid substrate or beads surface, in order to generate monoclonal clusters of targeted nucleotides. The amplification quickly consumes the primers in the feature, preventing and/or significantly reducing the seeding and amplification from a different target polynucleotide and, therefore, eliminates or reduces the likelihood of loading the other target molecules.

In some embodiments, isothermal amplification can be performed using kinetic exclusion amplification (KEA), also referred to as exclusion amplification (ExAmp). A nucleic acid library of the present disclosure can be made using a method that includes a step of reacting an amplification reagent to produce a plurality of amplification sites that each includes a substantially clonal population of amplicons from an individual target nucleic acid that has seeded the site. In some embodiments the amplification reaction proceeds until a sufficient number of amplicons are generated to fill the capacity of the respective amplification site. Filling an already seeded site to capacity in this way inhibits target nucleic acids from landing and amplifying at the site thereby producing a clonal population of amplicons at the site. In some embodiments, apparent clonality can be achieved even if an amplification site is not filled to capacity prior to a second target nucleic acid arriving at the site. Under some conditions, amplification of a first target nucleic acid can proceed to a point that a sufficient number of copies are made to effectively outcompete or overwhelm production of copies from a second target nucleic acid that is transported to the site. For example in an embodiment that uses a bridge amplification process on a circular feature that is smaller than 500 nm in diameter, it has been determined that after 14 cycles of exponential amplification for a first target nucleic acid, contamination from a second target nucleic acid at the same site will produce an insufficient number of contaminating amplicons to adversely impact sequencing-by-synthesis analysis on an Illumina sequencing platform.

As demonstrated by the above example, amplification sites in an array can be, but need not be, entirely clonal in particular embodiments. Rather, for some applications, an individual amplification site can be predominantly populated with amplicons from a first target nucleic acid and can also have a low level of contaminating amplicons from a second target nucleic acid. An array can have one or more amplification sites that have a low level of contaminating amplicons so long as the level of contamination does not have an unacceptable impact on a subsequent use of the array. For example, when the array is to be used in a detection application, an acceptable level of contamination would be a level that does not impact signal to noise or resolution of the detection technique in an unacceptable way. Accordingly, apparent clonality will generally be relevant to a particular use or application of an array made by the methods set forth herein. Exemplary levels of contamination that can be acceptable at an individual amplification site for particular applications include, but are not limited to, at most 0.1%, 0.5%, 1%, 5%, 10% or 25% contaminating amplicons. An array can include one or more amplification sites having these exemplary levels of contaminating amplicons. For example, up to 5%, 10%, 25%, 50%, 75%, or even 100% of the amplification sites in an array can have some contaminating amplicons. It will be understood that in an array or other collection of sites, at least 50%, 75%, 80%, 85%, 90%, 95% or 99% or more of the sites can be clonal or apparently clonal.

In some embodiments, kinetic exclusion can occur when a process occurs at a sufficiently rapid rate to effectively exclude another event or process from occurring. Take for example the making of a nucleic acid array where sites of the array are randomly seeded with target nucleic acids from a solution and copies of the target nucleic acid are generated in an amplification process to fill each of the seeded sites to capacity. In accordance with the kinetic exclusion methods of the present disclosure, the seeding and amplification processes can proceed simultaneously under conditions where the amplification rate exceeds the seeding rate. As such, the relatively rapid rate at which copies are made at a site that has been seeded by a first target nucleic acid will effectively exclude a second nucleic acid from seeding the site for amplification. Kinetic exclusion amplification methods can be performed as described in detail in the disclosure of US Application Pub. No. 2013/0338042, which is incorporated herein by reference in its entirety.

Kinetic exclusion can exploit a relatively slow rate for initiating amplification (e.g. a slow rate of making a first copy of a target nucleic acid) vs. a relatively rapid rate for making subsequent copies of the target nucleic acid (or of the first copy of the target nucleic acid). In the example of the previous paragraph, kinetic exclusion occurs due to the relatively slow rate of target nucleic acid seeding (e.g. relatively slow diffusion or transport) vs. the relatively rapid rate at which amplification occurs to fill the site with copies of the nucleic acid seed. In another exemplary embodiment, kinetic exclusion can occur due to a delay in the formation of a first copy of a target nucleic acid that has seeded a site (e.g. delayed or slow activation) vs. the relatively rapid rate at which subsequent copies are made to fill the site. In this example, an individual site may have been seeded with several different target nucleic acids (e.g. several target nucleic acids can be present at each site prior to amplification). However, first copy formation for any given target nucleic acid can be activated randomly such that the average rate of first copy formation is relatively slow compared to the rate at which subsequent copies are generated. In this case, although an individual site may have been seeded with several different target nucleic acids, kinetic exclusion will allow only one of those target nucleic acids to be amplified. More specifically, once a first target nucleic acid has been activated for amplification, the site will rapidly fill to capacity with its copies, thereby preventing copies of a second target nucleic acid from being made at the site.

An amplification reagent can include further components that facilitate amplicon formation and in some cases increase the rate of amplicon formation. An example is a recombinase. Recombinase can facilitate amplicon formation by allowing repeated invasion/extension. More specifically, recombinase can facilitate invasion of a target nucleic acid by the polymerase and extension of a primer by the polymerase using the target nucleic acid as a template for amplicon formation. This process can be repeated as a chain reaction where amplicons produced from each round of invasion/extension serve as templates in a subsequent round. The process can occur more rapidly than standard PCR since a denaturation cycle (e.g. via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase and single stranded binding (SSB) protein is particularly useful as SSB can further facilitate amplification. Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. Nos. 5,223,414 and 7,399,590, each of which is incorporated herein by reference.

Another example of a component that can be included in an amplification reagent to facilitate amplicon formation and in some cases to increase the rate of amplicon formation is a helicase. Helicase can facilitate amplicon formation by allowing a chain reaction of amplicon formation. The process can occur more rapidly than standard PCR since a denaturation cycle (e.g. via heating or chemical denaturation) is not required. As such, helicase-facilitated amplification can be carried out isothermally. A mixture of helicase and single stranded binding (SSB) protein is particularly useful as SSB can further facilitate amplification. Exemplary formulations for helicase-facilitated amplification include those sold commercially as IsoAmp kits from Biohelix (Beverly, Mass.). Further, examples of useful formulations that include a helicase protein are described in U.S. Pat. Nos. 7,399,590 and 7,829,284, each of which is incorporated herein by reference.

Yet another example of a component that can be included in an amplification reagent to facilitate amplicon formation and in some cases increase the rate of amplicon formation is an origin binding protein.

KEA or other isothermal amplification methods can be utilized in a bridge amplification scheme in order to anchor a single target polynucleotide having a single target molecule to a feature. Although amplification of the target polynucleotide can be performed from both ends it is useful to linear amplify from the end distal to the attached target molecule in order to avoid or reduce loss of target polynucleotides (and attached target molecule) from some features. Linear amplification of the target polynucleotide can be accomplished by incorporating one or more base pair mismatch in the capture primer binding region of a target polynucleotide that is proximal to the attached target molecule. The capture primer binding region of the complementary strand that is not attached to the target molecule can be complimentary to its corresponding capture primer on the substrate. Following this exemplary configuration the first round of KEA will linearly amplify both strands of the target polynucleotide. However, subsequent rounds of amplification will linearly amplify the target polynucleotide strand attached to the target molecule and exponentially amplify the amplicon produced from the complementary strand.

The mismatch within the capture primer binding region can be placed at any location so long as it inhibits or retards invasion of the cognate capture primer and/or extension of the primer with a polymerase. Placing the mismatch at the end of the binding region complementary to a cognate capture primer as exemplified in FIGS. 4 and 6 is particularly useful because it both creates a low probability of strand invasion using a recombinase and inhibits and/or reduces extension by a polymerase because the capture primer is not hybridized at the 3' end to the target polynucleotide.

The above exemplary design for placing at least one target molecule in a feature or at least one target molecule in each of a plurality of features through KEA is illustrated in FIG. 4. Briefly, because the target molecule may diffuse away if the KEA displaced the polynucleotide strand conjugated to the target molecule, the target polynucleotide can be constructed with one or more mismatched base pairs in the capture primer regions. FIG. 4 illustrates a target polynucleotide consisting of PhiX target region flanked by capture primer regions. The 3' end (lower strand) of the ds target polynucleotide illustrates a capture primer binding region (P5') that includes a sequencing primer binding region (SBS3'). The 5' end (lower strand) illustrates a capture primer binding region (P7) that includes a sequencing primer binding region (SBS8). The complementary strand configuration is illustrated in the upper strand of the target polynucleotide. Although any base pair mismatch can be utilized, in this illustrative embodiment the P7/P7' capture primer binding region contains a three base pair mismatch corresponding to the CCC/CTA mismatching sequence is introduced at the 3' end of P7 sequence. On the 5' end of mutated or mismatched P7 strand, chemical conjugation can be used to link the target polynucleotide to the target molecule, which is illustrated by a star in FIG. 4. Alternatively, an abasic site or poly-8oxo-G (7,8-dihydro-8-oxoguanine) can be used to preserve the primary template molecule (P7 sequence).

Figure 6:
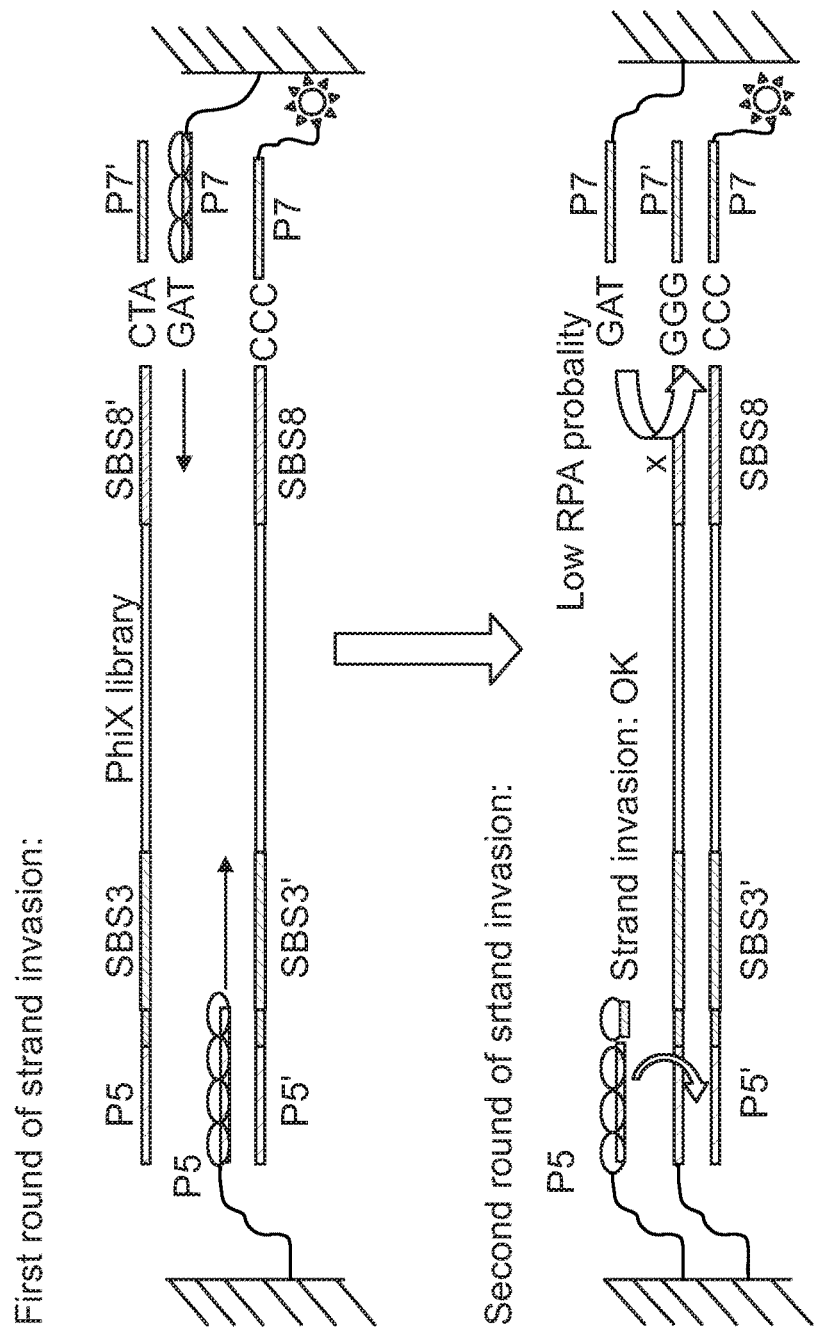
FIG. 6 illustrates first and second rounds of isothermal amplification using mismatched capture primer regions in a double stranded target polynucleotide.

FIG. 6 depicts the first and second round of KEA using the target polynucleotide design exemplified above. The feature is illustrated by the hatched planer markings on the right and left ends of the target polynucleotide. Attached to the feature are capture primers denoted as P5 and P7. The ovals decorating the capture primer illustrate the inclusion of SSB protein. These capture primers are complementary to P5' and P7' capture primer binding regions flanking the target region of the target polynucleotide. The P7 capture primer binding region adjacent or proximal to the attached target molecule is neither identical nor complementary to the P7, thus preventing or reducing strand invasion during KEA. As shown in FIG. 6, the regular or standard strand of P5-SBS3-phiX-SBS8'-P7' that is complementary to a P7 capture primer will undergo exponential amplification during KEA to consume the P5/P7 primer on a feature such as a nanowell. In contrast, the strand invasion will be inhibited from the P7 end of the mutated or mismatched strand. As a result, the target molecule attached to the target polynucleotide will stay hybridized to the substrate bound amplicon.

Accordingly, the methods provided herein can employ an initial capture and immobilization of a single target polynucleotide per feature or well of, for example, a patterned substrate such a flow cell using a first pair of capture primers as exemplified above. The initial target polynucleotide capture can be followed by an initial amplification of the single target polynucleotide to produce a monoclonal population of target polynucleotide amplicons within the feature by, for example, KEA. The initial target polynucleotide having an attached target molecule will remain immobilized to the feature by, for example, hybridization to an immobilized capture primer at the end distal to the target molecule.

Further, the methods provided herein can employ any of the components described previously, such as capture primers, capture primer binding regions, target polynucleotides, target molecules and the like, with reference to a substrate provided herein, or any combination thereof. These components can be employed with, for example, the exemplified mismatch capture primer binding region design and an isothermal amplification procedure that amplifies at least one target polynucleotide at an average amplification rate that exceeds an average transport rate of a target polynucleotide to a feature to generate any configuration of the substrates described herein having at least target polynucleotide attached to a target molecule immobilized to a feature.

Accordingly, the methods provided herein can be performed using any of the exemplary substrates described above including, for example, any shape of any insoluble solid support, semi-solid support or matrix to which a biomolecule can be attached including, for example, a polynucleotide. Exemplary solid supports include glass, modified glass, functionalized glass, inorganic glasses, microspheres (e.g. inert and/or magnetic particles), plastics, nylons, silica-based materials and the like as described previously.

Additionally, for example, the methods provided herein can be performed using a substrate that includes a flow-cell, for example, as described in US 2010/01 11768 A1 or Bentley et al, Nature 456:53-59 (2008) and exemplified previously.

The methods provided here can be performed on one or more features on a substrate including, for example, a well, pit, channel, ridge, raised region, peg, post, bead, metal or the like as described previously in reference to a substrate provided herein. In some embodiments, a method of placing at least one target molecule on a feature can utilize wells as a feature and can include gel material as set forth in US 2014-0243224 and described previously.

A method provided herein can utilize a substrate having first and second capture primers immobilized to a feature on the substrate. The first and second capture primers can be a plurality of first capture primers and a plurality of second capture primers. In some embodiments, the first and second capture primers can be directed to different sequences of a target polynucleotide and, therefore, exhibit specificity to different regions of the target polynucleotide. In other embodiments, the first and second capture primers can be directed to different target polynucleotides. An exemplary substrate that can be employed in a method for placing at least one target molecule on a feature is depicted in FIG. 2 as described previously.

Two or more capture primers utilized in method provided herein can be present in a feature in any ratio. For example, a plurality of first capture primers and a plurality second capture primers can be present in about equal amounts or in any other ratio, e.g., molar ratio including, for example, greater than 1.1× through to greater than 1,000× excess of a first capture primer over a second capture primer as exemplified previously. Similarly, a method provided herein employing a plurality of features the different features can have the same ratio of the two or more capture primers or a different ratio.

Briefly, for example, a capture primer utilized in a method of placing at least one target molecule on a feature can include one or more capture regions including, for example, a universal capture region, a sequencing primer binding site (SBS), a target-specific capture region, a predetermined cleavage site, such as a restriction site, and a linker region, for example, a linker region separating two or more regions of the capture primer. The capture primers can employ any of the designs exemplified previously such as a universal capture region and a SBS including any combination of the P5, P5', P7, P7', SBS3, SBS3', SBS8 and SBS8' and/or any other sequence that is sufficiently unique to function as universal primer, sequencing primer or any other sequence such as an adapter.

Thus, the methods provided herein can employ first and second capture primers immobilized to a feature that can include any capture region or any combination of capture regions. For example, the first capture primer can include a first universal capture region and the second capture primer can include the same universal capture region or a second universal capture region. The first and second capture primers can further include the same or different SBSs. For example, the first capture primer can include a first universal capture primer region and a first SBS and the second capture primer can include a second universal capture region and a second SBS.

A method provided herein can utilize a plurality of capture primers immobilized to a feature as described previously in reference to a substrate made by the methods provided herein. The plurality can be a single plurality, a plurality of first capture primers and a plurality of second capture primers. Alternatively, or additionally, a method provided herein can use a plurality of third, fourth, fifth and/or sixth or more capture primers. The number of pluralities of capture primers to include will depend on the application as exemplified previously. The plurality can be a population of two or more members including, for example, a plurality of is 2, 3, 4, 5, 6, 7, 8, 9, 10, 20, 30, 40, 50, 60, 70, 80, 90 or 100 or more different members of the population. In other embodiments, a plurality is 200, 300, 400, 500, 1000, 5000, 10000, 50000, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$ or $1\times10^7$, or more different members as well as any of the other members of pluralities exemplified previously. The plurality can contain different members, similar members and/or identical members including, for example, a mixture of any combination of different, similar and/or identical members from at least 1% up to and including 99% or more of the members.

A method provided herein can be used to immobilize on a feature at least one target polynucleotide attached at one end to a capture primer. A method provided herein also can be used to immobilize on a feature a single target polynucleotide attached at one end to a capture primer. Although described herein with reference to attachment of at least one target polynucleotide or with reference to a single target polynucleotide attached at one end to a capture primer immobilized to a feature, it is understood that in other embodiments, method provided herein can be used to immobilize two or more target polynucleotides attached at one end to capture primers immobilized to a feature. In these other embodiments, the number of target polynucleotides can be, for example, 2, 3, 4, 5, 6, 7, 8, 9, 10, 15, 20, 25, 30, 35, 40, 45, 50, 55, 60, 65, 70, 75, 80, 85, 90, 95 or 100 or more different target polynucleotides. Alternatively, or additionally the methods provided herein can be used to immobilize, for example, 2 to 100 or more identical, similar or different target polynucleotides including mixtures thereof as exemplified previously.

Any of the target polynucleotides exemplified previously can be employed in a method of placing at least one target molecule on a feature or on each of a plurality of features provided herein. Accordingly, a target polynucleotide employed in a method provided herein can comprise two or more nucleotides including, for example, ribonucleotides, deoxyribonucleotides, locked nucleic acids (LNAs), peptide nucleic acids (PNAs), or any combination thereof. A target polynucleotide can comprise a purine base, pyrimidine base, both a purine and pyrimidine base, natural, chemically-modified, biochemically-modified, non-natural, or derivatized nucleotide bases one or more paired nucleotide bases. A target polynucleotide employed in a method provided herein can be double stranded nucleic acid such as dsDNA, dsRNA, a double stranded DNA/RNA hybrid and also can include or more unpaired nucleotide bases. Single-stranded target polynucleotides also can be employed in a method provided herein as exemplified previously. Thus, a target polynucleotide can be any desired type of polynucleotide, sequence or mixture of types of polynucleotides and/or sequences.

Similarly, a target polynucleotide employed in a method provided herein can comprise one or more target polynucleotide regions as set forth previously including, for example, a capture primer binding region, target region, primer binding region, barcode region, linker region, and/or adapter region. The one or more target polynucleotide regions can be a plurality of target polynucleotide regions including, for example, 1, 2, 3, 4, 5, 6, 7, 8, 9, or 10 or more target polynucleotide regions. Exemplary target polynucleotides comprising two or more target polynucleotide regions are depicted in FIG. 3A-D as described previously.

A method provided herein can employ a target polynucleotide or a target polynucleotide region (target polynucleotide or region thereof) including, for example, a target region, a capture primer binding region and/or other region described herein or well known to those skilled in the art having two or more nucleotides. Other lengths include from 2 to 100 or more nucleotides and up to 10000 or more nucleotides as well as any of the various sizes exemplified previously.

A method of placing at least one target polynucleotide on a feature can employ a target polynucleotide or region thereof comprising a double-stranded polynucleotide of any of the various lengths set forth and/or exemplified previously including, for example, 2, 25, 150, 1100, 10000 or more base pairs and all integers in between.

A method provided herein can employ a double-stranded target polynucleotide or region thereof, including a capture primer region thereof, can comprise any number of mismatches. A particularly useful number of mismatches include, for example, 1, 2, 3, 4, 5, 6, 7, 8, 9, 10, 11, 12, 13, 14, 15, 16, 17, 18, 19, or 20 or more mismatches with its complementary sequence or, for example, a capture primer or other capture agent. Such mismatches are exemplified in FIGS. 4 and 6 and described with respect to a substrate produced by a method provided herein.

As exemplified previously with respect to a substrate provided herein, a method of this disclosure can employ a target polynucleotide comprising one or more regions having one or more capture primer binding regions. The capture primer binding region can be located on the 5' end, 3' end or at both a 5' and 3' end of a target polynucleotide region, or alternatively or additionally it can be located at an internal region of the target polynucleotide. The target polynucleotide can comprise two or more capture primer binding regions up to any number of capture primer regions applicable to any desired purpose. Similarly, as with the corresponding capture primers, a capture primer binding region can include one or more capture primer binding regions including, for example, a universal capture primer binding region, a sequencing primer binding site (SBS), a target-specific capture primer binding region, a predetermined cleavage site, such as a restriction site, and a linker region, for example, a linker region separating two or more regions of the capture primer binding region. Any and all possible combinations and permutations can be employed in a method provided herein as exemplified previously. For example, a method provided herein can employ any of the capture primer binding region designs exemplified previously such as a universal capture region and a SBS including any combination of the P5, P5', P7, P7', SBS3, SBS3', SBS8 and SBS8' and/or any other sequence that is sufficiently unique to function as universal primer, sequencing primer or any other sequence such as an adapter. The length of a capture primer binding region can comprise 5, 6, 7, 8, 9, 10, 11, 12, 13, 14, 15, 16, 17, 18, 19, 20, 21, 22, 23, 24, 25, 26, 27, 28, 29, 30 35, 40, 45, 50, 55, 60, 65, 70, 75, 80, 85, 90, 95, or 100 or more nucleotides as well as 400 down to 100 or fewer nucleotides as exemplified with respect to a substrate produced by a method provided herein.

A capture primer binding region of the target polynucleotide can be 100% complementary to a capture primer. A capture primer binding region of the target polynucleotide employed in a method provided herein can be, for example, at least 60%, 65%, 70%, 75%, 77%, 80%, 82%, 85%, 87%, 90%, 92%, 95%, or 97% or more complementary to a capture primer including, for example, comprising 1, 2, 3, 4, 5, 6, 7, 8, 9, or 10 or more nucleotide mismatches to a capture primer. In addition to one or more capture primer binding regions, a target polynucleotide can comprise one or more target regions including two or more target regions as exemplified previously. The size or length of the target region can be any of the lengths exemplified above with respect to a target polynucleotide or a target polynucleotide region.

A method provided herein can place at least one target molecule on a feature of a substrate through, for example, attachment to a to a target polynucleotide that can be attached, for example, to a capture primer. A method provided herein also can place a plurality of two or more target molecules in each of the referenced situations as exemplified previously including, for example, 2, 3, 4, 5, 6, 7, 8, 9, 10, 15, 20, 25, 30, 35, 40, 45, 50, 55, 60, 65, 70, 75, 80, 85, 90, 95, 100, 250, 500, 1,000, 5,000, 10,000 or more different, identical and/or similar target molecules as exemplified previously. The attachment of the target molecule to a target polynucleotide, capture primer, feature and/or substrate can be covalent or non-covalent.

In addition to at least one target molecule immobilized through a configuration described above, a method provided herein also can generate a plurality of amplicons of the target polynucleotide on feature or on a plurality of features on a substrate as exemplified in FIGS. 4 and 6. The plurality of amplicons can minimally fill a feature, partially fill a feature or fill to capacity a feature on a substrate. Accordingly, the amplicon density can be low, medium or high. Target polynucleotide design, methods to generate such amplicons and methods to control density are described further below with reference to methods of placing at least one target molecule on a feature of a substrate. The density of the amplicons is as described herein.

A method provided herein for single molecular placement of a target molecule on a substrate or feature can utilize any desired molecule. Exemplary categories of target molecules include, for example, a polypeptide, polynucleotide, carbohydrate, amino acid, nucleotide, monosaccharide, hapten, ligand, antigen, analyte, small molecule organic compound or inorganic compound. Exemplary species for each of the above categories are described further below. Exemplary species for each of these categories have been described previously, each of which can be equally employed in a method provided herein to generate a substrate provided herein as exemplified previously.

By way of exemplification, target molecules employed in a method provided herein can include, for example, a polypeptide of any size or activity and containing any natural or unnatural amino acid; a ribosomal polypeptide, including, but are not limited to, enzymes, receptors, antibodies, transcription factors, hormones, ligands, antigens, and haptens; a nonribosomal peptide, including, but are not limited to, toxins, siderophores, pigments, antibiotics, antibiotic precursors, cytostatics, and immunosuppressants; a nanopore, including MspA, outer membrane phospholipase A (OmpA), OmpC, OmpF, OmpG, Neisseria autotransporter lipoprotein (NalP), WZA, ClyA toxin, α-hemolysin, anthrax toxin, gramicidin A, maltoporin, PhoE, Tsx, F-pilus, SP1, mitochondrial porin (VDAC), Tom40, leukocidins and DNA origami nanopore; an antibiotic as exemplified previously; a toxin as exemplified previously; a hormone such as those exemplified previously; a hapten including, but are not limited to, aniline, o-aminobenzoic acid, m-aminobenzoic acid, p-aminobenzoic acid, uroshiol, quinine, hydralazine, fluorescein, biotin, digoxigenin, and dinitrophenol; a receptor including, for example, a receptor can be from an immune cell or from a non-immune cell as exemplified previously; a cytokine such as the chemokines, interferons, interleukins, lymphokines, tumour necrosis factor (TNF) and neuropeptides exemplified previously; an enzyme of any type including, for example, the metabolic enzymes, polymerases, ligases, reverse transcriptases, nucleases, helicases and transpoases exemplified previously; an antibody or antibody fragment as exemplified previously; a polynucleotide or oligonucleotide including, for example, DNA or RNA of any length or sequence as exemplified previously; an inorganic compound including, but are not limited to, carbides, carbonates, simple oxides of carbon (such as CO and CO2), cyanides quantum dots, metal nanoparticles, metal oxide nanoparticles and the like, minerals, sulfides, organometallic compounds, and bioinorganic compounds and minerals as exemplified previously; a small molecule as exemplified previously; a metabolite including, but are not limited to, alkaloids, glycosides, lipids, nonribosomal peptides, such as actinomycin-d, phenazines, natural phenols (including flavonoids), polyketide, terpenes, including steroids, and tetrapyrroles; a therapeutic agent including, for example, an organic compound, inorganic compound, peptide, hormone, small molecule, antibody, antigen, hapten, or any combination thereof. The therapeutic agent can be an antipyretic, analgesic, antimalarial drug, antibiotic, antiseptic, mood stabilizer, hormone replacement, oral contraceptive, stimulant, tranquilizer, antiviral drug, anti-cancer drug, immunosuppressant, and statin as described previously.

In some embodiments a method provided herein can be used to place at least one target molecule in each of a plurality of features on a substrate or an (also referred to herein as an array or an array of features) such as the plurality of features illustrated in FIG. 5. For example, the methods provide herein can be utilized with a substrate having a plurality of features arranged in any special pattern as exemplified previously including, for example, a grid of spots or patches, a repeating pattern, an irregular non-repeating pattern, hexagonal patterns, rectilinear patterns, grid patterns, patterns having reflective symmetry, patterns having rotational symmetry, or the like. The features can be any of a variety of densities as exemplified previously including, for example, from at least about 10 features/cm$^2$ to about 5,000,000 features/cm$^2$, or higher. The area of features of an array employed in a method provided herein can each have an area that is larger than about 100 nm$^2$ to about 500 μm$^2$ as well as any area in between. The features on the surface of an array substrate can be non-contiguous, being separated by interstitial regions of the surface. In particular embodiments, the methods are used with features that are concave features in a surface (e.g. wells) including, for example, microwells or nanowells, and the features can contain a gel material as exemplified previously. Methods and compositions for making and using substrates having gel containing features, such as wells, are set forth in, for example, US 2014/0243224, which is incorporated herein by reference. The methods can be performed with arrays having a high density, medium density or low density of features as exemplified previously. The methods described herein can be performed with features that are beads or beads in wells. The beads can be composed of any material allowing immobilization of polynucleotides to the surface including, but are not limited to, plastics, ceramics, glass, polystyrene, carbon graphite and the like, as well as any other materials outlined herein for solid supports can all be used.

In some embodiments, a method provided is used to place at least one target molecule on a feature or in each of a plurality of features wherein the feature size is selected from a range favoring kinetic exclusion amplification (KEA) and the formation of single molecular placement in the feature. As exemplified previously by reference to a nanowell, the well diameter can be varied between about 30 nm and about 1 μm, between about 50 nm and about 800 nm, between about 70 nm and about 600 nm, or between 100 nm and about 400 nm. In some embodiments, the well has a diameter of about 400 nm. In some embodiments, the well has a diameter of less than about 1 μm.

By way of exemplification, in one specific embodiment, the methods disclosed herein can comprise (a) attaching a plurality of first capture primers to a surface; (b) attaching a plurality of second capture primers to a surface; and (c) attaching a double-stranded target polynucleotide to a second capture primer of the second capture primers, wherein (i) the double-stranded target polynucleotide comprises a first parent strand and a second parent strand; (ii) the double-stranded target polynucleotide comprises a second capture primer binding region in the first and second parent strands; (iii) the second capture primer binding region of the first parent strand is 100% complementary to a second capture primer of the plurality of second capture primers; and (iv) the second capture primer binding region of the second parent strand is less than 100% identical to the second capture primer of the plurality of second capture primers. The method can further comprise attaching a target molecule to the target polynucleotide. The target molecule can be attached to the target polynucleotide prior to the attachment of the target polynucleotide to the second capture primer. Attaching the plurality of first capture primers to the surface can occur prior to the attachment of the plurality of second capture primers to the surface. Alternatively, the attachment of the plurality of first capture primers to the surface can occur simultaneously as the attachment of the plurality of second capture primers to the surface. The target polynucleotide can further comprise a first capture binding region. At least one strand of the first capture binding region can hybridize to a first capture primer of the plurality of first capture primers. The method can further comprise producing a plurality of amplicons. The plurality of amplicons can comprise copies of the target polynucleotide. The plurality of amplicons can be produced by conducting an amplification reaction. The amplification reaction can include a first recombinase polymerase amplification (RPA). The first RPA can comprise extending the first capture primer and the second capture primer that are hybridized to the target polynucleotide to produce a plurality of first amplicons of the target polynucleotide. The plurality of amplicons can be produced by conducting one or more additional amplification reactions. The one or more additional amplification reactions can comprise one or more additional recombinase polymerase amplifications (RPAs). The one or more additional RPAs can comprise (a) attaching one or more first capture primers of the plurality of capture primers to one or more amplicons of the plurality of first amplicons; and (b) extending the one or more first capture primers to produce a plurality of additional amplicons. The one or more additional RPAs can comprise (a) attaching one or more second capture primers of the plurality of second capture primers; and (b) extending the one or more second capture primers to produce a plurality of additional amplicons. In some instances, a second capture primer does not hybridize to an amplicon containing a complement of the second parent strand. In some instances, a second capture primer does not hybridize to a second capture primer binding region of an amplicon that is a complement of the second capture primer binding region of the second parent strand.

Figure 7:
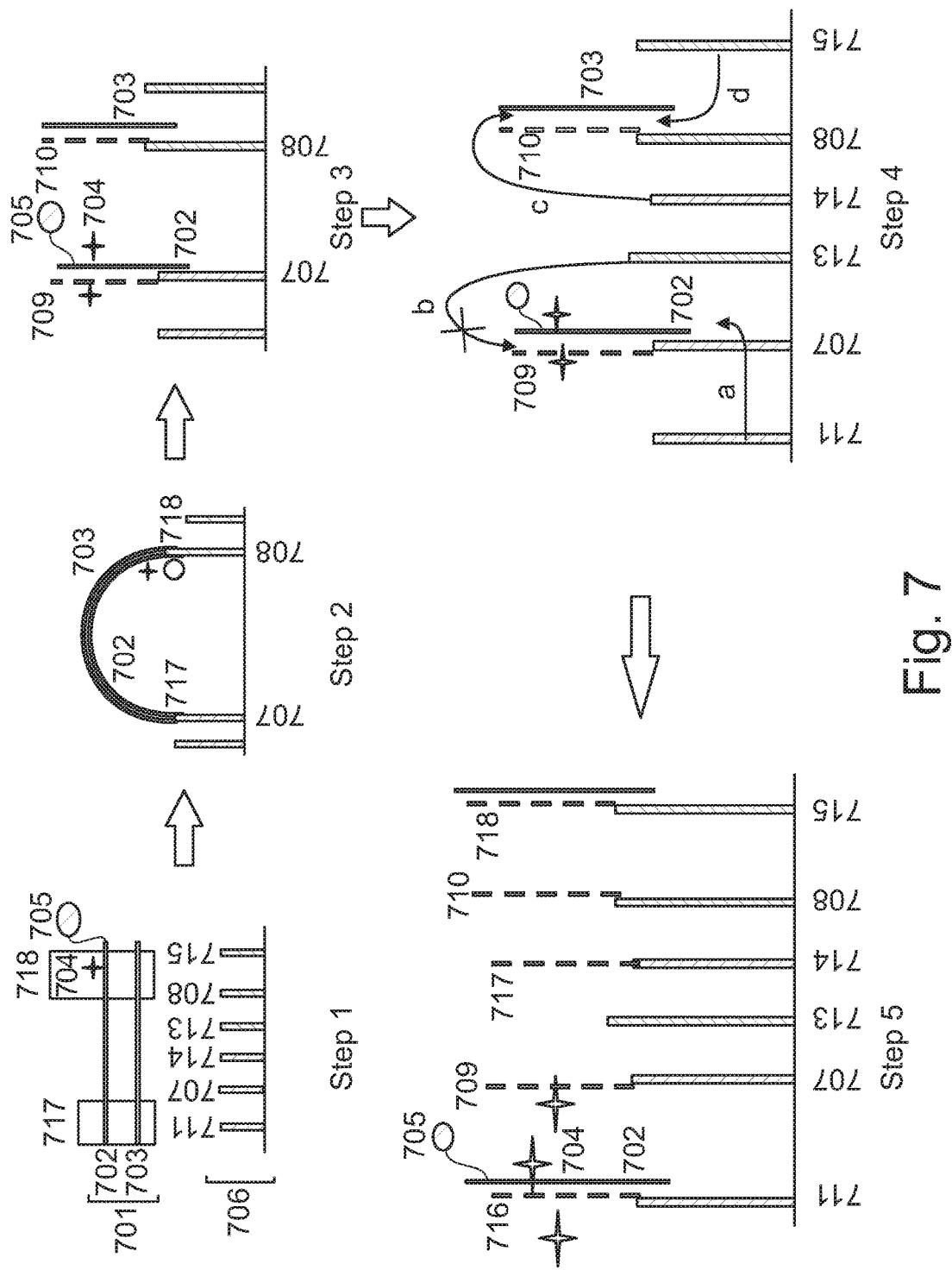
FIG. 7 shows an exemplary workflow for generating a substrate.

An exemplary method of producing a substrate is depicted in FIG. 7. As shown in step 1 of FIG. 7, a surface (706) comprising a plurality of first capture primers (707, 711, 714) and a plurality of second capture primers (708, 713, 715) is contacted with a target molecule (705) attached to a target polynucleotide (701). The target polynucleotide (701) comprises a first parent strand (703) and a second parent strand (702). The first parent strand (703) and the second parent strand (702) contain a first capture primer binding region (717) and a second capture primer binding region (718). Within the second capture primer binding region (718) there is a mismatch region between the first parent strand (703) and the second parent strand (702). The second capture primer binding region (718) of the second parent strand (702) contains at least one nucleotide difference (704) from a second capture primer of the plurality of second capture primers (708, 713, 715). The second capture primer binding region (718) of the first parent strand (703) is 100% complementary to the second capture primer of the plurality of second capture primers (708, 713, 715). As shown in step 2, a first capture primer (707) of the plurality of first capture primers (707, 711, 714) hybridizes to the first capture primer binding region (717) of the second parent strand (702). A second capture primer (708) of the plurality of second capture primers (708, 713, 715) hybridizes to the second capture binding region (718) of the first parent strand (703). As shown in step 3, the first and second parent strands are amplified to produce a first plurality of amplicons. The first capture primer (707) displaces the first parent strand (703) and is extended to produce an amplicon of the second parent strand (709). The amplicon of the second parent strand (709) contains a complement of the second parent strand. As such, the amplicon of the second parent strand (709) contains a complement of the second capture primer binding region (718) of the second parent strand (702). As also shown in step 3, the second capture primer (708) displaces the second parent strand (702) and is extended to produce an amplicon of the first parent strand (710). As shown in step 4, one or more additional amplification reactions are conducted to produce a second plurality of amplicons. In step 4 *a*, a first capture primer (711) hybridizes to the first capture primer binding region of the second parent strand and displaces the first capture primer (707). In step 4 *b*, a second capture primer (713) attempts to hybridize to the second capture primer binding region of the amplicon of the second parent strand (709). However, because the second capture primer binding region of the amplicon of the second parent strand (709) is a complement of the second capture primer binding region of the second parent strand, the second capture primer binding region of the amplicon of the second parent strand (709) is not 100% complementary to the second capture primer (711). The second capture primer (711) is unable to displace the amplicon of the second parent strand (709) from the second parent strand. As such, the amplicon of the second parent strand that contains a second capture primer binding region that is complementary to the second capture biding region of the second parent strand cannot act as a template for extension of a second capture primer. As shown in step 4 *c*, because the first capture primer binding region of the amplicon of the first parent strand (710) is 100% complementary to a first capture primer (714), the first capture primer (714) can displace the first parent strand (703) and hybridize to the first capture primer binding region of the amplicon of the first parent strand (710). The amplicon of the first parent strand (710) can serve as a template for the extension of the first capture primer (714). As shown in step 4 *d*, a second capture primer (715) can hybridize to the second capture primer binding region of the first parent strand (703), thereby displacing the second capture primer (708). As shown in step 5, the first capture primer (711) can be extended to produce an amplicon of the first parent strand (716). Also shown in step 5, the first capture primer (714)

can be extended to produce an amplicon of the amplicon of the first parent strand (717). Also shown in step 5, the second capture primer (715) can be extended to produce an amplicon of the first parent strand (718).

Accordingly, the disclosure provides a method of placing a single target molecule on a feature of a substrate. The method includes: (a) hybridizing a plurality of first and second capture primers immobilized to a feature on a substrate with at least one target polynucleotide, said target polynucleotide a comprising a target region flanked by first and second capture primer binding regions complementary to said first and second capture primers, wherein said second capture primer binding region comprises a base pair mismatch to said second capture primer and being linked to a target molecule, and (c) amplifying said at least one target polynucleotide at an average amplification rate that exceeds an average transport rate of a target polynucleotide to a feature to produce a plurality of clonal amplicons complementary to said target polynucleotide. The method can utilize a substrate having one feature or a plurality of features. The feature or features can be a bead, well, including a microwell or nanowell, channel, ridge, projection or combination thereof. The method can place at least one target molecule, including a single target molecule in a feature or in each of a plurality of features. The method can fill a feature or features to capacity with a plurality of clonal amplicons of a target polynucleotide. Interstitial regions between a plurality of features can lack a target polynucleotide. The method can be used with a substrate having a plurality of features, including two or more features, and can place different single target molecules in each of the different features within the plurality. The method can be used with a target polynucleotide selected from RNA, DNA, PNA or double stranded DNA (dsDNA). The length of the target polynucleotide use by a method provided herein can be less than 1,000 nucleotides and/or it can be between 10 to 25, 26 to 50, 51 to 100, 101 to 200, 201 to 300, 301 to 400, 401 to 500, 501 to 600, 601 to 700, 701 to 800, 801 to 900, or 901 to 1000 nucleotides. The target molecule placed on one or more features by the method can be a polypeptide, polynucleotide, carbohydrate, amino acid, nucleotide, monosaccharide, hapten, ligand, antigen, analyte, small molecule organic compound or inorganic compound. Polypeptide target molecules can be a nanopore, binding polypeptide or enzyme. A nanopore can be MspA, OmpF, OmpG, NalP, WZA, ClyA toxin, α-hemolysin, anthrax toxin, leukocidins or a DNA origami nanopore. A binding polypeptide can be an antibody, a Fab, a Fab', a F(ab')2, a scFV, a diabody, a triabody, a minibody and a single-domain antibody (sdAB) or T cell receptor. An enzyme can be a polymerase, helicase, recombinase, transposase or ligase. The method can be used with a substrate selected from one or more materials such as glass, silicon, plastic or biopolymer. The substrate can further include a hydrogel or covalently-linked gel.

The substrates of the disclosure having a single target molecule in a feature or having a single target molecule in each of a plurality of features can be utilized to interrogate single molecular entities. One or more molecules to be interrogated can be in solution and the immobilized target molecule can be used to determine a characteristic of the one or molecules to be interrogated. For example, the sequence a single polynucleotide or a plurality of single polynucleotides can be determined by nanopore sequencing where the nanopore corresponds to the immobilized target molecule. Alternatively, one or molecules to be interrogated can be the immobilized target molecules and one or more molecules in solution can be used to probe or determine a characteristic of each of the immobilized target molecules. For example, the immobilized target molecule can be a library of different enzyme variants and the probes in solution can be a substrate or a plurality of different substrates to determine a catalytic characteristic of each of the different enzyme variants. The opposite orientation also can be utilized where the substrate, for example, corresponds to the immobilized target molecule on a feature and are contacted with the different enzyme variants to measure a catalytic characteristic. Given the teachings and guidance provided herein, those skilled in the art will understand that a large number of different target molecules can be utilized in a substrate provided herein to interrogate or to be interrogated for the determination of one or more molecular characteristics. Exemplary characteristics include, for example, determining a polynucleotide sequence, a polypeptide sequence, a binding activity, a catalytic activity and the like.

By way of further exemplification with respect to sequencing, some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the polynucleotide to be sequenced passes through a nanopore. The nanopore can be a synthetic pore or biological membrane protein, such as α-hemolysin. As the target nucleic acid passes through the nanopore, each basepair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

The methods here can also be useful in molecular binding affinity screening. In embodiments, a single molecular antibody can be anchored on substrate described herein. The single antigen binding event can be detected by fluorescence staining. The fluorescence staining technique includes those well known in the art, including, for example, Illumina Infinium assay or ELISA (enzyme linked immunosorbent assay) techniques. In certain embodiments, the concentration of the antigen in the solution can be quantitatively analyzed by counting the single molecules fluorescence spots such techniques known in the art. (T. Blicharz, et al. "Fiber-Optic Microsphere bead antibody array for the analysis of inflammatory cytokines in saliva" Anal. Chem. 2009, 81, 2106.). In embodiments, the methods described herein are applicable for in vitro diagnosis.

An advantage of the methods set forth herein is that they provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized target molecules, the system including components such as pumps, valves, reservoirs, fluidic lines and the like. A flow cell can be configured and/or used in an integrated system for interrogation and. Exemplary flow cells are described, for example, in US 2010/0111768 A1 and U.S. Ser. No. 13/273,666, each of which is incorporated herein by reference. As exemplified for flow cells, one or more of the fluidic components of an integrated system can be used for different steps in an interrogation. Taking a binding reaction embodiment as an example, one or more of the fluidic components of an integrated system can be used for a binding step and for the delivery of reagents for detection. Alternatively, an integrated system can include separate fluidic systems to carry out a binding step and to carry out detection methods. Examples of integrated sequencing systems that are capable of creating amplified nucleic acids and also determining the sequence of the nucleic acids include, without limitation, the MiSeq™ platform (Illumina, Inc., San Diego, Calif.) and devices described in U.S. Ser. No. 13/273,666, which is incorporated herein by reference.

Further disclosed herein are kits comprising any of the substrates disclosed herein. A kit can comprise (a) a substrate comprising a feature, wherein the feature comprises (i) a plurality of first capture primers; and (ii) a plurality of second capture primers; and (b) a target polynucleotide comprising a first double-stranded target polynucleotide region, wherein (i) the first double-stranded target polynucleotide region comprises a second capture primer binding region; (ii) a first strand of the second capture primer binding region is 100% complementary to a second capture primer of the second capture primers; and (iii) the second capture primer binding region comprises at least one nucleotide mismatch between the first strand and a second strand.

A kit can comprise a substrate comprising a feature, wherein the feature comprises (a) a plurality of first capture primers; (b) a plurality of second capture primers; and (c) a target polynucleotide comprising a first double-stranded target polynucleotide region, wherein (i) the first double-stranded target polynucleotide region comprises a second capture primer binding region; (ii) a first strand of the second capture primer binding region is 100% complementary to a second capture primer of the second capture primers; and (iii) the second capture primer binding region comprises at least one nucleotide mismatch between the first strand and a second strand.

A kit can comprise (a) a substrate comprising a feature, wherein the feature comprises (i) a plurality of first capture primers; and (ii) a plurality of second capture primers; and (b) a target polynucleotide comprising a first double-stranded target polynucleotide region and a second double-stranded target polynucleotide region, wherein (i) the first double-stranded target polynucleotide region comprises a second capture primer binding region; (ii) a first strand of the second capture primer binding region is 100% complementary to a second capture primer of the second capture primers; and (iii) the second capture primer binding region comprises at least one nucleotide mismatch between the first strand and a second strand. The second double-stranded target polynucleotide region can comprise a first capture primer binding region.

A kit can comprise (a) a substrate comprising a feature, wherein the feature comprises (i) a plurality of first capture primers; and (ii) a plurality of second capture primers; (b) a first target polynucleotide comprising a first double-stranded target polynucleotide region, wherein (i) the first double-stranded target polynucleotide region comprises a second capture primer binding region; (ii) a first strand of the second capture primer binding region is 100% complementary to a second capture primer of the second capture primers; and (iii) the second capture primer binding region comprises at least one nucleotide mismatch between the first strand and a second strand; and (c) a second target polynucleotide region comprising a second double-stranded target polynucleotide region. The second double-stranded target polynucleotide region can comprise a first capture primer binding region.

A kit disclosed herein can comprise a substrate as depicted in FIG. 2. As shown in FIG. 2, a kit can comprise a substrate (201) comprising (a) a plurality of first capture primers (202, 203, 204); (b) a plurality of second capture primers (205, 206, 207); (c) a target polynucleotide (208); (d) a target molecule (209); and (e) a plurality of amplicons (210, 211, 212, 213, 214).

A kit disclosed herein can comprise a substrate as depicted in FIG. 5. As shown in FIG. 5, a kit can comprise a substrate (501) comprising (a) a first feature (502) comprising (i) a first plurality of first capture primers (504, 505, 506); (ii) a first plurality of second capture primers (507, 508, 509); (iii) a first target polynucleotide (510); (iv) a first target molecule (511); and (v) a first plurality of amplicons (512, 513, 514, 515, 516); and (b) a second feature (503) comprising (i) a second plurality of first capture primers (520, 521, 522); (ii) a second plurality of second capture primers (523, 524, 525); (iii) a second target polynucleotide (526); (iv) a second target molecule (527); and (v) a second plurality of amplicons (528, 529, 530, 531, 532).

Figure 8:
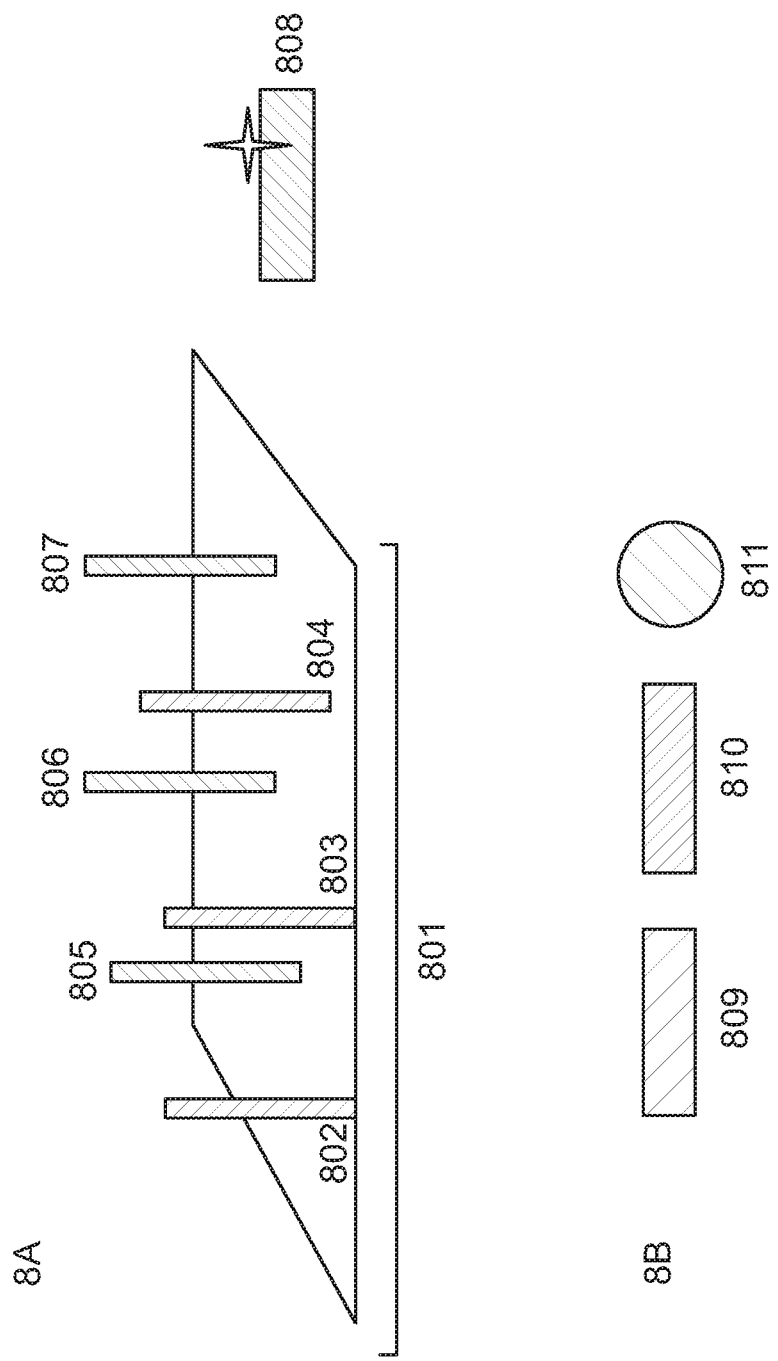
FIG. 8 shows exemplary kits.

Exemplary components of the kits disclosed herein are exemplified in FIG. 8A-B. As shown in FIG. 8A, a kit can comprise (a) a substrate (801) comprising (i) a plurality of first capture primers (802, 803, 804); and (ii) a plurality of second capture primers (805, 806, 807); and (b) a target polynucleotide (808). As shown in FIG. 8B, the kit can further comprise one or more additional target polynucleotides (809), amplicons (810), target molecules (811), or a combination thereof.

The target polynucleotide of any of the kits disclosed herein can further comprise one or more of the target polynucleotide regions disclosed herein. For example, the target polynucleotide can further comprise a second target polynucleotide region comprising a first capture primer binding domain. The first capture primer binding region can hybridize to a first capture primer of the plurality of first capture primers. In another example, the target polynucleotide can further comprise an additional target polynucleotide region comprising a target region. The target polynucleotide can comprise one or more additional target polynucleotide regions comprising a barcode, primer binding region, linker region, adapter region, or a combination thereof.

The target polynucleotide of any of the kits disclosed herein can be part of the substrate. For example, the target polynucleotide can be attached to a second capture primer of the substrate. Alternatively, the target polynucleotide of any of the kits disclosed herein can be separate from the substrate. For example, the kit can comprise a first container comprising the substrate and a second container comprising the target polynucleotide.

The kits disclosed herein can further comprise a target molecule. The target molecule can be any of the target molecules disclosed herein. For example, the target molecule can be a nanopore. The target molecule can be attached to the target polynucleotide. The target molecule can be a part of the substrate. For example, the target molecule can be attached to the target polynucleotide that is attached to a first capture primer or a second capture primer of the substrate. Alternatively, or additionally, the target molecule is not attached to the target polynucleotide. For example, the kit can comprise a first container comprising the target polynucleotide and a second container comprising the target molecule. The target molecule can be provided with the substrate. For example, the kit can comprise a first container comprising the substrate and the target molecule and a second container comprising the target polynucleotide. Alternatively, the kit can comprise a first container comprising the substrate, target polynucleotide and target molecule.

The kit can further comprise a plurality of amplicons. The plurality of amplicons can be part of the substrate. For example, the plurality of amplicons can be attached to the plurality of first primers, plurality of second primers, or a combination thereof. The amplicons can be copies of the target polynucleotides.

The substrates of any of the kits disclosed herein can comprise two or more features.

It is understood that modifications which do not substantially affect the activity of the various embodiments of this invention are also included within the definition of the invention provided herein. Accordingly, the following examples are intended to illustrate but not limit the present invention.

EXAMPLE I

Kinetic Exclusion Amplification Using a Mismatched Capture Primer Binding Region This Example shows that a mismatched capture primer binding region prevents recombinase polymerase amplification (RPA) at the mismatched target polynucleotide terminus.

Figure 9:
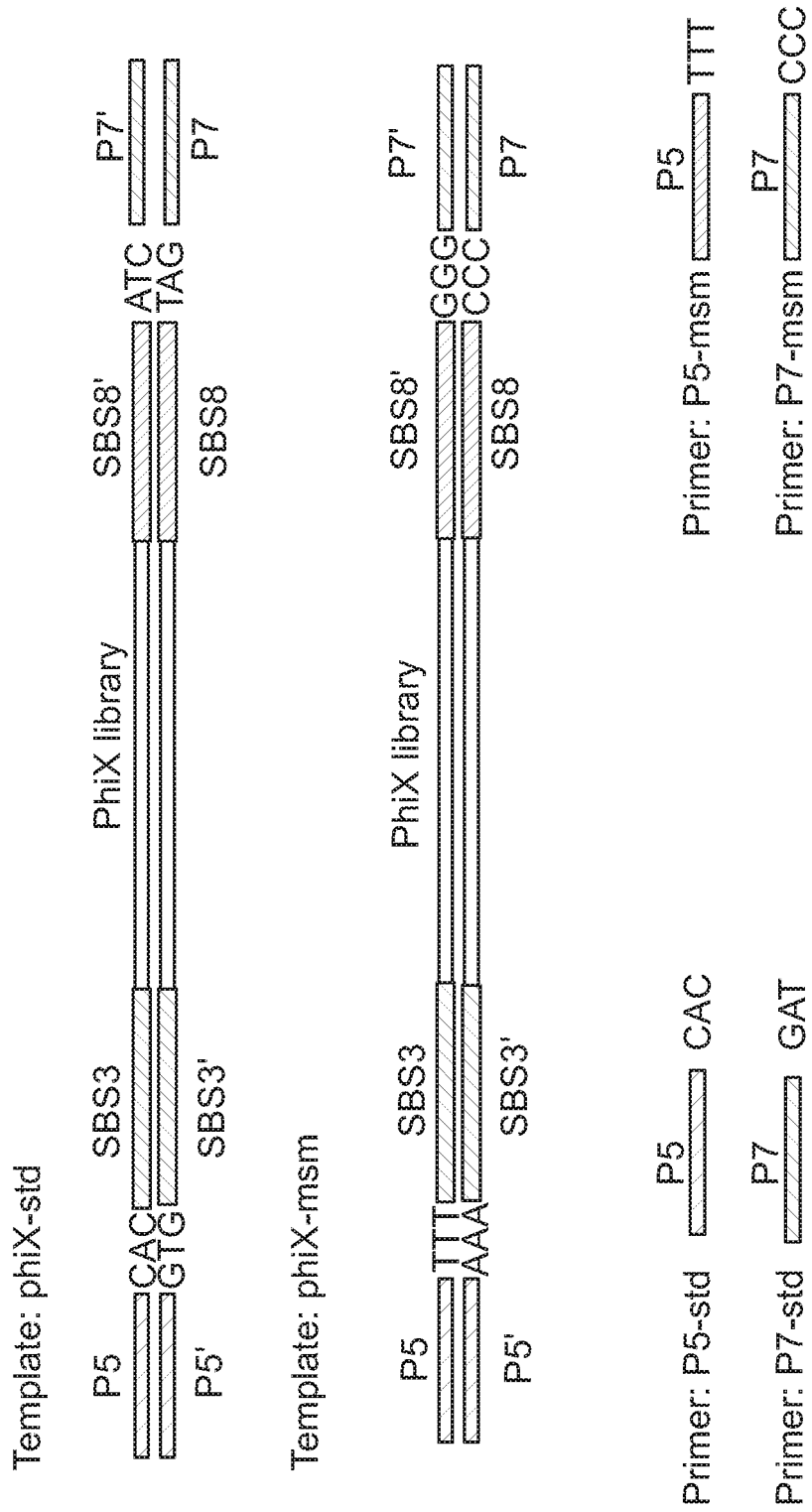
FIG. 9 shows the target polynucleotide and capture primer binding region designs employed in a kinetic exclusion amplification (KEA) reaction using matched and mismatched capture primer/capture primer binding regions.

To confirm that mismatched base pairs between a capture primer binding region and a capture primer can prevent a RPA reaction, the target polynucleotides and capture primers shown in FIG. 9 were employed in RPA reaction using a commercial kit TwistDX according to the manufacturer's instructions. Briefly, the target polynucleotides employed a ~500 bp phiX target region flanked by capture primer regions termed standard (std) or mismatched (msm). By design, the primer set P5-std/P7-std is complimentary to the capture primer binding regions in the target polynucleotide phiX-std and P5-msm/P7-msm is complimentary to the capture primer binding regions in the target polynucleotide phiX-msm. P5-std/P7-std has 3 bp mismatched to template phiX-msm whereas P5-msm/P7-msm has 3 bp mismatching to template phiX-std.

phiX target (13.2 uL) containing phix target molecule 5E-16 mol was mixed with 2.4 µL 10 µM matched or mismatched primers, then added with TwistDx rehybdration buffer 29.5 µL. The above solution was transferred to TwistDx reaction pellet and mixed by pipette. The reaction was initiated by adding 2.5 µl 280 mM magnesium acetate, and left to react for 8 to 10 mins. The reaction was stopped for gel analysis by PCR product purification process.

Figure 10:
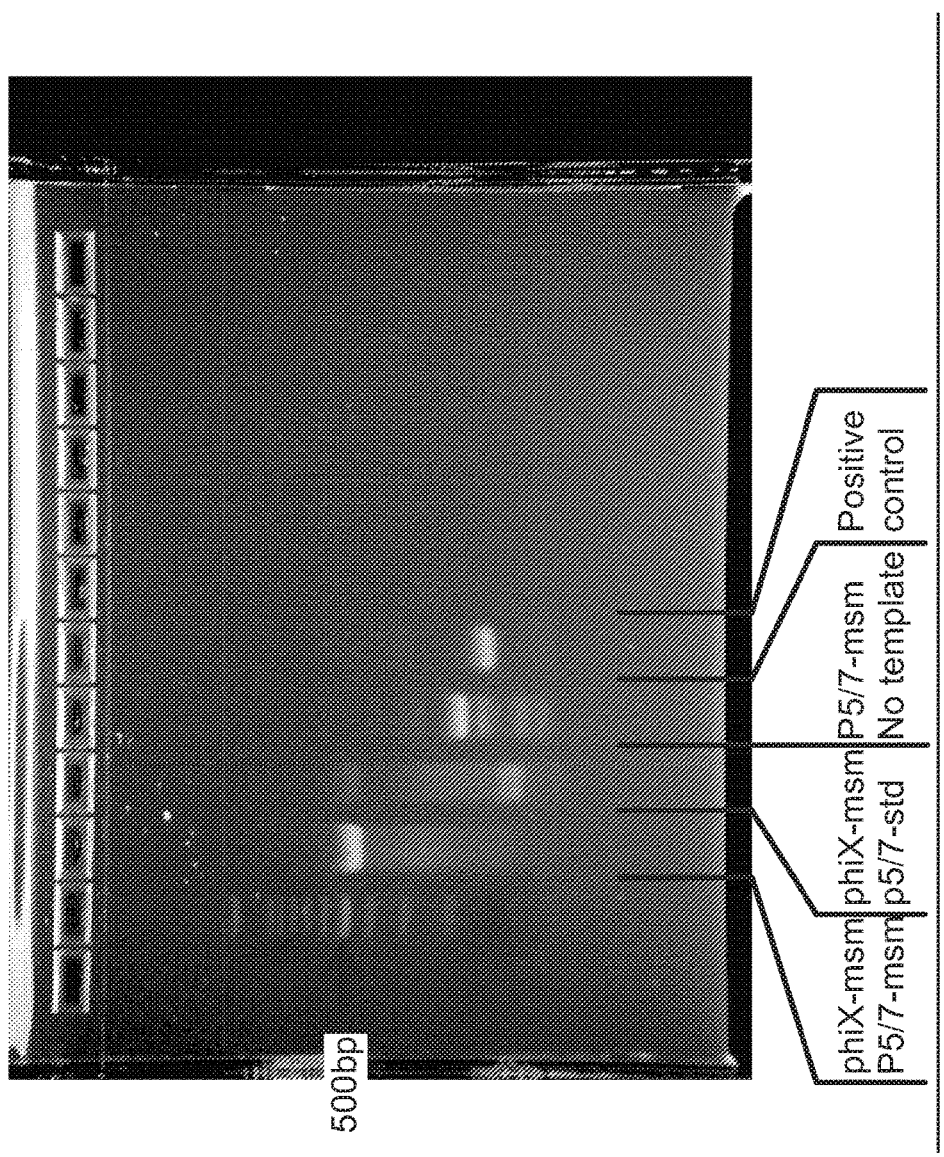
FIG. 10 shows the amplicon products for the target polynucleotides illustrated in FIG. 9.

Following a KEA reaction the amplicons were separated by gel electrophoresis (2% E-Gel electrophoresis, Life Technologies) and the results are shown in FIG. 10. Briefly, the RPA reaction with complimentary capture primer-capture primer binding region combinations, for example, P5-msm/P7-msm plus phiX-msm, resulted in a good yield of amplicon formation. However, the mismatched capture primer-capture primer binding region combinations in the RPA reaction did not generate or resulted low yield of the 500 bp amplicon product.

These results confirm that the mismatch design can effectively stop an RPA reaction at the mismatched end of a target polynucleotide.

Throughout this application various publications have been referenced within parentheses. The disclosures of these publications in their entireties, including GenBank and GI number publications, are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A substrate comprising:
   a. a plurality of first and second capture primers immobilized to a feature on the substrate;
   b. at least one target polynucleotide, one end attached to one of said capture primers and the other end linked to a target molecule, wherein said target polynucleotide comprises a target region flanked by first and second capture primer binding regions complementary to said first and second capture primers, said second capture primer binding region comprising a base pair mismatch to said second capture primer, and
   c. a plurality of clonal amplicons complementary to said target polynucleotide immobilized to said feature.

2. The substrate of claim 1, wherein said base pair mismatch is a 1, 2, 3, 4, 5, 6, 7, 8, 9, or 10 base pair mismatch.

3. The substrate of claim 2, wherein said base pair mismatch is a three base pair mismatch.

4. The substrate of claim 1, further comprising a plurality of features.

5. The substrate of claim 4, wherein each of said plurality of features comprises a single target molecule.

6. The substrate of claim 5, wherein two or more of said plurality of features comprise different single target molecules.

7. The substrate of claim 5, wherein said features are filled to capacity with said plurality of clonal amplicons.

8. The substrate of claim 4, comprising one or more materials selected from the group consisting of glass, silicon, plastic, and biopolymer.

9. The substrate of claim 4, wherein the features are separated by interstitial regions that lack a target polynucleotide.

10. The substrate of claim 9, wherein the features comprises a bead, a well, a channel, a ridge, a projection or a combination thereof.

11. The substrate of claim 10, wherein said well is a microwell or a nanowell.

12. The substrate of claim 11, further comprising a hydrogel or a covalently-linked gel.

13. The substrate of claim 1, wherein said feature comprises a single target molecule.

14. The substrate of claim 1, wherein said feature is filled to capacity with said plurality of clonal amplicons.

15. The substrate of claim 1, wherein said target polynucleotide comprises one or more polynucleotides selected from the group consisting of RNA, DNA and PNA.

16. The substrate of claim 15, wherein said target polynucleotide comprises double stranded DNA.

17. The substrate of claim 1, wherein said target polynucleotide comprises less than 1,000 nucleotides.

18. The substrate of claim 17, wherein said target polynucleotide comprises between 10 to 25, 26 to 50, 51 to 100, 101 to 200, 201 to 300, 301 to 400, 401 to 500, 501 to 600, 601 to 700, 701 to 800, 801 to 900, or 901 to 999 nucleotides.

19. The substrate of claim 1, wherein said target molecule comprises a polypeptide, polynucleotide, carbohydrate, amino acid, nucleotide, monosaccharide, hapten, ligand, antigen, analyte, small molecule organic compound or inorganic compound.

20. The substrate of claim 19, wherein said target molecule comprises a polypeptide.

21. The substrate of claim 20, wherein said polypeptide is selected from the group consisting of a nanopore, a binding polypeptide, and an enzyme.

22. The substrate of claim 21, wherein said nanopore is selected from the group consisting of MspA, OmpF, OmpG, NalP, WZA, ClyA toxin, α-hemolysin, anthrax toxin, leukocidins, ion channel, protein nanopore, and DNA origami nanopore.

23. The substrate of claim 21, wherein said binding polypeptide is selected from the group consisting of an antibody, a Fab, a Fab', a F(ab')$_2$, a scFv, a diabody, a triabody, a minibody and a single-domain antibody (sdAB), T cell receptor, microcins, Neuropeptides, G-protein coupled receptors, antibody, epidermal growth factor receptor and HER2.

24. The substrate of claim 21, wherein said enzyme is selected from the group consisting of a recombinase, a polymerase, a helicase, a transposase, a ligase, a deaminase, an oxidase, and a kinase.

25. A method of placing a single target molecule on a feature of a substrate comprising:
   a. hybridizing a plurality of first and second capture primers immobilized to a feature on a substrate with at least one target polynucleotide, said target polynucleotide comprising a target region flanked by first and second capture primer binding regions complementary to said first and second capture primers, wherein said second capture primer binding region comprises a base pair mismatch to said second capture primer, and being linked to a target molecule, and
   b. amplifying said at least one target polynucleotide at an average amplification rate that exceeds an average transport rate of a target polynucleotide to a feature to produce a plurality of clonal amplicons complementary to said target polynucleotide.

* * * * *

UNITED STATES PATENT AND TRADEMARK OFFICE
CERTIFICATE OF CORRECTION

PATENT NO. : 10,350,570 B2
APPLICATION NO. : 15/535695
DATED : July 16, 2019
INVENTOR(S) : Kevin L. Gunderson et al.

It is certified that error appears in the above-identified patent and that said Letters Patent is hereby corrected as shown below:

In the Drawings

Sheet 6, Fig. 6, "srtand" should be -- strand --.

Sheet 6, Fig. 6, "probality" should be -- probability --.

In the Specification

In Column 5, Line 5, "microtier" should be -- microtiter --.

In Column 11, Line 45, "polpypeptide" should be -- polypeptide --.

In Column 17, Line 51, "SEQ" should be -- (SEQ --.

In Column 18, Line 7, ""SBS8'," should be -- "SBS8'", --.

In Column 20, Line 4, "some" should be -- Some --.

In Column 29, Line 4, "nm)," should be -- nm, --.

In Column 29, Line 5, "um" should be -- um. --.

In Column 30, Line 29, "acetylphenalalanine," should be -- acetylphenylalanine, --.

In Column 30, Line 30, "acetylphenalalanine," should be -- acetylphenylalanine, --.

In Column 30, Line 30, "aminoburyic" should be -- aminobutyric --.

Signed and Sealed this
Twelfth Day of November, 2019

Andrei Iancu
*Director of the United States Patent and Trademark Office*

CERTIFICATE OF CORRECTION (continued)

U.S. Pat. No. 10,350,570 B2

In Column 30, Line 49, "palmitoylatation," should be -- palmitoylation, --.

In Column 31, Line 61, "thrombaxane," should be -- thromboxane, --.

In Column 32, Line 18, "aminoabenzoic" should be -- aminobenzoic --.

In Column 32, Line 19, "uroshiol," should be -- urushiol, --.

In Column 33, Line 63, "9° NTM" should be -- 9°NTM --.

In Column 34, Line 8, "transcripase." should be -- transcriptase. --.

In Column 35, Line 20, "bispefic" should be -- bi-specific --.

In Column 38, Line 8, "C(3'" should be -- C (3' --.

In Column 38, Line 9, "N(5'" should be -- N (5' --.

In Column 38, Line 13, "C(3'" should be -- C (3' --.

In Column 38, Line 14, "N(5'" should be -- N (5' --.

In Column 39, Line 38, "SV40 pA-R" should be -- SV40pA-R --.

In Column 40, Line 2, "poyladenylated." should be -- polyadenylated. --.

In Column 41, Lines 12-13, "acetylphenalalanine," should be -- acetylphenylalanine, --.

In Column 41, Line 13, "acetylphenalalanine," should be -- acetylphenylalanine, --.

In Column 41, Lines 13-14, "aminoburyic" should be -- aminobutyric --.

In Column 53, Line 59, "aminoabenzoic" should be -- aminobenzoic --.

In Column 53, Line 60, "uroshiol," should be -- urushiol, --.

In Column 56, Line 35, "4 a," should be -- 4a, --.

In Column 56, Line 38, "4 b," should be -- 4b, --.

In Column 56, Line 54, "4 c," should be -- 4c, --.

In Column 56, Line 62, "4 d," should be -- 4d, --.

In Column 62, Line 13, "rehybdration" should be -- rehydration --.

In the Claims

In Column 65, Line 27 approx., Claim 7, "said features" should be -- said plurality of features --.